(12) United States Patent
Jo et al.

(10) Patent No.: US 12,428,623 B2
(45) Date of Patent: Sep. 30, 2025

(54) GENERATION OF MIDBRAIN-SPECIFIC ORGANOIDS FROM HUMAN PLURIPOTENT STEM CELLS

(71) Applicants: AGENCY FOR SCIENCE, TECHNOLOGY AND RESEARCH, Singapore (SG); NATIONAL UNIVERSITY OF SINGAPORE, Singapore (SG)

(72) Inventors: Junghyun Jo, Singapore (SG); Huck Hui Ng, Singapore (SG); Hyunsoo Shawn Je, Singapore (SG)

(73) Assignees: AGENCY FOR SCIENCE, TECHNOLOGY AND RESEARCH, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 544 days.

(21) Appl. No.: 16/085,553

(22) PCT Filed: Mar. 14, 2017

(86) PCT No.: PCT/SG2017/050126
§ 371 (c)(1),
(2) Date: Sep. 14, 2018

(87) PCT Pub. No.: WO2017/160234
PCT Pub. Date: Sep. 21, 2017

(65) Prior Publication Data
US 2019/0169576 A1 Jun. 6, 2019

(30) Foreign Application Priority Data
Mar. 14, 2016 (SG) .............................. 10201601965P

(51) Int. Cl.
*C12N 5/074* (2010.01)
*C12N 5/00* (2006.01)
*C12N 5/0793* (2010.01)

(52) U.S. Cl.
CPC ......... *C12N 5/0696* (2013.01); *C12N 5/0018* (2013.01); *C12N 5/0062* (2013.01); *C12N 5/0619* (2013.01); *C12N 2501/119* (2013.01); *C12N 2501/13* (2013.01); *C12N 2501/15* (2013.01); *C12N 2501/33* (2013.01); *C12N 2501/41* (2013.01); *C12N 2501/415* (2013.01); *C12N 2501/727* (2013.01); *C12N 2501/999* (2013.01); *C12N 2506/02* (2013.01);
(Continued)

(58) Field of Classification Search
CPC .. C12N 5/0696; C12N 5/0018; C12N 5/0062; C12N 5/0619; C12N 2501/119; C12N 2501/13; C12N 2501/15; C12N 2501/33; C12N 2501/41; C12N 2501/415; C12N 2501/727; C12N 2501/999; C12N 2506/02; C12N 2513/00; C12N 2533/54; C12N 2533/56; C12N 2533/72; C12N 2533/74; C12N 2533/76; C12N 2533/78; C12N 2533/90
USPC ........................................................ 435/377
See application file for complete search history.

(56) References Cited

U.S. PATENT DOCUMENTS

2015/0265652 A1    9/2015   George et al.
2015/0330970 A1*  11/2015   Knoblich ............ C12N 5/0619
                                              435/29
(Continued)

FOREIGN PATENT DOCUMENTS

CN    104024401        9/2014
EP    3190176 A1       12/2017
(Continued)

OTHER PUBLICATIONS

Tieng et al. "Engineering of midbrain organoids containing long-lived dopaminergic neurons." Stem Cells and Development 23.13 (2014): 1535-1547 (Year: 2014).*
(Continued)

*Primary Examiner* — Maria G Leavitt
*Assistant Examiner* — Alexander W Nicol
(74) *Attorney, Agent, or Firm* — Womble Bond Dickinson (US) LLP

(57) ABSTRACT

The present disclosure provides a method of deriving and maintaining a midbrain-like organoid in culture, comprising (a) culturing pluripotent stem cells to obtain neuronal lineage embryoid bodies; (b) culturing the neuronal lineage embryoid bodies from (a) to obtain midbrain regionalized tissues; (c) embedding and culturing the midbrain regionalized tissues from (b) in an extracellular matrix to obtain neuroepithelial tissues; and (c) culturing the neuroepithelial tissues from (c) to obtain a midbrain-like organoid. Also disclosed herein are culture media suitable for deriving and maintaining neuronal lineage embryoid bodies comprising (a) TGF-β Inhibitor and/or SMAD2/3 inhibitors; and (b) WNT-signaling activator; culture media suitable for deriving and maintaining midbrain regionalized tissues comprising (a) TGF-β Inhibitor and/or SMAD2/3 inhibitors; (b) WNT-signaling activator; (c) hedgehog signaling protein; and (d) fibroblast growth factor; culture media suitable for deriving and maintaining neuroepithelial tissues comprising (a) hedgehog signaling protein; and (b) fibroblast growth factor and culture media suitable for deriving and maintaining a midbrain-like organoid comprising (a) neurotrophin factor; (b) ascorbic acid; and (c) activator of cAMP-dependent pathway.

27 Claims, 30 Drawing Sheets
Specification includes a Sequence Listing.

(52) U.S. Cl.
    CPC ...... *C12N 2513/00* (2013.01); *C12N 2533/54* (2013.01); *C12N 2533/56* (2013.01); *C12N 2533/72* (2013.01); *C12N 2533/74* (2013.01); *C12N 2533/76* (2013.01); *C12N 2533/78* (2013.01); *C12N 2533/90* (2013.01)

(56) References Cited

U.S. PATENT DOCUMENTS

| | | | |
|---|---|---|---|
| 2016/0256495 | A1 | 9/2016 | Cho et al. |
| 2018/0298330 | A1* | 10/2018 | Bolognin ............ C12N 5/0622 |

FOREIGN PATENT DOCUMENTS

| | | | |
|---|---|---|---|
| WO | 2012168930 | A2 | 12/2012 |
| WO | 2013/163228 | A1 | 10/2013 |
| WO | 2014/090993 | A1 | 6/2014 |
| WO | 2015/016420 | A1 | 2/2015 |
| WO | 2015135893 | A1 | 9/2015 |
| WO | 2016141137 | A1 | 9/2016 |
| WO | 2017/060884 | A1 | 4/2017 |

OTHER PUBLICATIONS

Prakash et al. "Specification of midbrain territory." Cell and tissue research 318.1 (2004): 5-14 (Year: 2004).*

Kirkeby et al. "Generation of regionally specified neural progenitors and functional neurons from human embryonic stem cells under defined conditions." Cell reports 1.6 (2012): 703-714 (Year: 2012).*

PCT International Search Report and the Written Opinion of the International Searching Authority for International Application No. PCT/SG2017/050126, 9 pgs., (Jun. 9, 2017).

PCT International Preliminary Report on Patentability for International Application No. PCT/SG2017/050126, 10 pgs., (Sep. 18, 2018).

Arenas, "Wnt signaling in midbrain dopaminergic neuron development and regenerative medicine for Parkinson's disease," Journal of Molecular Cell Biology, 2014, vol. 6, pp. 42-53.

Arenas et al., "How to make a midbrain dopaminergic neuron," Development, May 26, 2015, vol. 142, No. 11, pp. 1918-1936.

Baizabal et al., "The embryonic midbrain directs neuronal specification of embryonic stem cells at early stages of differentiation," Dev. Biol., 2009, vol. 325, pp. 49-59.

Broccoli et al., "Modeling physiological and pathological human neurogenesis in the dish." Frontiers in Neuroscience, 2014, vol. 8, Article 183, 9 pgs.

Brustle, "Developmental neuroscience: Miniature human brains," Nature, 2014, vol. 501, pp. 319-320.

Bush et al., "The surface oxidation potential of human neuromelanin reveals a spherical architecture with a pheomelanin core and a eumelanin surface," Proceedings of the National Academy of Sciences of the United States of America, 2006, vol. 103, No. 50, pp. 14785-14789.

Carriel et al., "A novel histochemical method for a simultaneous staining of melanin and collagen fibers," The Journal of Histochemistry and Cytochemistry, 2011, vol. 59, No. 3, pp. 270-277.

Chambers et al., "Highly efficient neural conversion of human ES and IPS cells by dual inhibition of SMAD signaling." Nature Biotechnology, 2009, vol. 27, No. 3, pp. 275-280.

Chambers et al., "Build-a-brain," Cell Stem Cell, 2013, vol. 13, pp. 13377-13378.

Cherry et al. "Reprogrammed cells for disease modeling and regenerative medicine," Annual Review of Medicine, 2013, vol. 64, pp. 277-290.

The GTEx Consortium, "Human Genomics. The Genotype-Tissue Expression (GTEx) pilot analysis: Multitissue gene regulation in humans," Science, 2015, vol. 348, pp. 648-660.

Fedorow et al., "Neuromelanin in human dopamine neurons: comparison with peripheral melanins and relevance to Parkinson's disease," Progress in Neurobiology, 2005, vol. 75, pp. 109-124.

Ferrari et al., "Midbrain dopaminergic neurons generate calcium and sodium currents and release dopamine in the striatum of pups," Frontiers in Cellular Neuroscience, 2012, vol. 6, Article 7, 9 pgs.

Gentleman et al., "Bioconductor: open software development for computational biology and bioinformatics," Genome Biol., 2004, vol. 5, Issue 10, Article R80, 16 pgs.

Grealish et al., "Human ESC-derived dopamine neurons show similar preclinical efficacy and potency to fetal neurons when grafted in a rat model of Parkinson's disease," Cell Stem Cell, 2014, vol. 15, pp. 653-665.

Hallett et al., "Successful function of autologous iPSC-derived dopamine neurons following transplantation in a non-human primate model of Parkinson's disease," Cell Stem Cell, 2015, vol. 16, pp. 269-274.

Hartley et al., "Dopaminergic differentiation of schizophrenia hiPSCs," Mol. Psychiatry, 2015, vol. 20, No. 5, pp. 549-550.

Jaffe et al., "Developmental regulation of human cortex transcription and its clinical relevance at single base resolution," Nature Neuroscience, 2015, vol. 18, No. 1, pp. 154-161.

Thomson et al., "Embryonic Stem Cell Lines Derived from Human Blastocysts," Science, 1998, vol. 282, 1145-1147.

Jo et al., "Midbrain-like Organoids from Human Pluripotent Stem Cells Contain Functional Dopaminergic and Neuromelanin-Producing Neurons," Cell Stem Cell, 2016, vol. 19, No. 2, pp. 248-257.

Kim et al., "TopHat2: accurate alignment of transcriptomes in the presence of insertions, deletions and gene fusions," Genome Biol., 2013, vol. 14, Article R36, 13 pgs.

Kim et al., "Immobilization stress causes increases in tetrahydrobiopterin, dopamine, and neuromelanin and oxidative damage in the nigrostriatal system," J. Neurochem. 2013, vol. 95, pp. 89-98.

Kirkeby et al., "Generating regionalized neuronal cells from pluripotency, a step-by-step protocol," Frontiers in Cellular Neuroscience, 2013, vol. 6, Article 64, 4 pgs.

Kirkeby et al., "Generation of Regionally Specified Neural Progenitors and Functional Neurons from Human Embryonic Stem Cells under Defined Conditions," Cell Reports, 2012, vol. 1, No. 6, pp. 703-714.

Kriks et al., "Floor plate-derived dopamine neurons from hESCs efficiently engraft in animal models of PD." Nature, 2012, vol. 480, pp. 547-551.

Lancaster et al., "Organogenesis in a dish; modeling development and disease using organoid technologies," Science, 2014, vol. 345, Issue 6194, 1247125-1-1247125-9, 11 pgs.

Lancaster et al., "Cerebral organoids model human brain development and microcephaly," Nature, 2013, vol. 501, No. 7467, pp. 373-379.

Lancaster et al., "Generation of cerebral organoids from human pluripotent stem cells," Nature Protocols, 2014, vol. 9, No. 10, pp. 2329-2340.

Lawrence et al., "Software for computing and annotating genomic ranges," PLoS Computational Biology, 2013, vol. 9, Issue 8, 10 pgs.

Lei et al., "A fully defined and scalable 3D culture system for human pluripotent stem cell expansion and differentiation," Proc. Natl. Acad. Sci. USA, 2013, vol. 110, No. 52, pp. E5039-E5048.

Lin et al., "Molecular Features Underlying Neurodegeneration Identified through In Vitro Modeling of Genetically Diverse Parkinson's Disease Patients," Cell Reports, 2016, vol. 15, pp. 2411-2426.

Love et al., "Moderated estimation of fold change and dispersion for RNA-seq data with DESeq2," Genome Biology, 2014, vol. 15, No. 550, 21 pgs.

Mariani et al., "FOXG1-Dependent Dysregulation of GABA/Glutamate Neuron Differentiation in Autism Spectrum Disorders," Cell, 2015, vol. 162, No. 2, pp. 375-390.

Muguruma et al., "Self-organization of polarized cerebellar tissue in 3D culture of human pluripotent stem cells," Cell Reports, 2015, vol. 10, 537-550.

Nighswander-Rempel et al., "Quantitative fluorescence excitation spectra of synthetic eumelanin," The Journal of Physical Chemistry, 2005, vol. 109, No. 43, pp. 20629-20635.

(56) References Cited

OTHER PUBLICATIONS

Pasca et al., "Functional cortical neurons and astrocytes from human pluripotent stem cells in 3D culture," Nat. Methods, 2015, vol. 12, No. 7, pp. 671-678.
Sasai, "Cytosystems dynamics in self-organization of tissue architecture," Nature, 2013, vol. 493, pp. 318-326.
Sasai "Next-generation regenerative medicine: organogenesis from stem cells in 3D culture," Cell Stem Cell, 2013, vol. 12, pp. 520-530.
Sulzer et al., "Neuromelanin biosynthesis is driven by excess cytosolic catecholamines not accumulated by synaptic vesicles," Proc. Natl. Acad. Sci. USA, 2000, vol. 97, No. 22, pp. 11869-11874.
Tabar et al., "Pluripotent stem cells in regenerative medicine: challenges and recent progress," Nat. Rev. Genet., 2014, vol. 15, pp. 82-92.
The R Development Core Team, R: A Language and Environment for Statistical Computing, Reference Index, Feb. 8, 2008, Version 2.6.2.
Tieng et al., "Engineering of Midbrain Organoids Containing Long-Lived Dopaminergic Neurons," Stem Cells Dev., 2014, vol. 23, No. 13, pp. 1535-1547.
Vernay et al., "Otx2 regulates subtype specification and neurogenesis in the midbrain. The Journal of Neuroscience," The Journal of Neuroscience, 2005, vol. 25, No. 19, pp. 4856-4867.
Viceconte et al., "Neuromelanin activates proinflammatory microglia through a caspase-8-dependent mechanism," Journal of Neuroinflammation, 2015, vol. 12, 15 pgs.
Wickham, In Re: ggplot2: elegant graphics for data analysis, Springer, New York, NY, 2009.
Yamanaka, "Strategies and new developments in the generation of patient-specific pluripotent stem cells," Cell Stem Cell, 2007, vol. 1, pp. 39-49.
Yin et al., "Engineering Stem Cell Organoids," Cell Stem Cell, 2016, vol. 18, No. 1, pp. 25-38.
Yuan et al., "Regulation of Brain-Derived Neurotrophic Factor Exocytosis and Gamma-Aminobutyric Acidergic Interneuron Synapse by the Schizophrenia Susceptibility Gene Dysbindin-1." Biol. Psychiatry, 2016, vol. 80, pp. 312-322.
Zecca et al., "The absolute concentration of nigral neuromelanin, assayed by a new sensitive method, increases throughout the life and is dramatically decreased in Parkinson's disease," FEBS Letters, 2002, vol. 510, pp. 216-220.
Zecca et al., "New melanic pigments in the human brain that accumulate in aging and block environmental toxic metals," Proc. Natl. Acad. Sci, USA, 2008, vol. 105, No. 45, pp. 17567-17572.
Kelava et al., "Dishing out mini-brains: Current progress and future prospects in brain organoid research", Elsevier, Jul. 9, 2016, 12 pages.
The Extended European Search Report for the counterpart European Application No. 17767082.5, dated Jan. 22, 2020, 9 pages.
Qian et al., "Brain-Region-Specific Organoids Using Mini-bioreactors for Modeling ZIKV Exposure", Cell, Apr. 22, 2016, 18 pages.
Sonja Kriks et al., "Dopamine neurons derived from human ES cells efficiently engraft in animal models of Parkinson's disease," Nature, vol. 480, Dec. 22-29, 2011, 7 pages.
European Search Report, dated Nov. 25, 2019, issued in connection with European Patent Application No. 17767082.5, 8 pages.
Office Action, dated Nov. 29, 2021, issued in connection with European Patent Application No. 17767082.5, 4 pages.
Office Action, dated Jun. 9, 2021, issued in connection with European Patent Application No. 17767082.5, 3 pages.
Office Action, dated Jul. 8, 2022, issued in connection with Chinese Patent Application No. 201780029142.2 [original document in Chinese and English language translation], 14 pages.
Office Action, dated Dec. 22, 2022, issued in connection with Chinese Patent Application No. 201780029142.2 [original document in Chinese and English language translation], 13 pages.
Office Action, dated Jul. 31, 2023, issued in connection with Chinese Patent Application No. 201780029142.2 [original document in Chinese and English language translation], 16 pages.

* cited by examiner

C

Decreased expression in hMLO vs 2D-DA neuron    p=2.21e-248    Decreased expression in Prenatal midbrain vs 2D-DA neuron Increased expression in hMLO vs 2D-DA neuron    Increased expression in Prenatal midbrain vs 2D-DA neuron p=4.13e-313

D

Genes ranked by log2 fold change

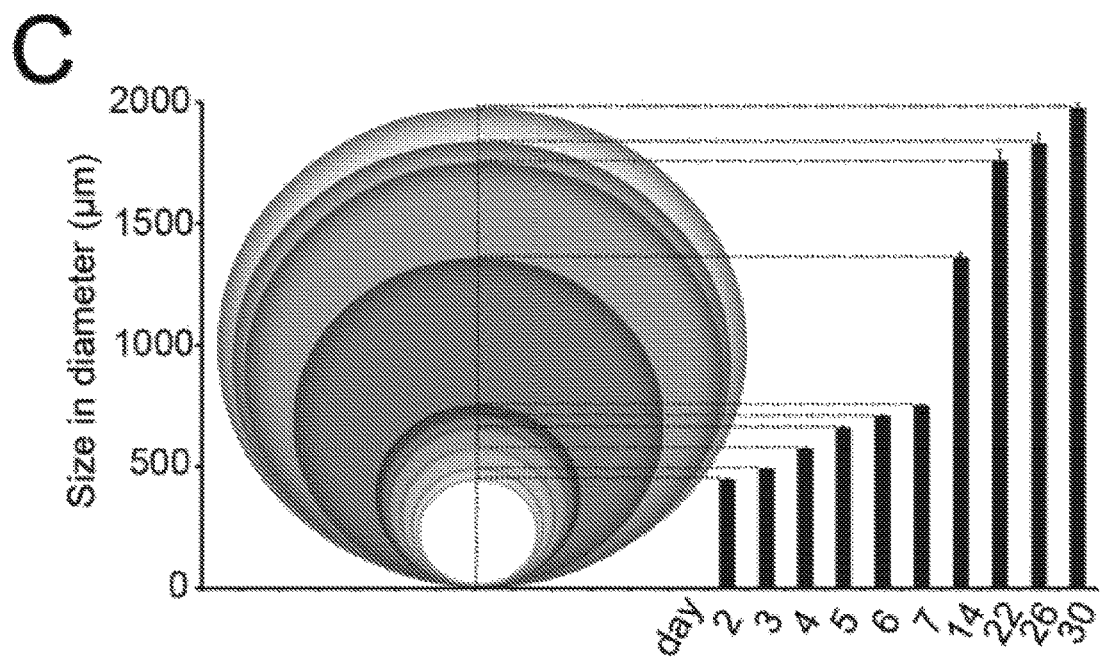
FIG. 5 continued
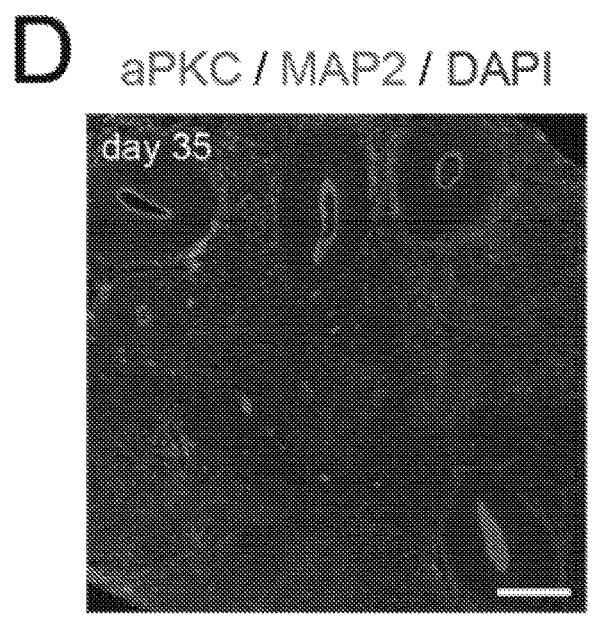
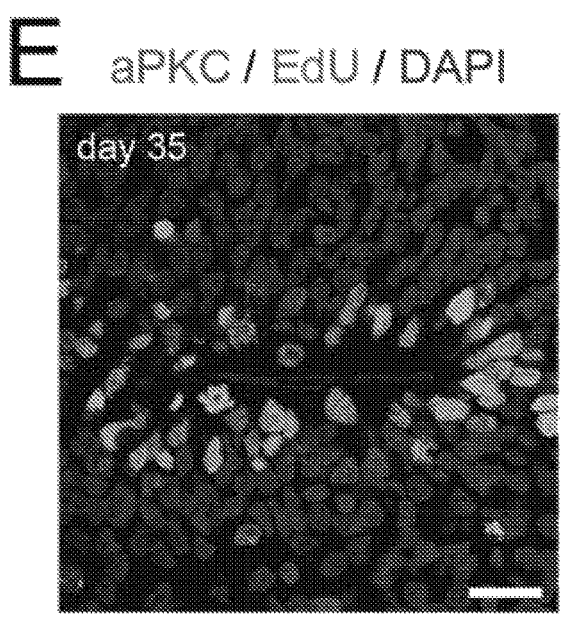

M

N

C Cerebral organoid — Fontana-Masson

D AFM deflection image of NM granules

E AFM height image of NM granules

GENERATION OF MIDBRAIN-SPECIFIC ORGANOIDS FROM HUMAN PLURIPOTENT STEM CELLS

CROSS-REFERENCE TO RELATED APPLICATIONS

This patent application is a U.S. National Phase Application under 35 U.S.C. § 371 of International Application No. PCT/SG2017/050126, filed on 14 Mar. 2017, entitled GENERATION OF MIDBRAIN-SPECIFIC ORGANOIDS FROM HUMAN PLURIPOTENT STEM CELLS, which claims the benefit of priority of Singapore provisional application No. 10201601965P, filed on 14 Mar. 2016, the contents of it were incorporated by reference in the entirety for all purposes.

INCORPORATION BY REFERENCE

This patent application incorporates by reference the material (i.e., Sequence Listing) in the ASCII text file named Sequence_Listing_4587958_1.TXT, created on Sep. 12, 2018 (modified Aug. 30, 2018), having a file size of 21,831 bytes.

FIELD OF THE INVENTION

The present invention relates generally to the field of biotechnology. In particular, the present invention relates to methods of generating organoids.

BACKGROUND OF THE INVENTION

Restricted access to functional human brain tissue is the greatest challenge to understand the development of the human nervous system and its dysfunction in brain disorders. Recently, this challenge is being surmounted by rapid research progress on human pluripotent stem cells (hPSCs), which include for example, embryonic stem cells (hESCs) and induced pluripotent stem cells (iPSCs), which can be generated from any individual and can be directed to differentiate in vitro into derivatives representing all germ layers, including neuronal cells. Over past decades, differentiation protocols of human pluripotent stem cells into neurons were solely based on two-dimensional (2D) methods under conditions, which are unable to recapitulate cytoarchitecture of the developing three-dimensional (3D) nervous system or the complexity and functionality of in vivo neural circuits in their entirety. Previous reports demonstrated the generation of infant brain to be suitable for studying developmental disorders. However, the generation of mature brain organoids is remains challenging.

Due to growing interest in regenerative medicine and in the identification of the mechanisms underlying diseases affecting midbrain dopaminergic (mDA) neurons generating midbrain dopaminergic neurons from human pluripotent stem cells has been an intense area of research. However, it has mostly yielded midbrain dopaminergic neurons using conventional 2D methods. While these studies definitely advance the field, it is still not clear whether a 3D organoid model for a midbrain can be developed.

Therefore, there is a need for the development of a 3D system for generating organoid cultures of brain parts, for example, cortical organoids, telencephalic organoids, and cerebellar tissue.

SUMMARY

In one aspect, the present invention refers to a method of deriving and maintaining a midbrain-like organoid comprising (a) culturing pluripotent stem cells to obtain neuronal lineage embryoid bodies; (b) culturing the neuronal lineage embryoid bodies from (a) to obtain midbrain regionalized tissues; (c) embedding and culturing the midbrain regionalized tissues from (b) in an extracellular matrix to obtain developing neuroepithelial tissues; and culturing the neuroepithelial tissues from (c) to obtain a midbrain-like organoid.

In another aspect, the present invention refers to an isolated midbrain-like organoid obtained by the method as disclosed herein.

In yet another aspect, the present invention refers to a culture medium for deriving and maintaining neuronal lineage embryoid bodies comprising (a) TGF-β inhibitor and/or SMAD2/3 inhibitor; and (b) WNT-signalling activator.

In a further aspect, the present invention refers to a culture medium for deriving and maintaining midbrain regionalized tissues, comprising (a) TGF-β inhibitor and/or SMAD2/3 inhibitor; (b) WNT-signalling activator; (c) hedgehog signalling protein; and (d) fibroblast growth factor.

In yet another aspect, the present invention refers to a culture medium for deriving and maintaining developing neuroepithelial tissues, comprising (a) hedgehog signalling protein; and (b) fibroblast growth factor.

In a further aspect, the present invention refers to a culture medium for deriving and maintaining a midbrain-like organoid, comprising (a) neurotrophic factor; (b) ascorbic acid; and (c) activator of cAMP-dependent pathways.

BRIEF DESCRIPTION OF THE DRAWINGS

The invention will be better understood with reference to the detailed description when considered in conjunction with the non-limiting examples and the accompanying drawings, in which.

Rebound depolarization is characterized by transient depolarization following hyperpolarizing pulses, which is unique to substantia nigra dopaminergic neurons due to the presence of unique ion channels. Insets show enlarged view of respective traces. (K) shows a representative trace of pacemaker-like firing and the effect of Quinpirole on firing frequency. The statistical analysis of the phenomenon shown in (K) is provided in the column graphs shown in (L) (*p=0.021, paired t-test, n=3). (M) shows micrographs of a tyrosine hydroxylase (TH) immunostaining of a neuron filled with biocytin during recording, indicating that the recorded neuron expressed TH. Scale bar=5 µm. (N) Dopamine measurement in human midbrain-like organoids (hMLOs) and human cerebral organoids (hCOs) by high performance liquid chromatography (HPLC) [hMLO 4 w, 5 w, 7 w, and 9 w (n=4); hMLO 13 w, hCO 7 w and 27 w, with w indicating weeks (n=3)].

Figure 5:
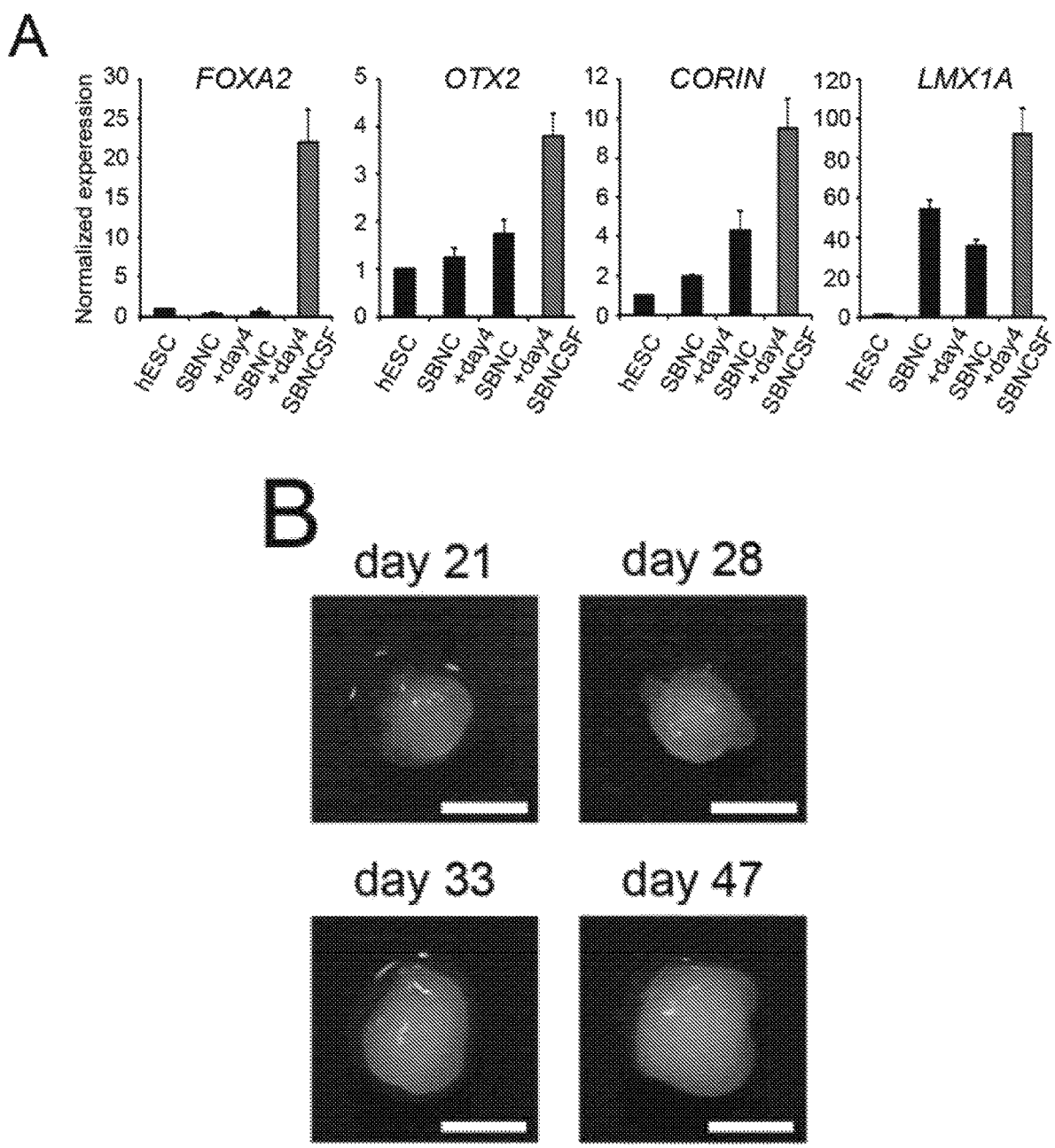
Figure 5:
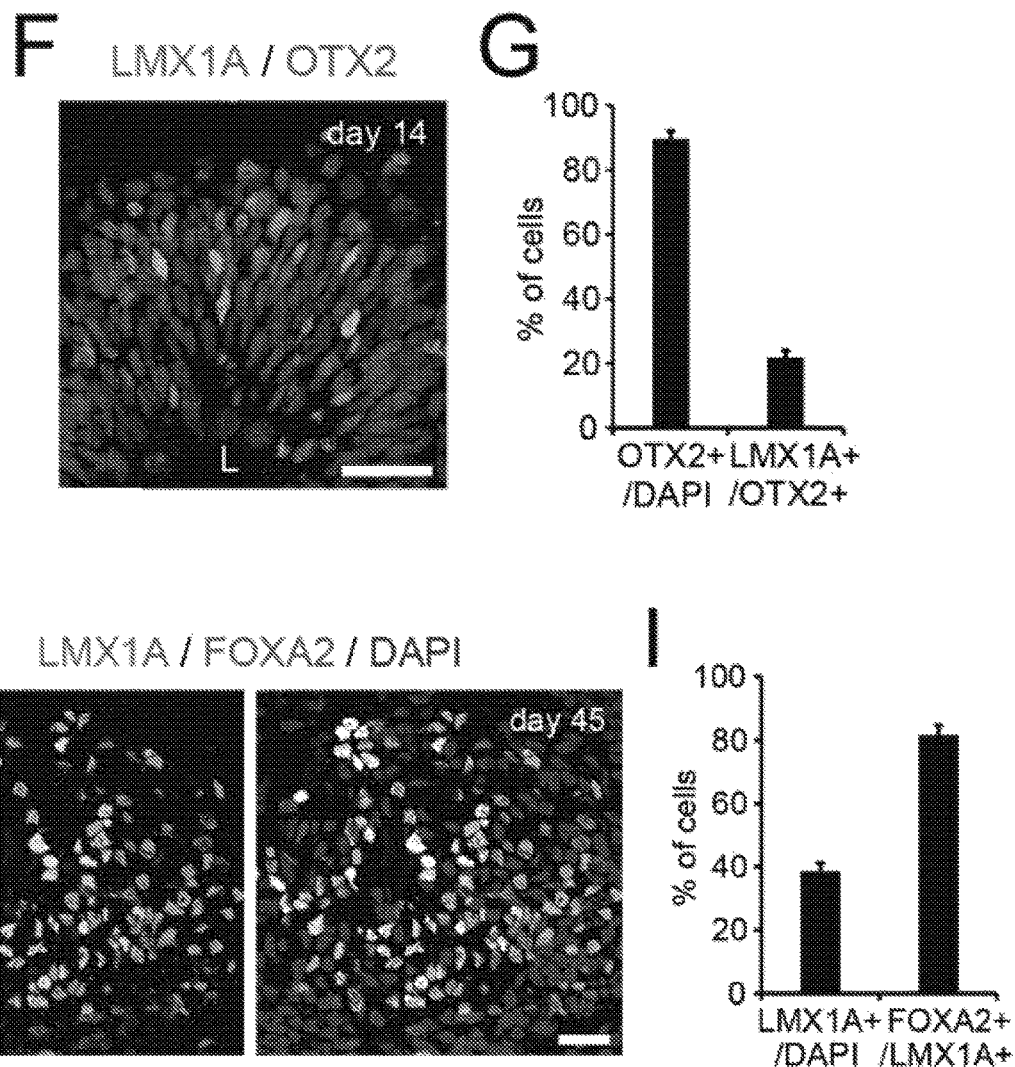
Figure 5:
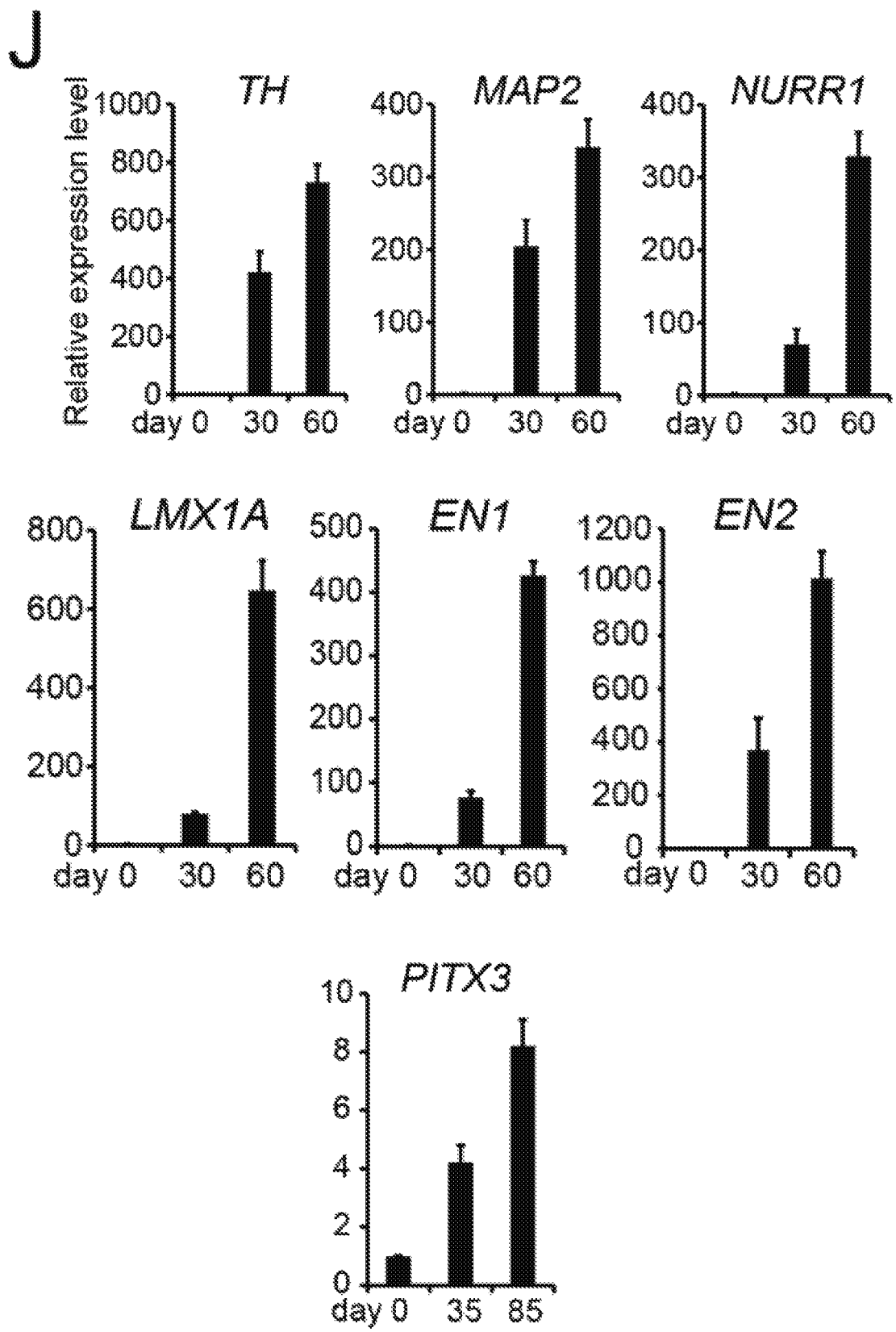
Figure 5:
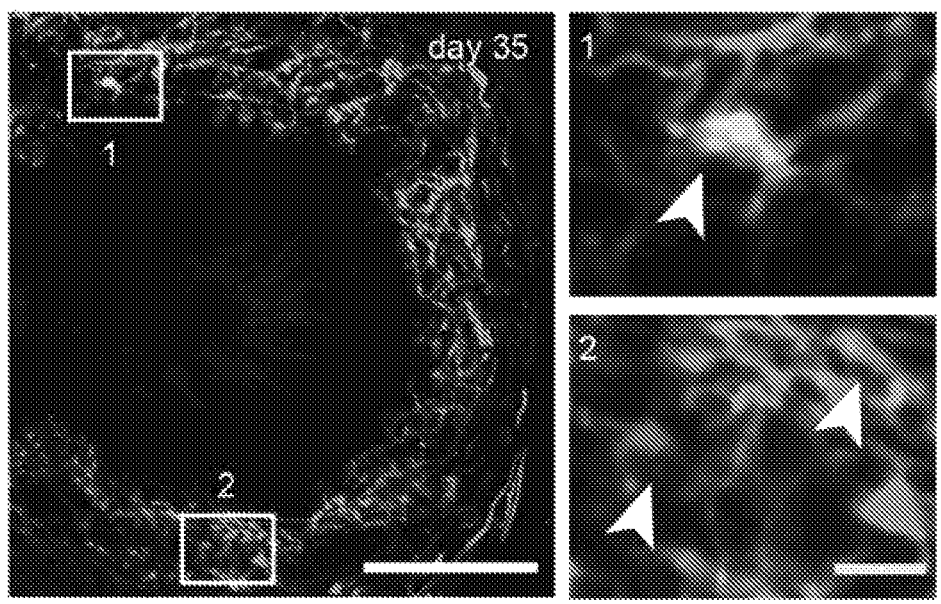
Figure 5:
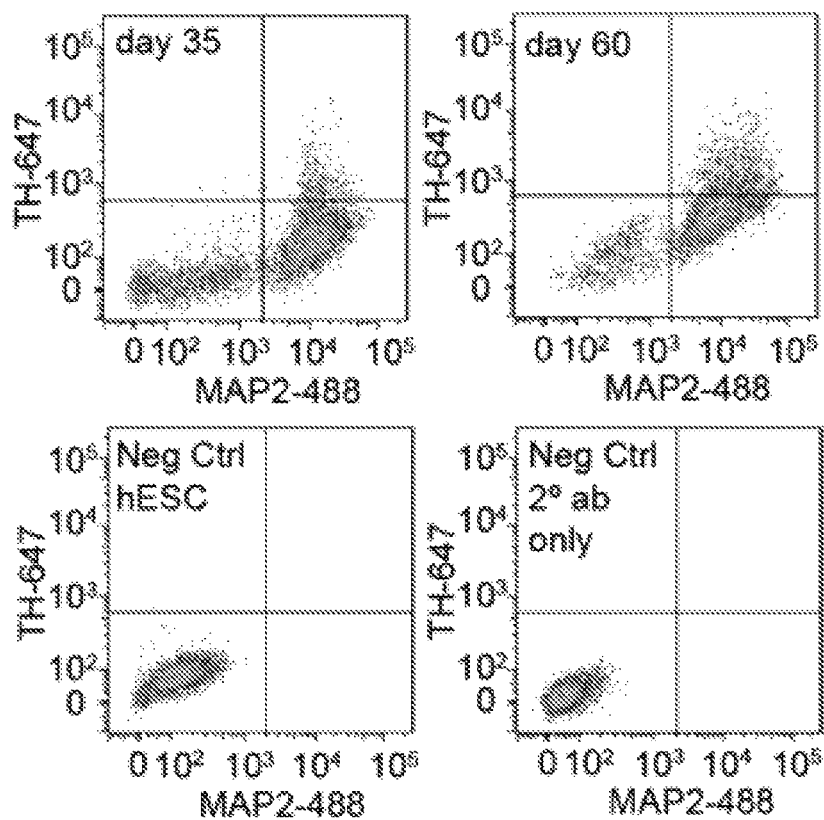
Figure 5:
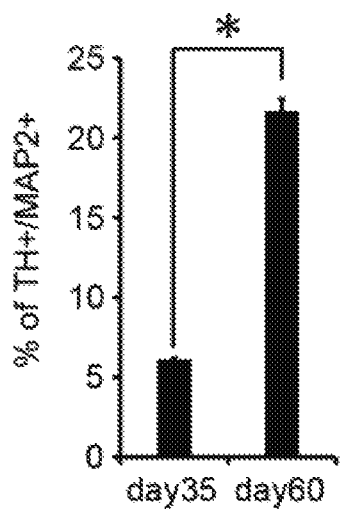
Figure 5:
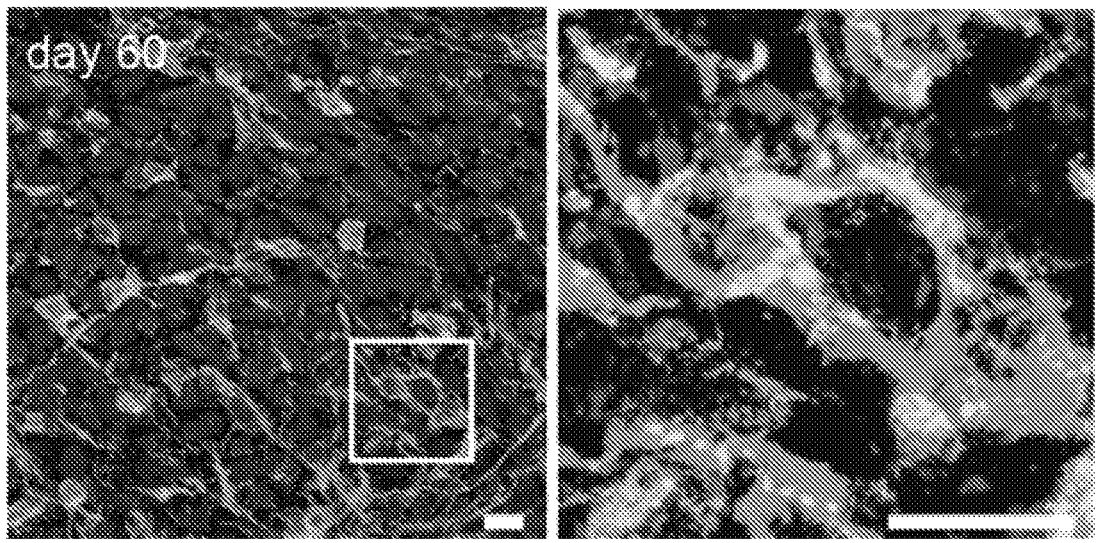
Figure 5:
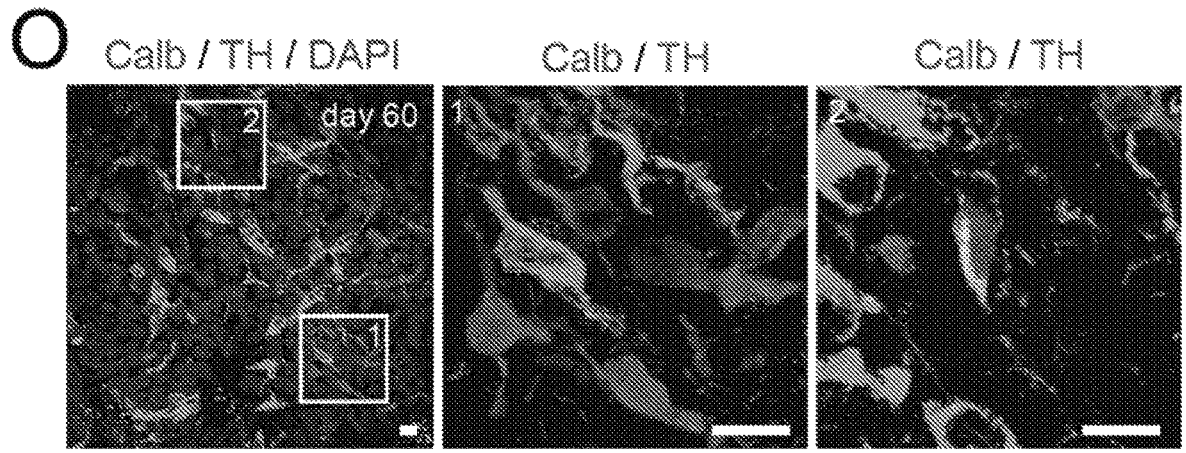

FIG. 5 shows the results of the Characterization of human midbrain-like organoids (hMLOs), as well as the characterization of midbrain dopaminergic (mDA) neurons in human midbrain-like organoids (hMLOs). (A) shows column graphs depicting the results of quantitative reverse transcriptase polymerase chain reaction (qRT-PCR), also known as real-time reverse transcriptase PCR. analysis of cells dissociated from either human embryonic stem cells (hESCs) or human midbrain-like organoids (hMLOs) treated with SBNC (SB431542, Noggin, and CHIR99021) or SBNC+SF (SHH-C25II and FGF8) for FOXA2, OTX2, CORIN, and LMX1A (midbrain progenitor markers). (B) shows differential interference contrast (DIC) images illustrating the typical morphology of human midbrain-like organoids at each stage as indicated at the top of the respective images. Scale bar=2 mm. (C) shows a circle diagram showing the growth rates of human midbrain-like organoids at each stage as indicated to the right of the diagram (D) shows micrograph images of a cryosection of an human midbrain-like organoid at day 35 stained for aPKC and MAP2. It is noted that multiple round shaped rosettes were present in the human midbrain-like organoid. Scale bar=200 µm. (E) shows a micrograph of a cryosection of a human midbrain-like organoid at day 35 stained for aPKC and EdU, showing that proliferating EdU-positive cells were located at the apical surface of a neuroepithelium. Scale bar=20 µm. (F) shows a micrograph of a cryosection of a day 14 human midbrain-like organoid labelled for LMX1A and OTX2. The quantification of the staining shown in (F) are presented in the column graphs shown in (G); mean±s.e.m. (standard error of the mean), n=3. Scale bars=50 µm. (H) shows micrograph images of cryosections of a human midbrain-like organoid at day 45 that was stained for LMX1A and FOXA2. Scale bars=20 µm. The quantification of the stainings shown in (H) are shown in the column graphs presented in (I); mean±s.e.m. (standard error of the mean), n=3. (J) shows the results of quantitative reverse transcriptase polymerase chain reaction (qRT-PCR) (also known as real-time reverse transcriptase PCR) analysis of cells dissociated from hMLOs for TH, MAP2, NURR1, LMX1A, EN1, EN2, and PITX3, each presented in a column graph. (K) shows micrograph images of tyrosine hydroxylase (TH)-positive neurons located in the MZ at day 35. Left scale bar=100 µm. Right scale bar=10 µm. Arrowheads indicate TH and MAP2 double-positive cells. (L) shows the results of the flow cytometric analysis of cells dissociated from human midbrain-like organoids at day 35 and day 60, presented as scatter plots. (M) shows the quantification of the percentage of midbrain dopaminergic (mDA) neurons (TH+/MAP2+) present in (L), revealing a significant increase at day 60; mean±s.e.m. (standard error of the mean), n=3. Bottom left of (L): flow cytometry analysis of human embryonic stem cells (hESC) cells stained for both primary and secondary antibodies. Bottom right of (L): flow cytometry analysis of human midbrain-like organoid-derived cells stained only with secondary antibodies. Threshold gate is based on the both negative control that used to quantify the percentage of cells expressing TH and MAP2. (N) shows micrograph images of G protein-activated inward rectifier potassium channel 2 (GIRK2) and tyrosine hydroxylase (TH) double-positive neurons within the mantle zone (MZ) of a day 60 human midbrain-like organoid, including a higher-magnification view to better illustrate the co-localization. Scale bar=10 µm. (O) shows micrograph images of cryosections of a human midbrain-like organoid at day 60 immunostained for tyrosine hydroxylase (TH) and Calbindin (Calb, a marker for A10 subtype of dopaminergic (DA) neurons), including a higher-magnification view of the white boxes of the left most panel to illustrate cells that were positive for either TH or Calb (1) and cells were double positive for both TH and Calb (2). Scale bar=10 µm.

Figure 6:
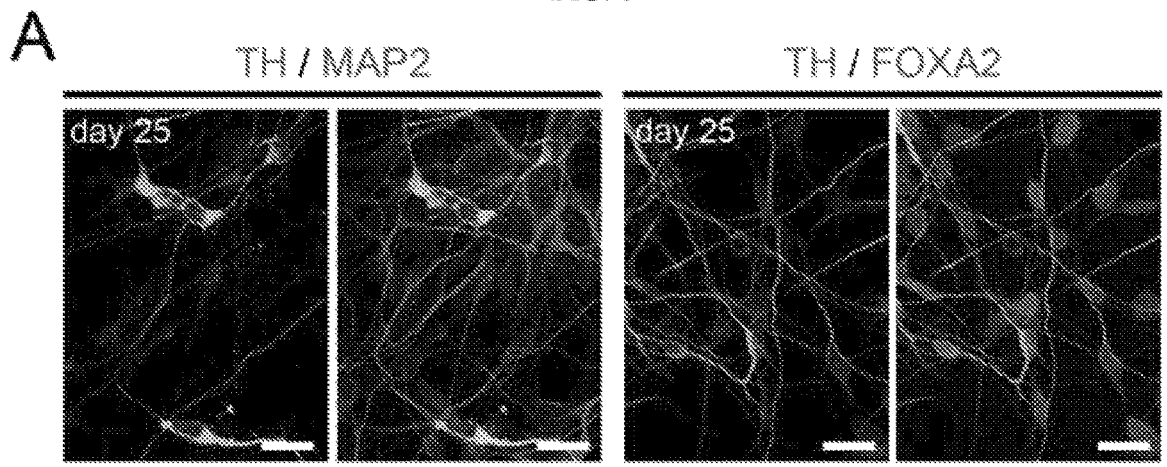
Figure 6:
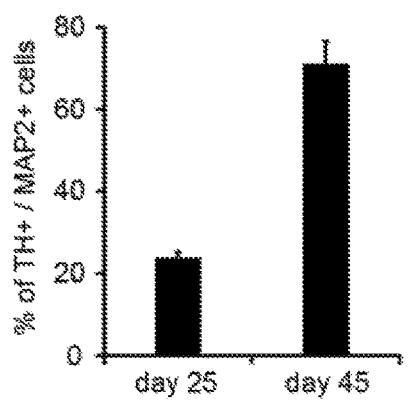
Figure 6:
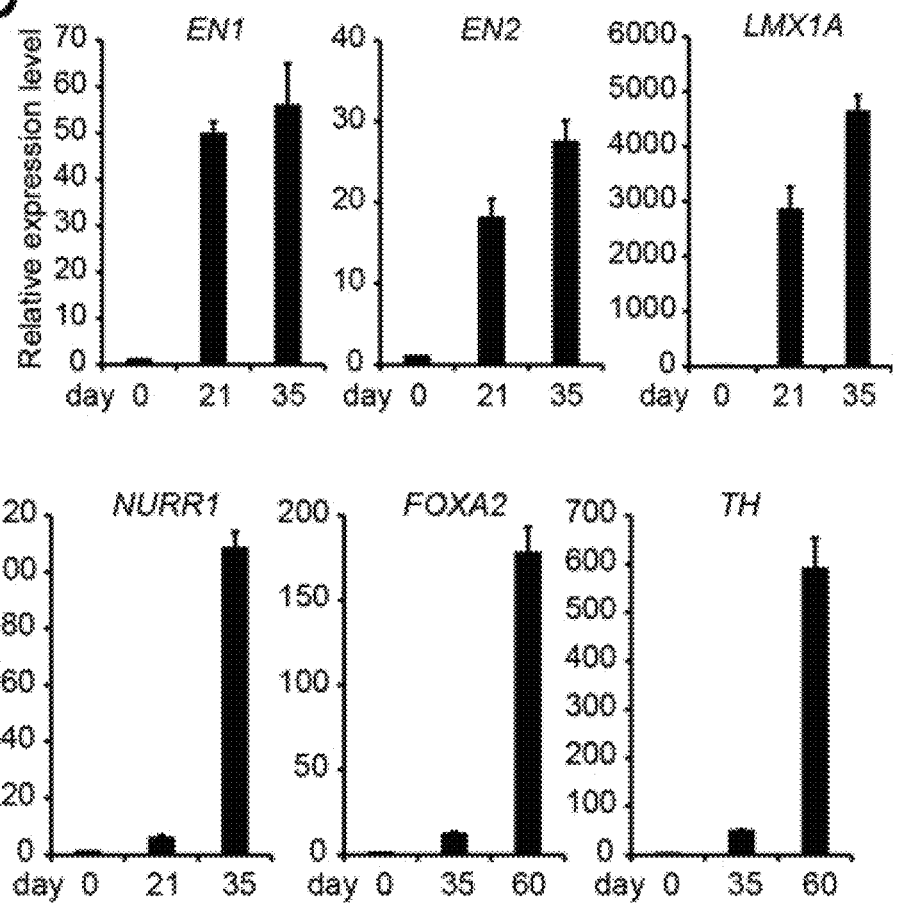
Figure 6:
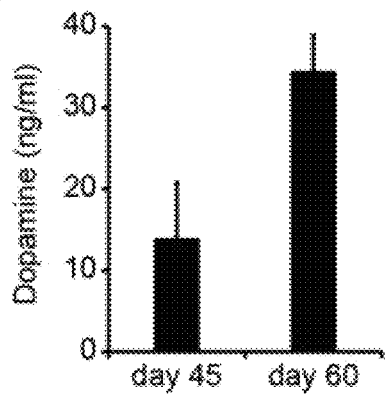
Figure 6:
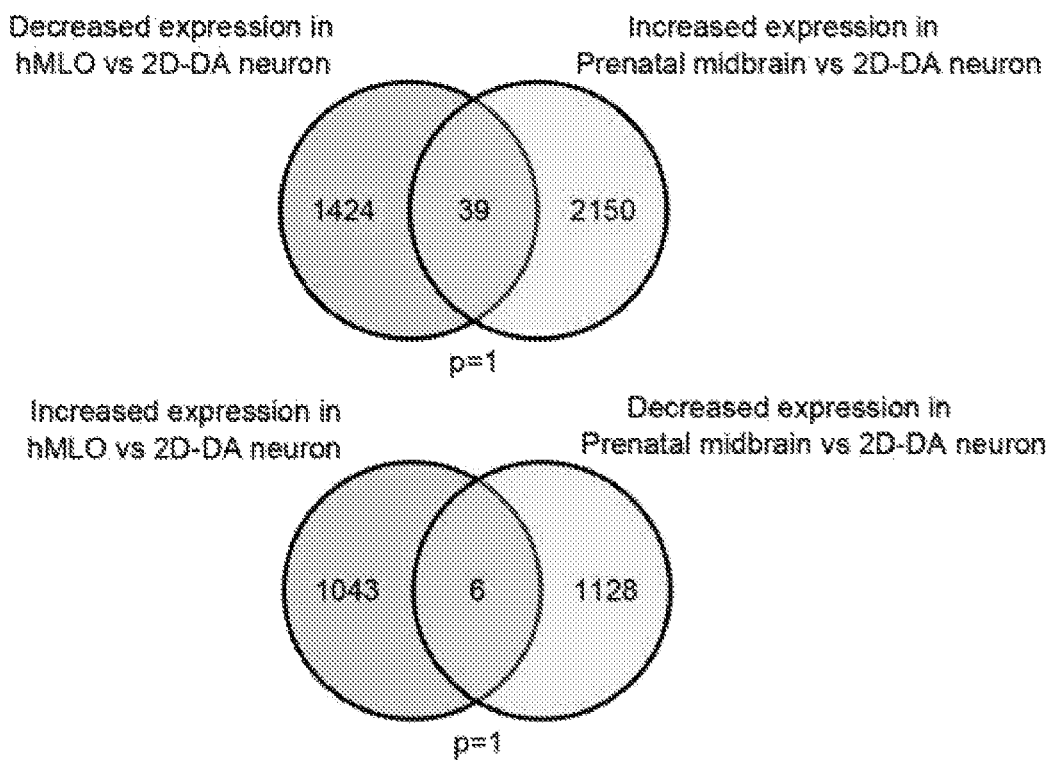
Figure 6:
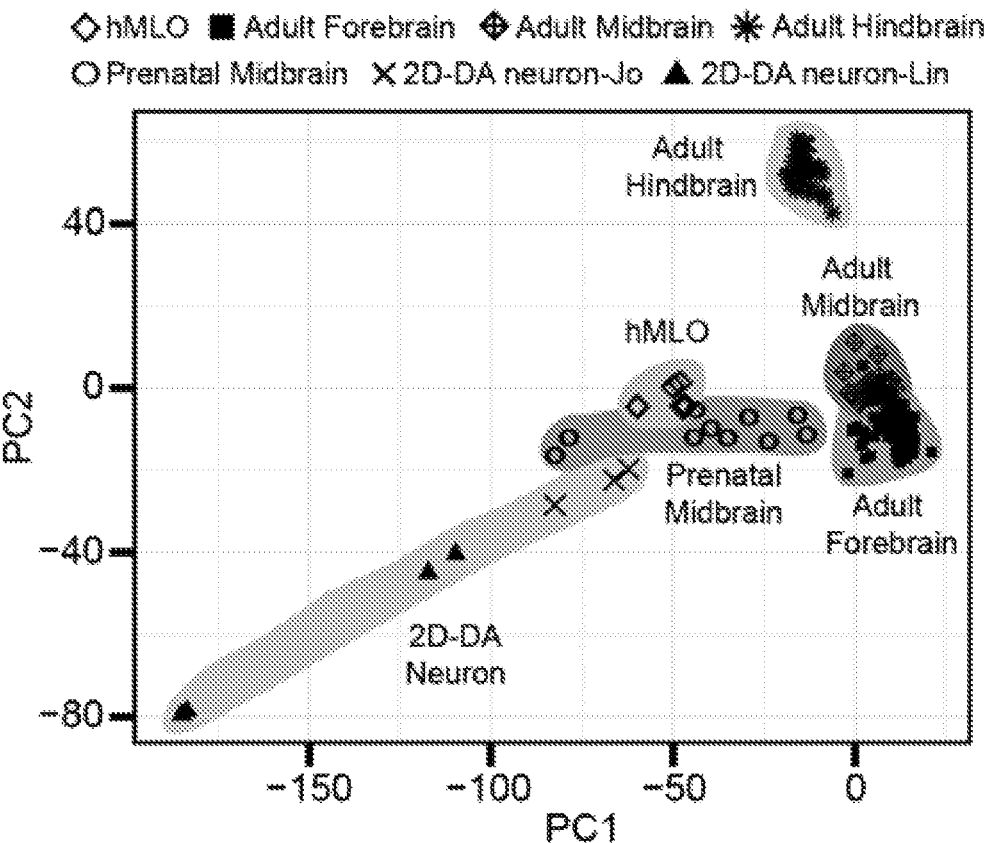
Figure 6:
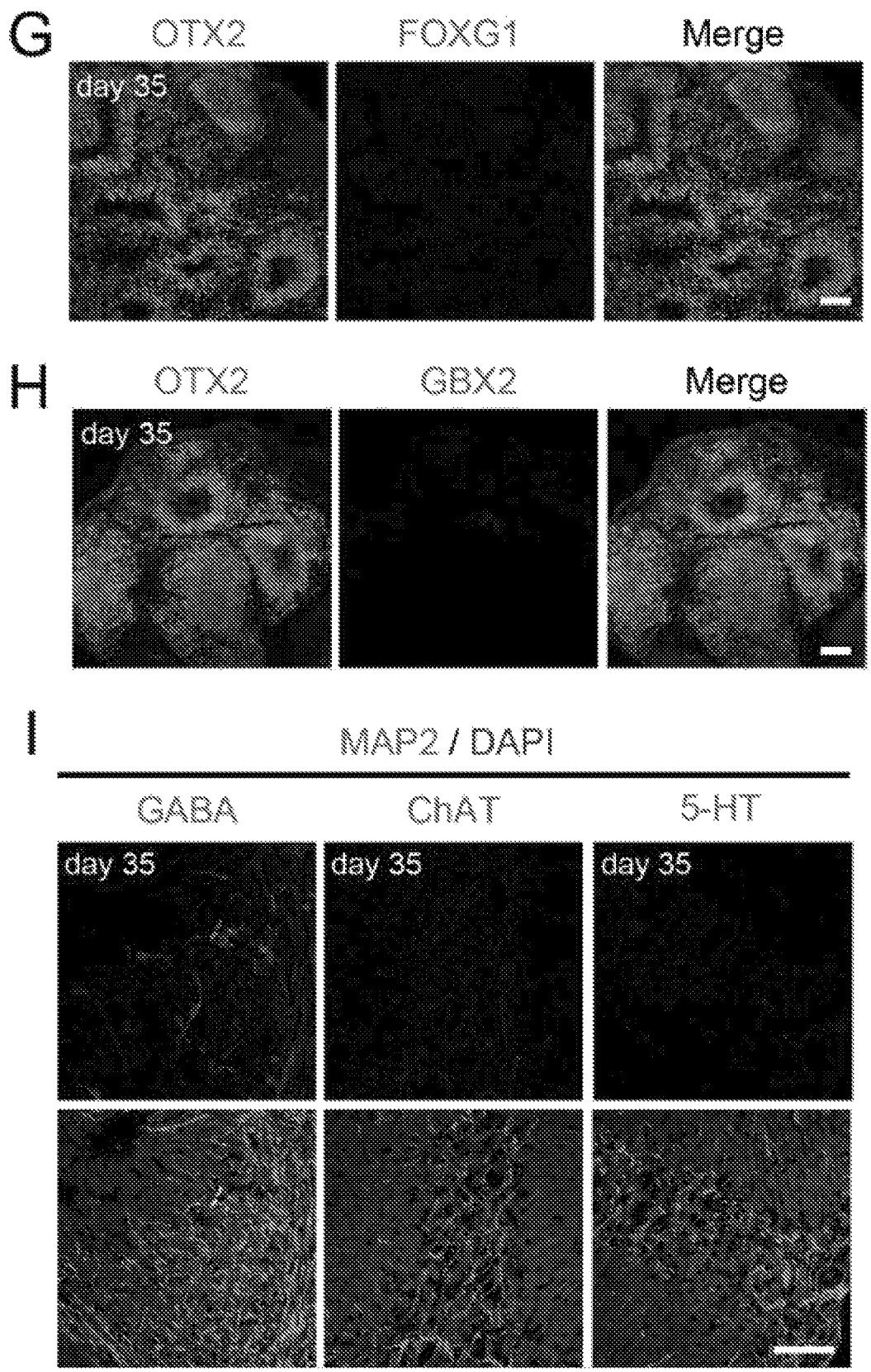

FIG. 6 shows the results of the characterization of 2D-DA neuron, (A-D) the transcriptional characterization of human midbrain-like organoids (hMLOs) (E-F), and the regional and cellular identity of human midbrain-like organoids (hMLOs; G-I). (A) shows micrographs of the immunostaining of day 25 two-dimensional dopaminergic (2D-DA) neurons for dopaminergic (DA) neuron markers tyrosine hydroxylase (TH) and FOXA2. (B) shows a column graph depicting the quantification of TH+/MAP2+ cells at day 25 and 45; mean±s.e.m. (standard error of the mean), n=5. Scale bar=20 µm. (C) shows column graphs depicting the results of quantitative reverse transcriptase polymerase chain reaction (qRT-PCR) (also known as real-time reverse transcriptase PCR) analysis of 2D-DA neurons for, EN1, EN2, LMX1A, NURR1, FOXA2, and TH, whereby the results for each marker are shown in their own column graph. (D) shows a column graph presenting the dopamine content measured in 2D-DA neurons by high performance liquid chromatography (HPLC) (n=3). (E) shows Venn diagrams indicating the overlap of upregulated and downregulated genes in human midbrain-like organoids and prenatal midbrain, compared to 2D-grown human dopaminergic (DA) neurons. (Statistical significance was estimated using Fisher's exact test; in relation to FIG. 2C). (F) shows the results of a principal component analysis (PCA) of the RNA sequencing (RNA-Seq) data from adult forebrain, adult hindbrain, adult midbrain, prenatal midbrain, human midbrain-like organoids, and 2D-DA neurons (2D-DA neuron-1: data not shown RNA-seq data; 2D-DA neuron-2: RNA-seq data based on (Lin et al., 2016). The PCA was calculated using the top 1,000 genes with the highest variance in normalised read counts across all samples (regularized log transformation). Histone genes were removed for this analysis. (G) shows micrographs of cryosections of a human midbrain-like organoid at day 35 that was stained for OTX2 (midbrain marker) and FOXG1 (forebrain marker). Scale bar=100 µm. (H) shows micrographs of cryosections of a human midbrain-like organoid at day 35 stained for OTX2 and GBX2 (hindbrain marker). (I) shows micrographs of cryosections of a human midbrain-like organoid at day 35 that were stained for GABA (GABAergic neuronal marker), ChAT (cholinergic neuronal marker), and 5-HT (serotonergic neuronal marker). Scale bar=50 µm.

Figure 7:
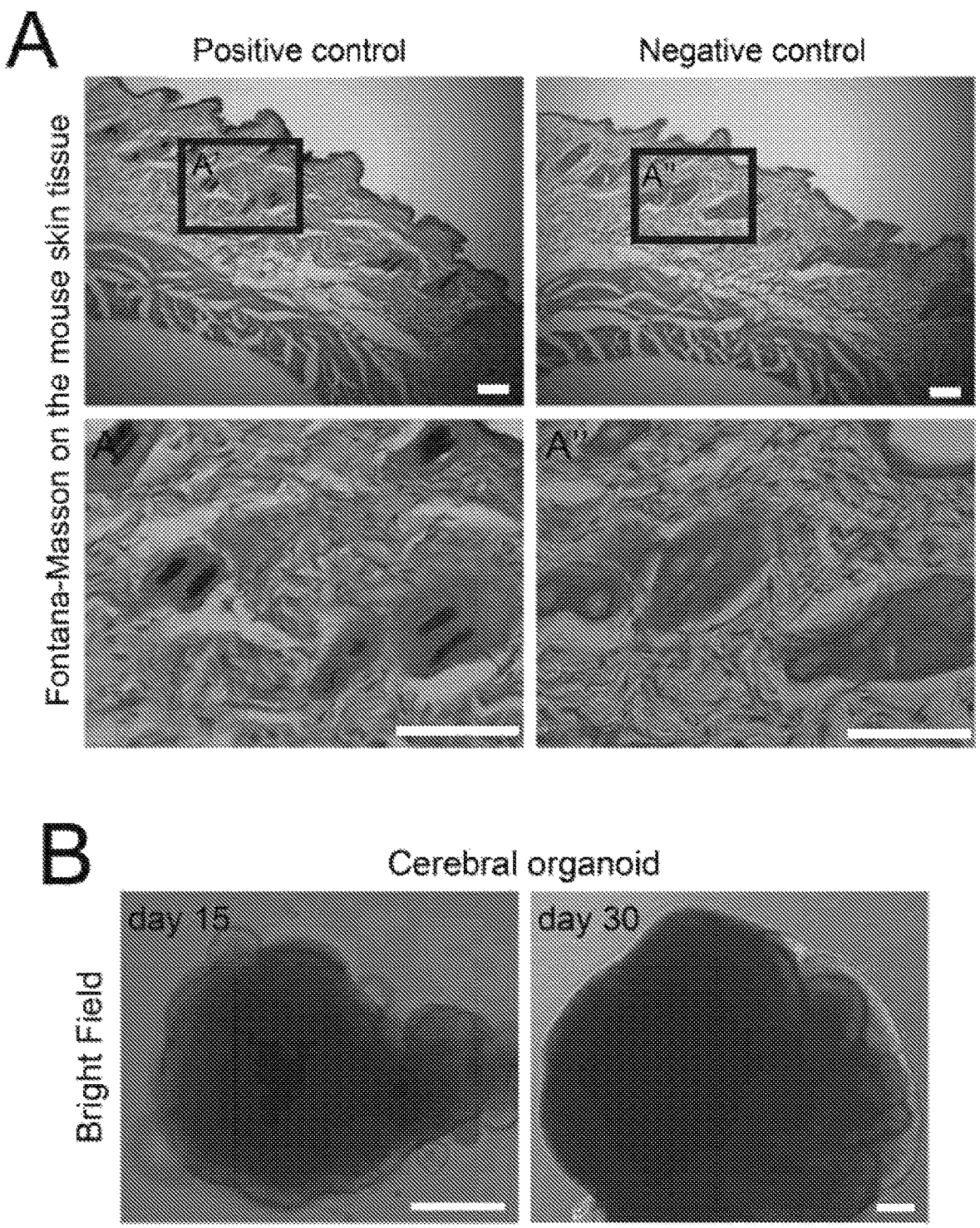
Figure 7:
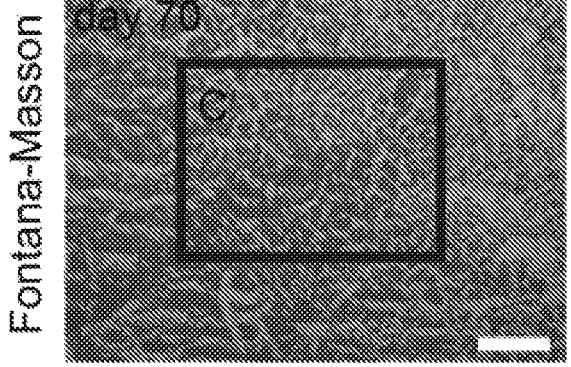
Figure 7:
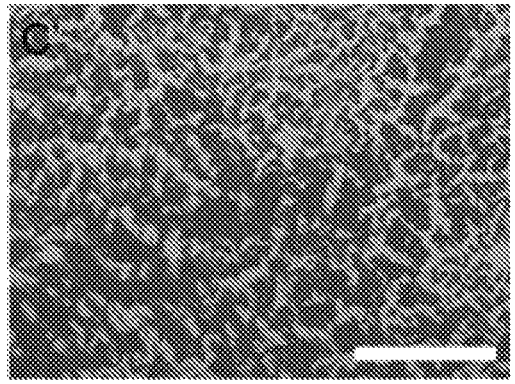
Figure 7:
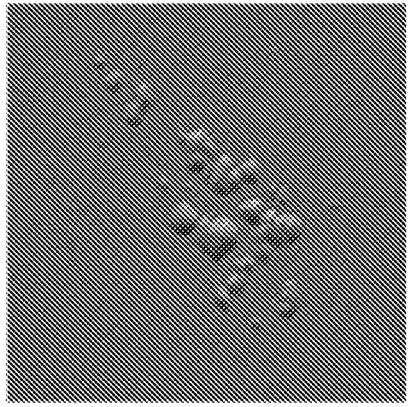
Figure 7:
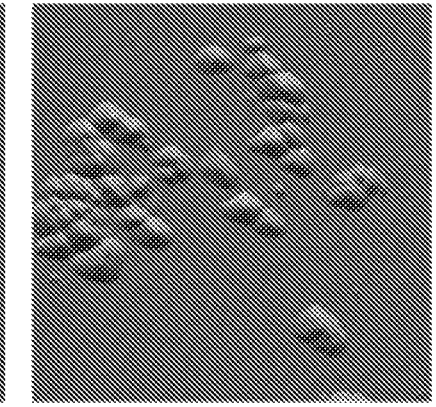
Figure 7:
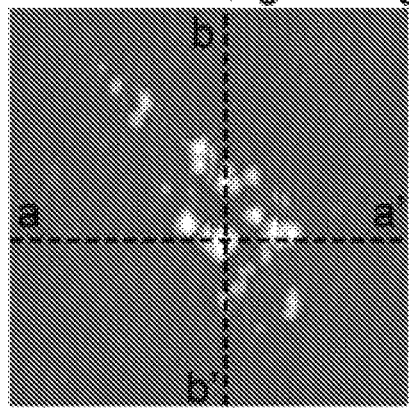
Figure 7:
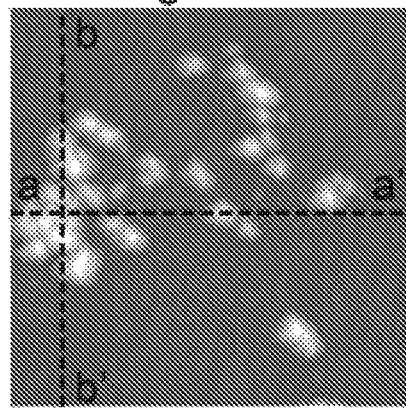
Figure 7:
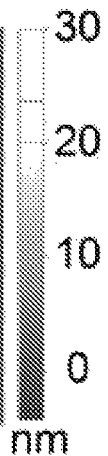
Figure 7:
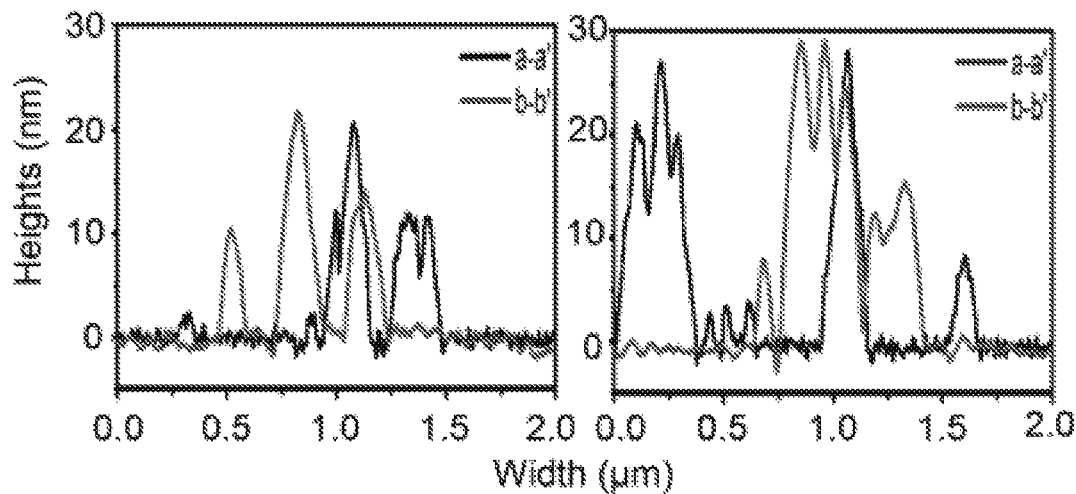
Figure 7:
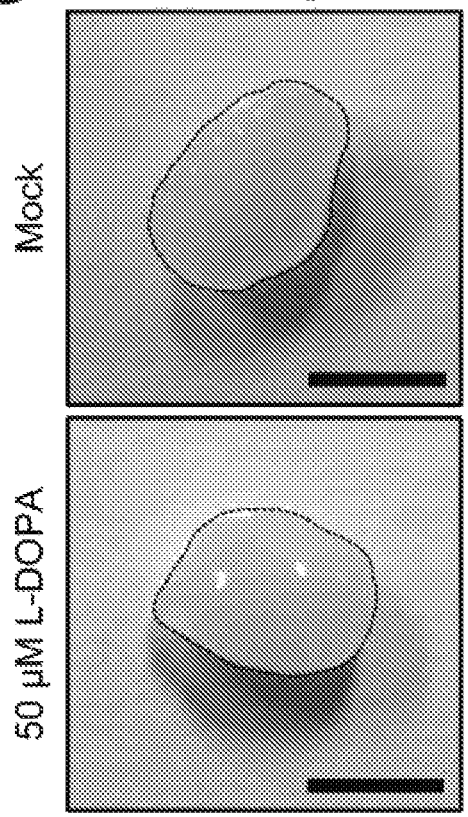
Figure 7:
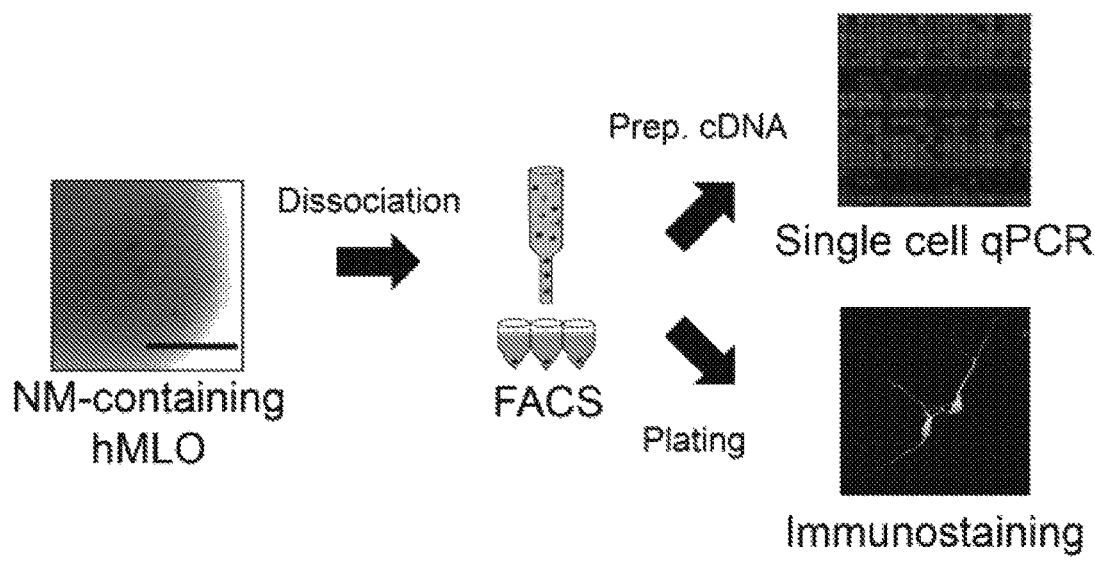
Figure 7:
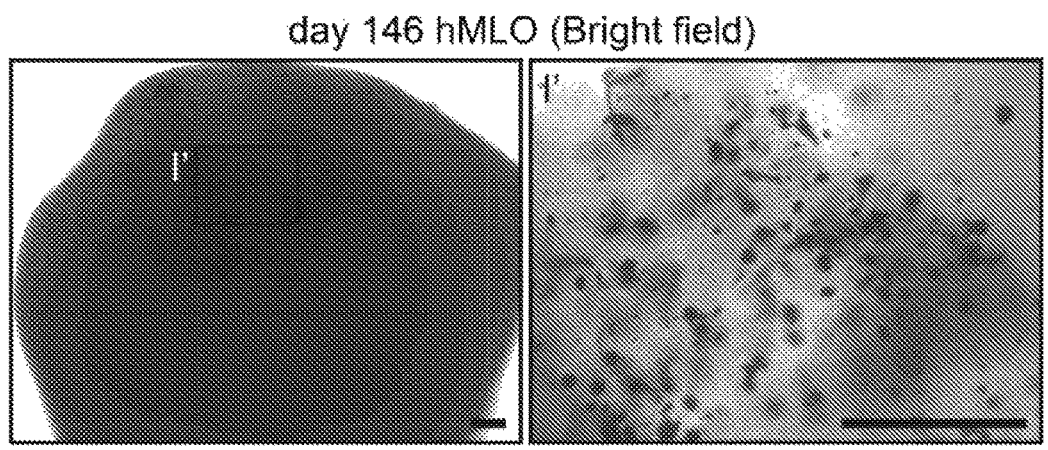
Figure 7:
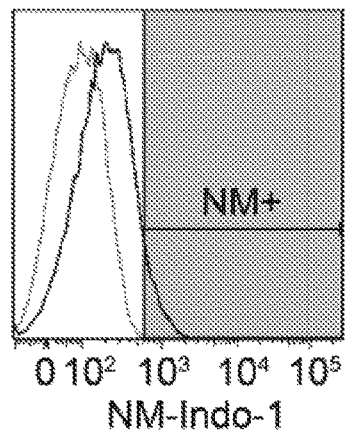
Figure 7:
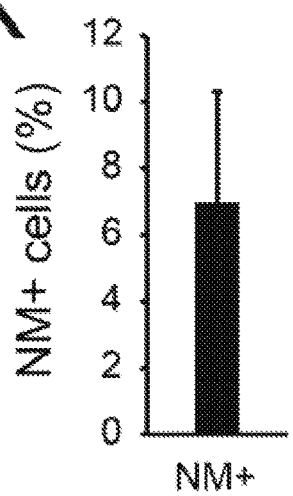
Figure 7:
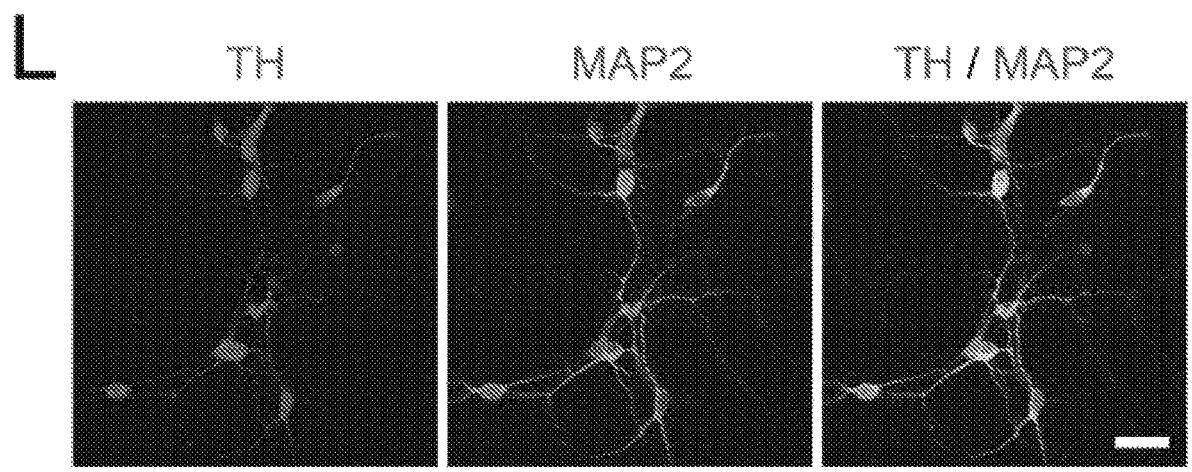
Figure 7:
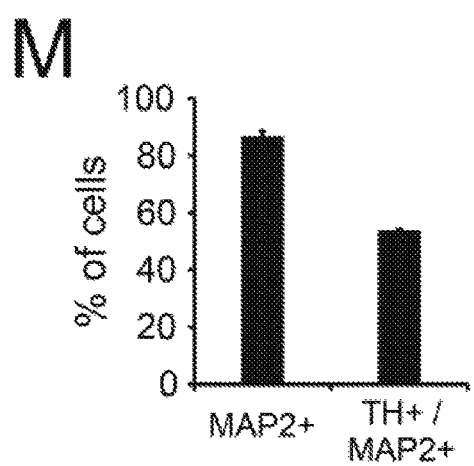
Figure 7:
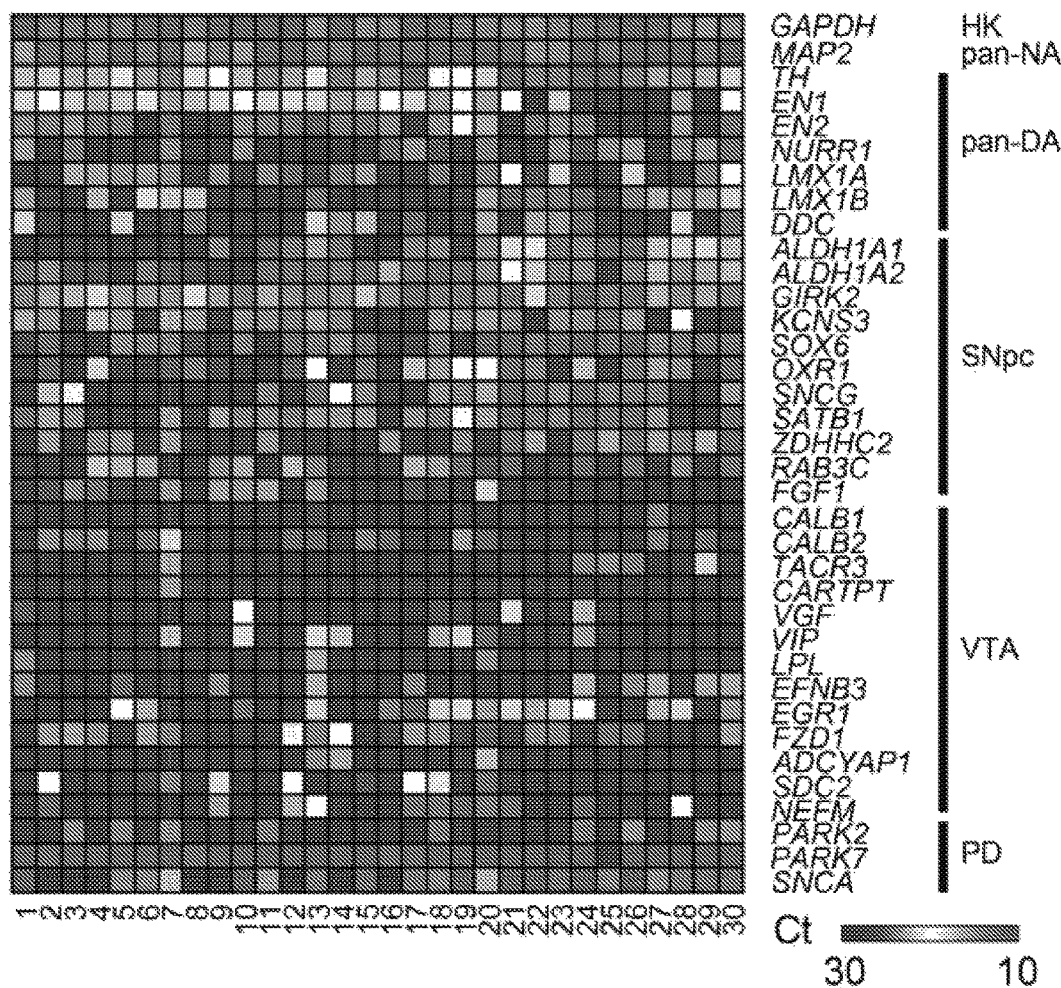
Figure 7:
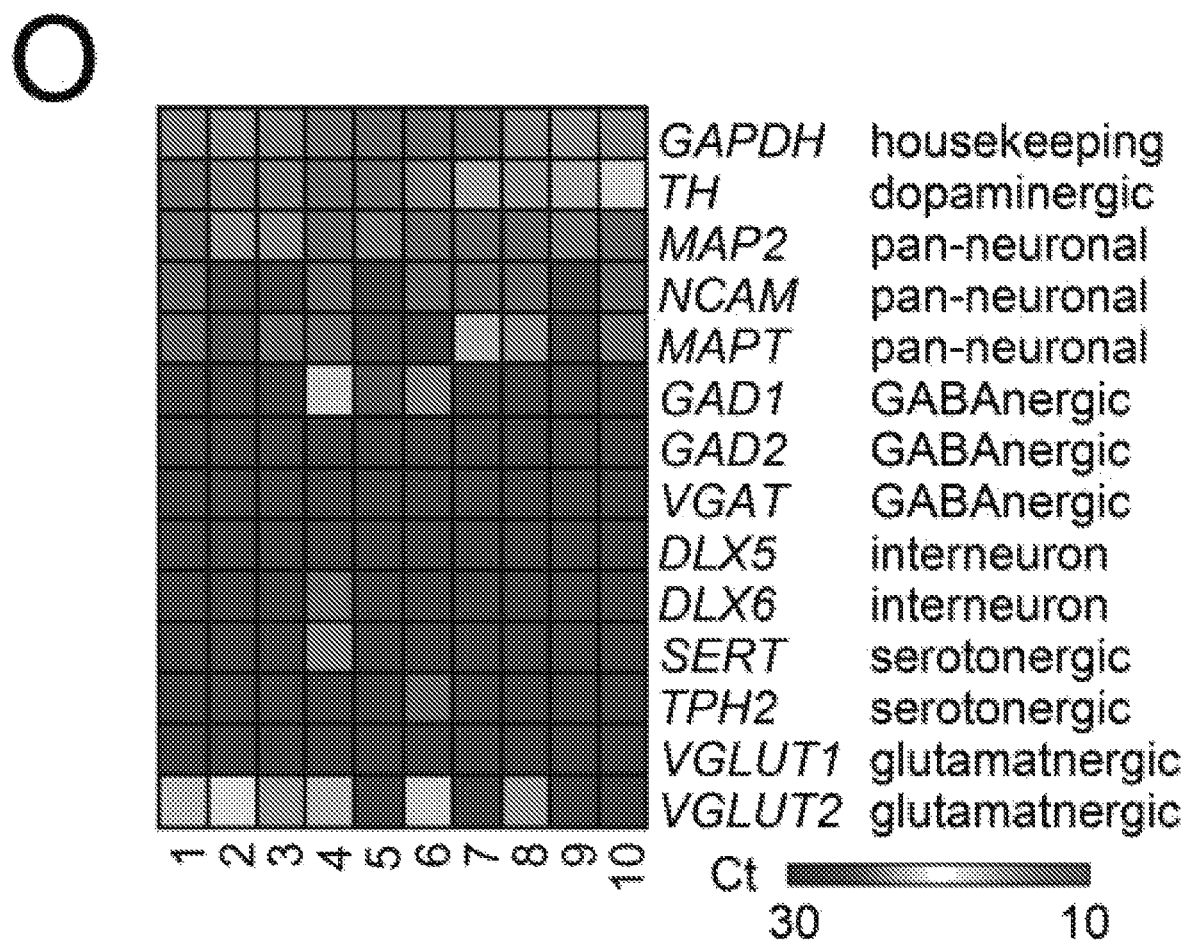

FIG. 7 shows the results of the characterization of neuromelanin (NM) granules isolated in the human midbrain-like organoids (hMLOs) and the results of the transcriptional characterization of neuromelanin (NM)-containing cells. (A) shows micrographs of a Fontana-Masson staining performed on cryosections of an adult mouse skin tissue, which exhibited melanin deposits. Left columns: positive control. A' (bottom left) is an enlarged view of a region in the upper left panel. Right columns: negative control by removing one component (ammonical silver nitrate solution) of Fontana-Masson staining. A" (bottom right) is an enlarged view of a region in the upper right panel. Scale bar=100 µm. (B) shows representative differential interference contrast (DIC) microscopy images of human cerebral organoid at day 15 and 30. Scale bar=200 µm. (C) shows micrographs of cryosections of a human cerebral organoid (hCO) at day 70, stained with Fontana-Masson staining. The lack of neuromelanin (NM)-like granules in the human cerebral organoid (hCO) is noted. Scale bar=100 µm. (D and E) show the results of deflection and height images of neuromelanin (NM) granules, isolated from the day 122 human midbrain-like organoids. Fixed neuromelanin granules were imaged using atomic force microscopy (AFM). (F) shows spectra showing the height profiles generated using atomic force microscopy (AFM) along the a-a' axis (black) and b-b' axis as shown in (E). The actual size of all processed AFM images was 2×2 µm. (G) shows micrographs of human cerebral organoids (hCOs) treated with a vehicle (Mock) and L-DOPA (50 µM) for 10 days. It is shown that the human cerebral organoids did not show any neuromelanin (NM)-like granules, or any coloured deposits (in relation to FIG. 3G). Scale bar=2 mm. (H) shows schematic diagrams illustrating the experimental set up used to investigate neuromelanin (NM)-containing cells. (I) shows representative bright field images of a day 146 human midbrain-like organoid, which was utilized for the sorting of neuromelanin (NM)-containing cells. Scale bar=200 µm. (J and K) show the results of the flow cytometric analysis (FACs) of cells dissociated from human midbrain-like organoids at day 120-150. The column graph shown in (K) shows the quantification of the percentage of neuromelanin (NM)-containing cells sorted in (J). (L) shows micrographs of the immunostaining of sorted neuromelanin (NM)-containing cells with antibodies against MAP2 and tyrosine hydroxylase (TH). Scale bar=50 µm. (M) shows column graphs presenting the results of the quantification of MAP2+ and TH+/MAP2+ cells after neuromelanin flow cytometric analysis (NM FACS) sorting using real-time polymerase chain reaction (qPCR); mean±s.e.m. (standard error of the mean), n=3. (N and O) show gene expression maps depicting the results of single-cell gene expression profiling to identify neuromelanin (NM)-containing midbrain dopaminergic (mDA) neurons from the day 120-150 human midbrain-like organoids using a microfluidic dynamic array. Expression levels (shown as Ct values) are color-coded in grayscale at the bottom of the expression maps, respectively (HK, housekeeping genes; pan-NA, pan-neuronal genes; pan-DA, pan-dopaminergic neuronal genes; SNpc, substantia nigra pars compacta-related genes; VTA, ventral tegmental area-related genes; PD, Parkinson's disease-related genes).

DEFINITION OF TERMS

As used herein, the term "organoid" refers to a miniaturized and, in some cases, a simplified version of an organ produced in vitro in three dimensions, which show realistic and anatomically correct micro-anatomy. They are derived from one or more cells from a tissue, embryonic stem cells or induced pluripotent stem cells, which are capable of self-organisation in three-dimensional culture owing to, for example, their self-renewal and differentiation capacities.

As used herein, the term "embryoid bodies" refers to three-dimensional aggregates of pluripotent stem cells. The pluripotent cell types that comprise embryoid bodies include, but are not limited to, embryonic stem cells (ESCs) derived from the blastocyst stage of embryos from, for example, mouse (mESC), primate, and human (hESC) sources. Additionally, embryoid bodies can be formed from embryonic stem cells derived through alternative techniques, including somatic cell nuclear transfer or the reprogramming of somatic cells to yield induced pluripotent stem cells (iPS). Similar to ES embryonic stem cells cultured in monolayer formats, embryonic stem cells within embryoid bodies undergo differentiation and cell specification along the three germ lineages—endoderm, ectoderm, and mesoderm—which comprise all somatic cell types (which are all cell types in the body, excluding germ line cells).

As used herein, the term "neuronal lineage embryoid bodies" refers to embryoid bodies wherein the pluripotent stem cells have the potential to generate or become neurons.

As used herein, the term "midbrain", also known as the mesencephalon, refers to a section of the brain that is located within the brainstem, below the cerebral cortex, and above the hindbrain.

As used herein, the term "midbrain regionalized tissue" refers to tissue specific to the midbrain region.

As used herein, the term "substantia nigra" refers to a brain structure located in the mesencephalon (also known as the midbrain), which plays an important role in reward and movement. Substantia nigra is Latin for "black substance", reflecting the fact that parts of the substantia nigra appear darker than neighbouring areas due to high levels of neuromelanin in dopaminergic neurons present in these darker regions. Although the substantia nigra appears as a continuous band in brain sections, anatomical studies have found that it actually consists of two parts with very different connections and functions: the pars compacta and the pars reticulate, according to the classification by Sano in 1910. The pars compacta serves mainly as an input to the basal ganglia circuit, supplying the striatum with dopamine. The pars reticulata serves mainly as an output, conveying signals from the basal ganglia to numerous other brain structures.

As used herein, the term "dopamine" refers to 3,4-dihydroxyphenethylamine (IUPAC 4-(2-Aminoethyl)benzene-1,2-diol), which is an organic chemical of the catecholamine and phenethylamine families that plays several important roles in the brain and body. It is an amine synthesized by removing a carboxyl group from a molecule of its precursor chemical L-DOPA, which is synthesized in the brain and kidneys. Dopamine is also synthesized in plants and most multicellular animals. In the brain, dopamine functions as a neurotransmitter—a chemical released by neurons (nerve cells) to send signals to other nerve cells. The brain includes several distinct dopamine pathways, one of which plays a major role in reward-motivated behaviour. Most types of rewards increase the level of dopamine in the brain, and many addictive drugs increase dopamine neuronal activity. Other brain dopamine pathways are involved in motor control and in controlling the release of various hormones. These pathways and cell groups form a dopamine system which is neuromodulatory.

As used herein, the terms "DAn" or "dopaminergic neurons", or "dopamine neurons" refer to projection neurons in the brain that synthesize and release the neurotransmitter dopamine. These dopaminergic neurons form the so-called dopaminergic pathways. Dopamine neurons have axons that run the entire length of the pathway. The neurons' somata produce the enzymes required for dopamine synthesis, which are then transmitted via the projecting axons to their synaptic destinations, where most of the dopamine is produced. Dopaminergic nerve cell bodies in such areas as the substantia nigra tend to be pigmented due to the presence of the black pigment melanin. Dopaminergic pathways are involved in many functions such as executive function, learning, reward, motivation, and neuroendocrine control.

As used herein, the term "NANOG" refers to a transcription factor critically involved with self-renewal of undifferentiated embryonic stem cells. In humans, this protein is encoded by the NANOG gene.

As used herein, the term "Oct4", also known as octamer-binding transcription factor 4 or POU5F1 (POU domain, class 5, transcription factor 1), refers to a protein that in humans is encoded by the POU5F1 gene. Oct-4 is a homeodomain transcription factor of the POU family. This protein is critically involved in the self-renewal of undifferentiated embryonic stem cells. As such, it is frequently used as a marker for undifferentiated cells. Oct-4 expression must be closely regulated; too much or too little will cause differentiation of the cells.

As used herein, the term "inhibitor" refers to a molecule or compound that is capable of decreasing, downregulating or, in some cases, completely ceasing, activity of a target molecule. An inhibitor is usually characterised and named for its target; for example, a compound that binds to an enzyme and thereby decreases its activity is called an enzyme inhibitor. An inhibitor can be either reversible or irreversible, meaning that in terms of binding to its target, this target binding may be subsequently broken (reversible) or not (irreversible). Inhibition of a target molecule can, for example, be competitive, uncompetitive, non-competitive, or mixed. Conversely, a molecule or compound that is capable of increasing, upregulating or initiating the activity of a target molecule is known as an activator.

As used herein, the term "L-DOPA", also known as levodopa or L-3,4-dihydroxyphenylalanine, refers to an amino acid that is made and used as part of the normal biology of humans, some animals and plants. In some animals and humans, L-DOPA is synthesised from the amino acid L-tyrosine. L-DOPA is the precursor to the neurotransmitters dopamine, norepinephrine (noradrenaline), and epinephrine (adrenaline) collectively known as catecholamines. Furthermore, L-DOPA itself mediates neurotrophic factor release by the brain and central nervous system.

DETAILED DESCRIPTION OF THE PRESENT INVENTION

Organoids are cellular structures that mimic the organization and function of organs. In contrast to single cell-type culture, organoids consist of multiple cell types that are organized spatially. The present disclosure demonstrates that 3D culture conditions allow the cells of the organoids to unravel self-organizing capacity with multiple cell types, which reinforces better survival and maturation of specific cell-types through generation of appropriate niche environment. Thus, this disclosure describes a method for generating organoids capable of recapitulating features of the midbrain by differentiating human embryonic stem cells into midbrain-like organoids.

Pluripotent stem cells (PSCs) can be guided to differentiate efficiently into largely homogenous cell types, such as, for example, neurons. These in vitro generated neurons enable downstream studies and potential therapeutic applications. Recent advances in three dimensional (3D) culture systems led to the generation of brain organoids that share resemblance to different parts of the human brains. Disclosed herein is a method to differentiate human pluripotent stem cells into a large multicellular organoid-like structures that contains distinct layers of neuronal cells. Importantly, in it, electrically active and functionally mature midbrain dopaminergic (mDA) neurons, dopamine production, and neuromelanin-like pigments were detected. The application of exogenous dopamine precursor promoted the accumulation of neuromelanin-like pigments. In contrast, neuromelanin was not detected in dopaminergic neurons generated using a non-3D method or midbrain-like organoids generated from mouse embryonic stem cells. Therefore, the 3D method disclosed herein generated a midbrain-like organoids that recapitulate features of human midbrain and this provides a new system to enable the study of human midbrain and related diseases.

Thus, disclosed herein is a method of deriving and maintaining a midbrain-like organoid comprising culturing pluripotent stem cells to obtain neuronal lineage embryoid bodies; culturing the neuronal lineage embryoid bodies from (a) to obtain midbrain regionalized tissues; embedding and culturing the midbrain regionalized tissues from (b) in an extracellular matrix to obtain developing neuroepithelial tissues; and culturing the neuroepithelial tissues from (c) to obtain a midbrain-like organoid.

As used herein, the term "stem cell" refers to undifferentiated biological cells that are capable of differentiating into more specialized cells and that are capable of dividing (through mitosis) to produce more stem cells. Stem cells are found in multicellular organisms. In mammals, there are two broad types of stem cells: embryonic stem cells, which are isolated, for example, from the inner cell mass of blastocysts, and adult stem cells, which are found in various tissues. In adult organisms, stem cells and progenitor cells function as a repair system for the body by replenishing adult tissues. In a developing embryo, stem cells can differentiate into all the specialized cells—derived from any one of the three primary germ layers, called ectoderm, endoderm and mesoderm, present in the early stages of embryonic development—but also maintain the normal turnover of regenerative organs, such as blood, skin, or intestinal tissues.

The three commonly known, accessible sources of autologous adult stem cells in humans are the bone marrow, which requires extraction by harvesting cells, usually from the femur or iliac crest; adipose tissue (lipid cells), which requires extraction by liposuction, and blood, which requires extraction, usually through a apheresis machine. Stem cells can also be taken from umbilical cord blood just after birth. Of all stem cell types, autologous harvesting involves the least risk. By definition, autologous cells are obtained from one's own body. Adult stem cells are frequently used in various medical therapies (e.g., bone marrow transplantation). It is now possible to artificially grow and transform (differentiate) stem cells into specialized cell types, with characteristics consistent with cells of various tissues such as muscles or nerves.

Any mammalian stem cell can be used in accordance with the methods of the invention as disclosed herein, including but not limited to, stem cells isolated from cord blood, placenta and other sources. The stem cells may be isolated from any mammalian species, for example, but not limited to, mouse, rat, rabbit, guinea pig, dog, cat, pig, sheep, cow, horse, monkey and human. In one example, the stem cells are obtained from a human. The stem cells may include pluripotent cells, which are cells that have complete differentiation versatility, that are self-renewing, and can remain dormant or quiescent within tissue. The stem cells may also include multipotent cells or committed progenitor cells. In one example, the method as disclosed herein is performed without the use of human embryonic stem cells. Instead of human embryonic stem cells, other types of pluripotent cells can be used in accordance with the present invention. In another example, the method as disclosed herein is performed on induced pluripotent stem cells. In yet another example, the method as disclosed herein is performed using embryonic stem cells that are not of human origin.

As used herein, the term "pluripotent stem cell" refers to a stem cell that has the potential to differentiate into any of the three germ layers: the endoderm, from which, for example, the interior stomach lining, gastrointestinal tract and the lungs develop; the mesoderm, from which, for example, muscle, bone, blood and urogenital structures develop; or the ectoderm, from which, for example, epidermal tissues and nervous system develop. It is noted however, that cell pluripotency is considered to be a continuum, ranging from the completely pluripotent cell that can form every cell of the embryo proper, for example, embryonic stem cells and induced pluripotent stem cells, to the incompletely or partially pluripotent cell that can form cells of all three germ layers but that may not exhibit all the characteristics of completely pluripotent cells.

Cell culture is the process by which cells are grown under controlled conditions that mimic their natural environment, however, outside of their natural environment. Cell culture conditions vary for each cell type, but the required artificial environments usually consist of a suitable vessel with one or more substrates or one or more media that supply the essential nutrients (for example, such as amino acids, carbohydrates, vitamins and minerals), growth factors, hormones, and gases (usually $CO_2$ and/or $O_2$) required for cell growth, and that regulate the physio-chemical environment (for example, pH buffer, osmotic pressure, temperature, humidity and the like). Most cells require a surface or an artificial substrate on which to grow on (also known as adherent or monolayer culture), whereas others can be grown free-floating in culture medium (also known as suspension culture), usually under agitation (for example, roller bottle culture and the like). In practice, the term "cell culture" refers to the culturing of cells derived from multicellular eukaryotes, especially animal cells as well as diseased human tissue (for example, HeLa cells, PC3 cells and HEK293T cells), in contrast with other types of culture that also grow cells, such as plant tissue culture, fungal culture, microbiological culture (of microbes), and viral culture with the cells being used as hosts for, for example, viral replication.

A cell culture media used in cell culture usually comprises at least the following items: a carbon or carbohydrate source (for example glucose or glutamine) as a source of energy; amino acids for protein synthesis; vitamins, which promote cell survival and growth; a balanced salt solution, usually a mixture of various ions to maintain optimal osmotic pressure within the cells and to act as cofactors for various cofactor-mediated reactions (for example cell adhesion, enzymatic reactions and the like); a pH indicator (for example phenol red; indicating a change in pH from neutral to basic or acidic, which usually indicate the presence of nutrient depletion, contamination, accumulation of necrotic cells and the like) and a buffer (for example, bicarbonate or HEPES buffer) to maintain the required pH in the media. In addition to the components listed above, cell culture media can and usually is modified by the person skilled in the art to their desired requirements in cell culture. For example, the use of fetal calf or bovine serum is required for the growth and maintenance of some cell lines in vitro, but not required for some and to be avoided in others, for example when serum-starved cells are required for cytokine analysis. As defined in the art, a "defined medium" (also known as "chemically defined medium" or "synthetic medium") is a cell culture medium in which all the chemicals used are known and no yeast, animal, or plant tissue is present.

Minimal media are those cell culture media that contain the minimum nutrients possible for colony growth, generally without the presence of amino acids, and are often used to grow "wild-type" microorganisms. Minimal media can also be used to select for or against recombinants or exconjugants. Minimal medium typically contains a carbon source, which may be a sugar such as glucose, or a less energy-rich source such as succinate; various salts, which may vary among bacteria species and growing conditions; these generally provide essential elements such as magnesium, nitrogen, phosphorus, and sulphur to allow the bacteria to synthesize protein and nucleic acids; and water. Supplementary minimal media are minimal media that also contains a single selected agent, usually an amino acid or a sugar. This supplementation allows for the culturing of, for example, specific lines of auxotrophic recombinants.

Selective media are used for the growth of only selected microorganisms. For example, if a microorganism is resistant to a certain antibiotic, for example ampicillin or tetracycline, then that antibiotic can be added to the medium to prevent other cells, which do not possess the resistance, from growing. Media lacking an amino acid such as proline, used in conjunction with, for example, *E. coli* which is unable to synthesize it, were commonly used before the emergence of genomics to map bacterial chromosomes. Selective growth media are also used in cell culture to ensure the survival or proliferation of cells with certain properties, such as antibiotic resistance or the ability to synthesize a certain metabolite. Normally, the presence of a specific gene or an allele of a gene confers the ability to grow in the selective medium upon the cell. In such cases, the gene is termed a marker. Selective growth media for eukaryotic cells commonly contain neomycin to select cells that have been successfully transfected with a plasmid carrying the neomycin resistance gene as a marker. Gancyclovir is an exception to the rule, as it is used to specifically kill cells that carry its respective marker, the Herpes simplex virus thymidine kinase (HSV TK).

Standard ambient growth conditions for cells in cell culture are usually a temperature of 37° C., a $CO_2$ content of 5% and a humidity of 95%. All these conditions can be achieved and maintained by using, for example, an incubator. If required, cell culture media can also be used to bring about certain conditions in the cell, for example, the starvation of a cell prior to specific treatment or analysis methods that require the cells to be starved or withdrawn from certain components of the media (for example, serum-free media).

Cell culture can be performed in a two-dimensional (2D) or a three-dimensional (3D) setting. Examples of two-dimensional cell culture are, but are not limited to, cell culture in any standard cell culture vessel, for example a petri dish, a 6-well plate, a 96-well plate, a culture flask and a roller bottle.

There are a variety of platforms that can be used to facilitate the growth of three-dimensional cellular structures including, but not limited to, scaffold systems such as hydrogel matrices and solid scaffolds, and scaffold-free systems such as low-adhesion plates, nanoparticle facilitated magnetic levitation, and hanging drop plates. Thus, in one example, the method disclosed herein is a three-dimensional method. In another example, the hydrogel is, but is not limited to, natural and synthetic materials, such as animal extracellular matrix, extract hydrogels, protein hydrogels, peptide hydrogels, polymer hydrogels, and wood-based nanocellulose hydrogel. In essence, hydrogels used in three-dimensional cell culture are usually composed of interconnected pores with high water retention, which enables efficient transport of substances such as nutrients and gases.

Cellular differentiation is the process describing the change of a cell from one cell type to another. Most commonly, the cell changes to a more specialized type. Differentiation occurs numerous times during the development of a multicellular organism, as it changes from a simple zygote to a complex system of tissues and cell types. Differentiation continues in adulthood, as adult stem cells divide and create fully differentiated daughter cells during tissue repair and during normal cell turnover. Some differentiation occurs, for example, in response to antigen exposure. Differentiation dramatically changes a cell's size, shape, membrane potential, metabolic activity, and responsiveness to signals. These changes are largely due to highly controlled modifications in gene expression and are the study of the field of epigenetics. With a few exceptions, cellular differentiation almost never involves a change in the DNA sequence itself. Thus, different cells can have very different physical characteristics, usually separated temporally, despite having the same genome.

There are multiple levels of cell potency, which is the cell's state or ability to differentiate into other cell types. A greater potency indicates a larger number of cells that can be derived from the state of that cell. A cell that can differentiate into all cell types, including the placental tissue, is known as totipotent. In mammals, only the zygotes, and subsequent blastomeres, are totipotent, while in plants many differentiated cells can become totipotent with simple laboratory techniques. A cell that can differentiate into all cell types of the adult organism is known as pluripotent. Such cells are also known as meristematic cells in higher plants, and embryonic stem cells in animals. Potency of a cell can be induced and in some cases even reversed, that is a change in differentiation of a cell from more differentiated (that is, closer to the final end cell type) to less differentiated (that is, closer to the totipotent or pluripotent stage of the cell). For example, it has been shown that virally induced expression of four transcription factors Oct4, Sox2, c-Myc, and Kfl4 (also known as Yamanaka factors) is sufficient to create pluripotent (iPS) cells from adult fibroblasts. A multipotent cell is one that can differentiate into multiple different, but closely related cell types. Oligopotent cells are more restricted in terms of their differentiation capability than multipotent, but can still differentiate into a few closely related cell types. Finally, unipotent cells can differentiate into only one cell type, but are capable of self-renewal. In cytopathology, the level of cellular differentiation is used, for example, as a measure of cancer progression. "Grade" is a marker of how differentiated a cell in a tumour is.

Three basic categories of cells make up the mammalian body: germ cells, somatic cells, and stem cells. Each of the approximately 100 trillion ($10^{14}$) cells in an adult human has its own copy or copies of the genome, except for certain cell types, such as red blood cells which lack nuclei in their fully differentiated state. Most cells are diploid, meaning that they have two copies of each chromosome. Such cells, called somatic cells, make up most of the human body, such as skin and muscle cells. Cells differentiate to specialize for different functions.

Germ line cells are any line of cells in an organism that give rise to gametes—eggs and sperm—and are therefore continuous through the generations. Stem cells, on the other hand, have the ability to divide for indefinite periods and to give rise to specialized cells, which are best described in the context of human development.

Development begins when a sperm fertilizes an egg and creates a single cell that has the potential to form an entire organism. In the short time after fertilization, this cell divides into identical cells. In humans, approximately four days after fertilization and after several cycles of cell division, these cells begin to specialize, forming a hollow sphere of cells, called a blastocyst. The blastocyst has an outer layer of cells and a cluster of cells within the hollow sphere called the inner cell mass. The cells of the inner cell mass go on to form virtually all of the different tissues present within the human body. Although the cells of the inner cell mass can form virtually every type of cell found in the human body, they cannot form an organism. These cells are referred to as pluripotent.

Pluripotent stem cells undergo further specialization into multipotent progenitor cells that then give rise to functional cells. Examples of stem and progenitor cells include, but are not limited to, radial glial cells (embryonic neural stem cells) that give rise to excitatory neurons in the fetal brain through the process of neurogenesis; hematopoietic stem cells (adult stem cells) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; and muscle satellite cells (progenitor cells) that contribute to differentiated muscle tissue.

A pathway that is guided by the cell adhesion molecules consisting of four amino acids, arginine, glycine, asparagine, and serine, is created as the cellular blastomere differentiates from the single-layered blastula to the three primary layers of germ cells in mammals, namely the ectoderm, mesoderm and endoderm (listed from most distal (exterior) to proximal (interior)). The ectoderm ultimately forms the skin and the nervous system of the organism, the mesoderm forms the bones and muscular tissue, and the endoderm forms the internal organs.

Each specialized cell type in an organism expresses a subset of all the genes that constitute the genome of that species. Each cell type is defined by its particular pattern of regulated gene expression. Cell differentiation is thus a transition of a cell from one cell type to another and, as a result, involves a switch from one pattern of gene expression to another. Cellular differentiation during development can be understood as the result of a gene regulatory network. A regulatory gene and its cis-regulatory modules are nodes in a gene regulatory network; they receive input and create output elsewhere in the network. A few evolutionarily conserved types of molecular processes are often involved in the cellular mechanisms that control these changes. The major types of molecular processes that control cellular differentiation involve cell signalling. Many of the signal molecules that convey information from cell to cell during the control of cellular differentiation are called growth factors. Although the details of specific signal transduction pathways vary, these pathways often share the following general steps. A ligand produced by one cell binds to a receptor in the extracellular region of another cell, inducing a conformational change in the receptor. The shape of the cytoplasmic domain of the receptor changes, and the receptor acquires enzymatic activity. The receptor then catalyses reactions that phosphorylate other proteins, activating them. A cascade of phosphorylation reactions eventually activates a dormant transcription factor or cytoskeletal protein, thus contributing to the differentiation process in the target cell. Cells and tissues can vary in competence, which is the variation in their ability to respond to external signals.

Signal induction refers to cascades of signalling events, during which a cell or tissue signals to another cell or tissue to influence its developmental fate. For example, the role of the lens in eye formation in distinct species of fish has been studied and provides a striking example of signal induction.

Other important mechanisms fall under the category of asymmetric cell divisions, divisions that give rise to daughter cells with distinct developmental fates. Asymmetric cell divisions can occur because of asymmetrically expressed maternal cytoplasmic determinants or because of cell signalling. In the former mechanism, distinct daughter cells are created during cytokinesis because of an uneven distribution of regulatory molecules in the parent cell; the distinct cytoplasm that each daughter cell inherits results in a distinct pattern of differentiation for each daughter cell.

Since each cell, regardless of cell type, possesses the same genome, determination of the cell type must occur at the level of gene expression. While the regulation of gene expression can occur through cis- and trans-regulatory elements including a gene's promoter and enhancers, the problem arises as to how this expression pattern is maintained over numerous generations of cell division. As it turns out, epigenetic processes play a crucial role in regulating the decision to adopt a stem, progenitor, or mature cell fate.

Embryonic stem cells are capable of self-renewing and differentiating to the desired fate depending on its position within the body. Stem cell homeostasis is maintained through epigenetic mechanisms that are highly dynamic in regulating the chromatin structure as well as specific gene transcription programs. Epigenetics has been used to refer to changes in gene expression, which are heritable through modifications not affecting the DNA sequence. For example, the mammalian epigenome undergoes global remodelling during early stem cell development that requires commitment of cells to be restricted to the desired lineage. There has been evidence suggesting that the maintenance of the lineage commitment of stem cells is controlled by epigenetic mechanisms, such as, but not limited to, DNA methylation, histone modifications and regulation of ATP-dependent remoulding of chromatin structure.

In molecular biology, a transcription factor (or sequence-specific DNA-binding factor) is a protein that controls the rate of transcription of genetic information from DNA to messenger RNA, by binding to a specific DNA sequence. In turn, this helps to regulate the expression of genes near that sequence. This is essential in cellular development, for example during embryogenesis.

Transcription factors work alone or in combination with other proteins in a complex, by promoting (as an activator), or blocking (as a repressor) the recruitment of RNA polymerase (the enzyme that performs the actual transcription of genetic information from DNA to RNA) to specific genes. A defining feature of transcription factors is that they contain at least one DNA-binding domain (DBD), which attaches to a specific sequence of DNA adjacent to the genes that they regulate. Transcription factors are usually classified into different families based on their DNA-binding domains. Other proteins such as, but not limited to, coactivators, chromatin re-modellers, histone acetyltransferases, histone deacetylases, kinases, and methylases, while also essential to gene regulation, lack DNA-binding domains, and, therefore, do not fall under the definition of transcription factors. Transcription factors are one of the groups of proteins that read and interpret the genetic "blueprint" in the DNA. They bind to the DNA and help initiate a program of increased or decreased gene transcription. As such, they are vital for many important cellular processes. Transcription factors are involved in many important functions and biological roles, for example, but not limited to, organism development.

Many transcription factors in multicellular organisms are involved in development. Responding to stimuli, these transcription factors switch the transcription of the appropriate genes on or off, which, in turn, allows for the changes in cell morphology or activities needed for cell fate determination and cellular differentiation. The Hox transcription factor family, for example, is important for proper body pattern formation in organisms as diverse as fruit flies to humans. Another example is the transcription factor encoded by the Sex-determining Region Y (SRY) gene, which plays a major role in determining sex in humans.

Thus, in one example, the method is as disclosed herein, wherein the pluripotent stem cells are cultured in a first cell culture medium, wherein the first cell culture medium comprises TGF-β inhibitor and/or SMAD2/3 inhibitor and/or WNT-signalling activator. In one example, the first cell culture medium comprises TGF-β inhibitor or SMAD2/3 inhibitor. In another example, the first cell culture medium comprises TGF-β inhibitor and SMAD2/3 inhibitor. In yet another example, the first cell culture medium comprises TGF-β inhibitor or SMAD2/3 inhibitor, and WNT-signalling activator. In a further example, the first cell culture medium comprises TGF-β inhibitor and SMAD2/3 inhibitor and WNT-signalling activator. In yet another example, the first cell culture medium comprises TGF-β inhibitor or SMAD2/3 inhibitor or WNT-signalling activator.

The present invention also includes a culture medium for deriving and maintaining neuronal lineage embryoid bodies comprising TGF-β inhibitor and/or SMAD2/3 inhibitor; and WNT-signaling activator. In one example, culture medium for deriving and maintaining neuronal lineage embryoid bodies further comprises a basal cell growth medium at a percentage of 40% to 50% (optionally at 47%), a basal embryonic neuronal cell growth medium at a percentage of 40% to 50% (optionally at 47%), a glutamine supplement at a percentage of 0.5% to 3% (optionally at 1%), a non-essential amino acid (NEAA) supplement at a percentage of 0.5% to 3% (optionally at 1%), antibiotics at a percentage of 0.5% to 3% (optionally at 1%), a reducing agent at a percentage of 0.05% to 0.5% (optionally at 0.1%), a supplement for expansion of undifferentiated cells, at a percentage of 0.5% to 3% (optionally at 1%), a supplement for the maintenance of neurons, at a percentage of 0.5% to 5% (optionally at 1%) and a supplement for cell proliferation, at a concentration of 0.1 to 5 μg/ml (optionally at 1 μg/ml).

In another example, there is disclosed a cell culture medium for deriving and maintaining neuronal lineage embryoid bodies, wherein the medium comprises 40% to 50% of DMEM/F12 medium, 40% to 50% of neurobasal medium, 0.5% to 3% L-alanyl-L-glutamine dipeptide, 0.5% to 3% non-essential amino acid (NEAA) supplement, 0.5% to 3% of penicillin G and streptomycin, 0.05% to 0.5% β-mercaptoethanol, 0.5% to 3% of N-2 Supplement, 0.5% to 5% of B27 without vitamin A, 0.1 to 5 g/ml of heparin, between 30 nM to 20 μM of SB431542, between 30 nM to about 20 µM of CHIR99021, between 30 nM to 20 µM of Y27632 and 100 ng/ml to 300 ng/ml Noggin Also included in the present invention is a culture medium for deriving and maintaining midbrain regionalized tissues, comprising TGF-β inhibitor and/or SMAD2/3 inhibitor; WNT-signalling activator; hedgehog signalling protein; and fibroblast growth factor. In one example, the culture medium for deriving and maintaining midbrain regionalized tissues as disclosed herein further comprises a basal cell growth medium at a percentage of 40% to 50% (optionally at 47%), a basal embryonic neuronal cell growth medium at a percentage of 40% to 50% (optionally at 47%), a glutamine supplement at a percentage of 0.5% to 3% (optionally at 1%), a non-essential amino acid (NEAA) supplement at a percentage of 0.5% to 3% (optionally at 1%), antibiotics at a percentage of 0.5% to 3% (optionally at 1%), a reducing agent at a percentage of 0.05% to 0.5% (optionally at 0.1%), a supplement for expansion of undifferentiated cells, at a percentage of 0.5% to 3% (optionally at 1%), a supplement for the maintenance of neurons, at a percentage of 0.5% to 5% (optionally at 1%) and a supplement for cell proliferation, at a concentration of 0.1 to 5 µg/ml (optionally at 1 µg/ml).

In another example, there is disclosed a culture medium for deriving and maintaining midbrain regionalized tissues, wherein the medium comprises 40% to 50% of DMEM/F12 medium, 40% to 50% of neurobasal medium, 0.5% to 3% L-alanyl-L-glutamine dipeptide, 0.5% to 3% non-essential amino acid (NEAA) supplement, 0.5% to 3% of penicillin G and streptomycin, 0.05% to 0.5% β-mercaptoethanol, 0.5% to 3% of N-2 Supplement, 0.5% to 5% of B27 without vitamin A, 0.1 to 5 g/ml of heparin, between 30 nM to 20 µM of SB431542, between 30 nM to about 20 µM of CHIR99021, between 30 nM to 20 µM of Y27632, 100 ng/ml to 300 ng/ml Noggin, 100 ng/ml to 300 ng/ml SHH-C25II, and 100 ng/ml to 300 ng/ml FGF8.

The present invention also encompasses a culture medium for deriving and maintaining developing neuroepithelial tissues, comprising hedgehog signaling protein; and fibroblast growth factor. In one example, the culture medium for deriving and maintaining developing neuroepithelial tissue further comprises a basal embryonic neuronal cell growth medium at a percentage of 90% to 95% (optionally 94%), a glutamine supplement at a percentage of 0.5% to 3% (optionally 1%), a non-essential amino acid (NEAA) supplement at a percentage of 0.5% to 3% (optionally 1%), antibiotics at a percentage of 0.5% to 3% (optionally 1%), a reducing agent at a percentage of 0.05% to 0.5% (optionally 0.1%), a supplement for expansion of undifferentiated cells, at a percentage of 0.5% to 3% (optionally 1%), a supplement for the maintenance of neurons, at a percentage of 0.5% to 5% (optionally 2%), a growth supplement at a concentration of 0.5 to 10 µg/ml (optionally 2.5 g/ml), and a growth enhancer of stem cells at the concentration of 50 to 500 ng/ml (optionally 200 ng/ml).

In one example, disclosed herein is a culture medium for deriving and maintaining developing neuroepithelial tissues, wherein the medium comprises 80% to 100% of neurobasal medium, 0.5% to 3% L-alanyl-L-glutamine dipeptide, 0.5% to 3% non-essential amino acid (NEAA) supplement, 0.5% to 3% of penicillin G and streptomycin, 0.05% to 0.5% β-mercaptoethanol, 0.5% to 3% of N-2 Supplement, 0.5% to 5% of B27 without vitamin A, 0.5 to 10 µg/ml of insulin, 50 to 500 ng/ml of laminin, 100 ng/ml to 300 ng/ml SHH-C25II, and 100 ng/ml to 300 ng/ml FGF8.

The present invention also encompasses a culture medium for deriving and maintaining a midbrain-like organoid, comprising neurotrophic factor; ascorbic acid; and activator of cAMP-dependent pathways. In one example, the culture medium for deriving and maintaining a midbrain-like organoid further comprises a basal embryonic neuronal cell growth medium at a percentage of 90% to 95% (optionally 94%), a glutamine supplement at a percentage of 0.5% to 3% (optionally 1%), a non-essential amino acid (NEAA) supplement at a percentage of 0.5% to 3% (optionally 1%), antibiotics at a percentage of 0.5% to 3% (optionally 1%), a reducing agent at a percentage of 0.05% to 0.5% (optionally 0.1%), a supplement for expansion of undifferentiated cells, at a percentage of 0.5% to 3% (optionally 1%), a supplement for the maintenance of neurons, at a percentage of 0.5% to 5% (optionally 2%), a growth supplement at a concentration of 0.5 to 10 µg/ml (optionally 2.5 µg/ml), and a growth enhancer of stem cells at the concentration of 50 to 500 ng/ml (optionally 200 ng/ml).

In another example, there is disclosed a cell culture medium for deriving and maintaining a midbrain-like organoid, wherein the medium comprises 80% to 100% of neurobasal medium, 0.5% to 3% L-alanyl-L-glutamine dipeptide, 0.5% to 3% non-essential amino acid (NEAA) supplement, 0.5% to 3% of penicillin G and streptomycin, 0.05% to 0.5% β-mercaptoethanol, 0.5% to 3% of N-2 Supplement, 0.5% to 5% of B27 without vitamin A, between 5 to 50 ng/ml BDNF, between 5 to 50 ng/ml GDNF, between 70 µM to 600 µM ascorbic acid, and between 20 µM to 850 µM of dc-cAMP.

In another example, the first cell culture medium further comprises a basal cell growth medium at a percentage of 40% to 50% (optionally at 47%), a basal embryonic neuronal cell growth medium at a percentage of 40% to 50% (optionally at 47%), a glutamine supplement at a percentage of 0.5% to 3% (optionally at 1%), a non-essential amino acid (NEAA) supplement at a percentage of 0.5% to 3% (optionally at 1%), antibiotics at a percentage of 0.5% to 3% (optionally at 1%), a reducing agent at a percentage of 0.05% to 0.5% (optionally at 0.1%), a supplement for expansion of undifferentiated cells, at a percentage of 0.5% to 3% (optionally at 1%), a supplement for the maintenance of neurons, at a percentage of 0.5% to 5% (optionally at 1%) and a supplement for cell proliferation, at a concentration of 0.1 to 5 g/ml (optionally at 1 µg/ml).

Disclosed herein is also a second culture medium. Thus, in one example, the method is as disclosed herein, wherein the neuronal lineage embryoid bodies are cultured in a second cell culture medium, wherein the second cell culture medium comprises TGF-β inhibitor and/or SMAD2/3 inhibitor; WNT-signalling activator; hedgehog signalling protein; and fibroblast growth factor. In another example, the second cell culture medium comprises TGF-β inhibitor and SMAD2/3 inhibitor, WNT-signalling activator, hedgehog signalling protein and fibroblast growth factor. In another example, the second cell culture medium comprises TGF-β inhibitor or SMAD2/3 inhibitor; WNT-signalling activator; hedgehog signalling protein; and fibroblast growth factor.

In another example, the second cell culture medium further comprises a basal cell growth medium at a percentage of 40% to 50% (optionally at 47%), a basal embryonic neuronal cell growth medium at a percentage of 40% to 50% (optionally at 47%), a glutamine supplement at a percentage of 0.5% to 3% (optionally at 1%), a non-essential amino acid (NEAA) supplement at a percentage of 0.5% to 3% (optionally at 1%), antibiotics at a percentage of 0.5% to 3% (optionally at 1%), a reducing agent at a percentage of 0.05% to 0.5% (optionally at 0.1%), a supplement for expansion of undifferentiated cells, at a percentage of 0.5% to 3% (optionally at 1%), a supplement for the maintenance of neurons, at a percentage of 0.5% to 5% (optionally at 1%) and a supplement for cell proliferation, at a concentration of 0.1 to 5 µg/ml (optionally at 1 µg/ml).

Disclosed herein is also a third culture medium. This, in one example, the method is as disclosed herein, wherein the midbrain regionalized tissues are cultured in a third cell culture medium, wherein the third cell culture medium comprises hedgehog signalling protein; and fibroblast growth factor.

In another example, the third cell culture medium further comprises a basal embryonic neuronal cell growth medium at a percentage of 90% to 95% (optionally 94%), a glutamine supplement at a percentage of 0.5% to 3% (optionally 1%), a non-essential amino acid (NEAA) supplement at a percentage of 0.5% to 3% (optionally 1%), antibiotics at a percentage of 0.5% to 3% (optionally 1%), a reducing agent at a percentage of 0.05% to 0.5% (optionally 0.1%), a supplement for expansion of undifferentiated cells, at a percentage of 0.5% to 3% (optionally 1%), a supplement for the maintenance of neurons, at a percentage of 0.5% to 5% (optionally 2%), a growth supplement at a concentration of 0.5 to 10 µg/ml (optionally 2.5 g/ml), and a growth enhancer of stem cells at the concentration of 50 to 500 ng/ml (optionally 200 ng/ml).

Disclosed herein is also a fourth culture medium. In one example, the method is as described herein, wherein the neuroepithelial tissues are cultured in a fourth cell culture medium, wherein the fourth cell culture medium comprises neurotrophic factor, ascorbic acid; and activator of cAMP-dependent pathways.

In one example, the fourth cell culture medium further comprises a basal embryonic neuronal cell growth medium at a percentage of 90% to 95% (optionally 94%), a glutamine supplement at a percentage of 0.5% to 3% (optionally 1%), a non-essential amino acid (NEAA) supplement at a percentage of 0.5% to 3% (optionally 1%), antibiotics at a percentage of 0.5% to 3% (optionally 1%), a reducing agent at a percentage of 0.05% to 0.5% (optionally 0.1%), a supplement for expansion of undifferentiated cells, at a percentage of 0.5% to 3% (optionally 1%), a supplement for the maintenance of neurons, at a percentage of 0.5% to 5% (optionally 2%), a growth supplement at a concentration of 0.5 to 10 µg/ml (optionally 2.5 µg/ml), and a growth enhancer of stem cells at the concentration of 50 to 500 ng/ml (optionally 200 ng/ml).

In one example, the basal growth cell medium is, but is not limited to Eagle's minimal essential medium (EMEM), alpha minimum essential medium (aMEM), Dulbecco's modified Eagle's medium (DMEM), Dulbecco's Modified Eagle medium/Nutrient Mixture F-12 (DMEM/F-12) Roswell Park Memorial Institute medium (RPMI or RPMI 1640), Glasgow's Minimal Essential Medium (GMEM), Biggers, Gwatkin, and Judah medium (BGJ), Biggers, Gwatkin, and Judah medium Fitton-Jackson modification (BGJb), Basal Medium Eagle (BME), Brinster's medium for ovum culture (BMOC-3), Connaught Medical Research Laboratories medium (CMRL), neurobasal medium, $CO_2$-Independent medium, Ham's F-10 Nutrient Mixture, Ham's F-12 Nutrient Mixture, Improved MEM, Iscove's modified Dulbecco's medium (IMDM), medium 199, Leibovitz's L-15, McCoy's 5A, MCDB 131, Media 199, mTeSR media, Minimum Essential Media (MEM), Modified Eagle Medium (MEM), Waymouth's MB 752/1, Williams' Media E, or combinations, known substitutions or modifications thereof. In one example, the basal cell growth medium is Dulbecco's Modified Eagle's Medium/Nutrient F-12 (DMEM/F12). In another example, the basal embryonic neuronal cell growth medium is neurobasal medium.

Any cell culture media may be supplemented with further components, as and when required based on the experiment to be performed, the cell type in questions, as well as the required status of the cell (starved or otherwise). Cell culture supplements are, but are not limited to, serum, amino acids, chemical compounds, salts, buffering salts or agents, antibiotics, antimycotics, cytokines, growth factors, hormones, lipids, and derivatives thereof.

In one example, the serum is, but is not limited to, fetal calf serum (FCS), fetal bovine serum (FBS), human serum (huS), platelet lysate (hPL), human platelet lysate (hPL), and combinations thereof.

In one example, the antimycotic is, but is not limited to, amphotericin B, clotimazol, nystatin and combinations thereof.

In one example, the amino acid is, but is not limited to, isoleucine, leucine, lysine, methionine, phenylalanine, threonine, tryptophan, valine, arginine, cysteine, cystine, histidine, tyrosine, alanine, aspartic acid, asparagine, glutamine, glutamic acid, glycine, hydroxproline, proline, serine, combinations and derivatives thereof. In one example, the amino acid is glutamine. The amino acids listed herein may be provided in either the L- or the D-stereoisomer, as required. In one example, the glutamine supplement is L-alanyl-L-glutamine dipeptide.

In a further example, the antibiotic is, but is not limited to, ampicillin, penicillin, chloramphenicol, gentamycin, kanamycin, neomycin, streptomycin, tetracycline, polymyxin B, actinomycin, bleomycin, cyclohexamide, geneticin (G148), hygromycin B, mitomycin C and combinations thereof. In one example, the antibiotic is penicillin. In another example, the antibiotic is streptomycin. In yet another example, the antibiotic is penicillin and streptomycin.

In one example, the salt, buffering salt or agent is, but is not limited to, sodium chloride (NaCl), potassium chloride (KCl), sodium hydrogen phosphate ($Na_2HPO_4$), monosodium phosphate ($NaH_2PO_4$), monopotassium phosphate ($KH_2PO_4$), magnesium sulfate ($MgSO_4$), calcium chloride ($CaCl_2$), calcium chloride ($CaCl_2 \times 2\ H_2O$), dextrose, glucose, Sodium bicarbonate ($NaHCO_3$) and combinations thereof.

In one example, the chemical compound is, but is not limited to sodium bicarbonate and β-mercaptoethanol. In one example, the reducing agent is β-mercaptoethanol.

In another example, the supplement for expansion of undifferentiated cells is N-2 Supplement.

In one example, the supplement for the maintenance of neurons is B27 without vitamin A.

In another example, the supplement for cell proliferation is heparin.

In one example, the growth supplement is insulin.

In another example, the growth enhancer of stem cells is laminin.

Cells can be kept in culture for extended periods of time. Theoretically, given the optimal growth conditions and in a stable cell culture environment, cells (for example immortalized cell lines) can be kept indefinitely. Otherwise, technically, the life of a cell in cell culture is defined by the physical constraints of the cells and can be calculated, for example by determining the Hayflick limit of the cell, or based on the telomere length of a cell. Thus, in one example, the culturing step as defined herein under (a) is for 3 to 5 days. In one example, the culturing step as defined herein under (b) is for 3 to 5 days. In one example, the culturing step as defined herein under (c) is for 1 to 2 days.

In one example, the method is as disclosed herein, wherein the neuronal lineage embryoid bodies to be cultured in the culture medium are characterized by the markers PAX6 and SOX1. In another example, the neuronal lineage marker is PAX6. In another example, the neuronal lineage marker is SOX1.

In another example, the method is as disclosed herein, wherein the pluripotent markers are OCT4 and NANOG. In another example, the pluripotent marker is OCT4. In yet another example, the pluripotent marker is OCT4.

In another example, the method is as disclosed herein, wherein the neuronal lineage embryoid bodies to be cultured in the first and second cell culture medium are characterized by, but not limited to, one or more of the following markers: PAX6 and SOX1. OCT4 and NANOG.

In one example, the method is as disclosed herein, wherein the midbrain regionalized tissues to be cultured in the cell culture medium are characterized by any one or more of the following markers: CORIN, OTX2, FOXA2, MASH1, NURR1, LMX1A and combinations thereof. In one example, the marker is CORIN. In another example, the marker is OTX2. In yet another example, the marker is FOXA2. In a further example, the marker is MASH1. In another example, the marker us NURR1. In yet another example, the marker is LMX1A. In one example, the markers are CORIN and OTX2. In another example, the markers are CORIN and FOXA2. In yet another example, the markers are CORIN and MASH1. In a further example, the markers are CORIN and LMX1A. In another example, the markers are OXT2 in combination with any other marker as disclosed above. In another example, the markers are FOXA2 in combination with any other marker as disclosed above. In another example, the markers are MASH1 in combination with any other marker as disclosed above. In another example, the markers are NURR1 in combination with any other marker as disclosed above. In another example, the markers are LMX1A in combination with any other marker as disclosed above. In another example, the method is as disclosed herein, wherein the midbrain regionalized tissues to be cultured in the third cell culture medium are characterized by the markers CORIN, OTX2, FOXA2 and LMX1A.

In one example, the method is as disclosed herein, wherein the midbrain-like organoid is human midbrain-like organoid. In another example, the isolated midbrain-like organoid is a human midbrain-like organoid.

The object of the present invention also includes the isolation of a midbrain-like organoid using the method as disclosed herein. In one example, the isolated midbrain-like organoid comprises midbrain-specific cells. In another example, there is disclosed an isolated midbrain-like organoid comprising midbrain-specific cells. In yet another example, the isolated midbrain-like organoids are mature midbrain-like organoids. In another example, the isolated midbrain-like organoids are Substantia nigra organoids. In another example, the midbrain-specific cells comprised in the isolated midbrain-like organoids disclosed herein comprise dopaminergic neurons.

In a further example, the isolated midbrain-like organoid as disclosed herein is characterized by the presence at least one or more following features: a proliferative ventral zone (VZ), an intermediate zone (IZ) and a mantle zone (MZ). In one example, the proliferative ventral zone (VZ) is characterized by the presence of neural progenitors. In another example, the intermediate zone (IZ) is characterized by the presence of immature midbrain dopaminergic neurons. In yet another example, the mantle zone (MZ) is characterized by the presence of mature midbrain dopaminergic neurons. In one example, the proliferative ventral zone (VZ) is characterized by the presence of neural progenitors, the intermediate zone (IZ) is characterized by the presence of immature midbrain dopaminergic neurons, and the mantle zone (MZ) is characterized by the presence of mature midbrain dopaminergic neurons.

In one example, the neuroepithelia of the isolated midbrain-like organoid disclosed herein displays an apical-basal polarity. In another example, the apical-basal polarity is characterized by the localization of any one of the following markers: atypical protein kinase C (aPKC), Ki67, MAP2, OTX2, EdU and MASH1

In one example, the isolated midbrain-like organoid is as disclosed herein, wherein the neural progenitors and/or immature midbrain dopaminergic neurons are characterized by the neural progenitor marker PAX6. In another example, the isolated midbrain-like organoid is as disclosed herein, wherein the neural progenitors and/or immature midbrain dopaminergic neurons are characterized by the neural progenitor marker SOX1. In one example, the isolated midbrain-like organoid is as disclosed herein, wherein the neural progenitors and/or immature midbrain dopaminergic neurons are characterized the neural progenitor markers PAX6 and SOX1.

In one example, the isolated midbrain-like organoid is as disclosed herein, wherein the neural progenitors and/or immature midbrain dopaminergic neurons are characterized by one or more of the following immature midbrain dopaminergic neuron markers MASH1, OTX2 and NURR1. In another example, the neural progenitors and/or immature midbrain dopaminergic neurons are characterized by the immature midbrain dopaminergic neuron marker MASH1. In yet another example, the neural progenitors and/or immature midbrain dopaminergic neurons are characterized by the immature midbrain dopaminergic neuron marker OTX2. In a further example, the neural progenitors and/or immature midbrain dopaminergic neurons are characterized by the immature midbrain dopaminergic neuron marker NURR1. In another example, the neural progenitors and/or immature midbrain dopaminergic neurons are characterized by the immature midbrain dopaminergic neuron markers OTX2 and NURR1. In yet another example, the neural progenitors and/or immature midbrain dopaminergic neurons are characterized by the immature midbrain dopaminergic neuron markers MASH1 and NURR1. In a further example, the neural progenitors and/or immature midbrain dopaminergic neurons are characterized by the immature midbrain dopaminergic neuron marker OTX2 and MASH1.

In one example, the isolated midbrain-like organoid is as disclosed herein, wherein the mature midbrain dopaminergic neurons are characterized by one or more of the following markers: MAP2, tyrosine hydroxylase (TH) and dopamine transporter (DAT). In another example, the mature midbrain dopaminergic neurons are characterized by the marker MAP2. In another example, the mature midbrain dopaminergic neurons are characterized by the marker tyrosine hydroxylase (TH). In yet another example, the mature midbrain dopaminergic neurons are characterized by the marker dopamine transporter (DAT). In yet another example, the mature midbrain dopaminergic neurons are characterized by the markers MAP2 and dopamine transporter (DAT). In yet another example, the mature midbrain dopaminergic neurons are characterized by the markers tyrosine hydroxylase (TH) and dopamine transporter (DAT).

In a further example, the mature midbrain dopaminergic neurons are characterized by the markers MAP2 and dopamine transporter (DAT).

In one example, the isolated midbrain-like organoid is as disclosed herein, wherein the mature midbrain dopaminergic neurons are midbrain dopaminergic neurons of the substantia nigra pars compacta (SNpc) (also known as the A9 neurons).

In one example, the isolated midbrain-like organoid is as disclosed herein, wherein the midbrain dopaminergic neurons are capable of producing dopamine, exhibit mature neuronal properties, and/or are able to form synapses with neurons within the midbrain-like organoid.

As used herein, the term "neuromelanin" refers is a dark pigment found in the brain which is structurally related to melanin. Neuromelanin is a polymer of 5,6-dihydroxyindole monomers, and is expressed in large quantities in catecholaminergic cells of the substantia nigra pars compacta and locus coeruleus, giving dark colour to the structures. The pigment is a polymer made out of 5,6-dihydroxyindole, and these monomers is found in higher concentrations among humans than in other primates. Neuromelanin-containing neurons in the substantia nigra undergo neurodegeneration and neuromelanin concentration increases with age, suggesting a role in neuroprotection (neuromelanin can chelate metals and xenobiotics) or senescence. Neuromelanin gives specific brain sections, such as the substantia nigra or the locus coeruleus, distinct colour. It is a type of melanin and similar to other forms of peripheral melanin. It is insoluble in organic compounds, and can be labelled by silver staining. It is called neuromelanin because of its function and the colour change that appears in tissues containing it. It contains black/brown pigmented granules. Neuromelanin is found to accumulate during ageing and is found during the first 2 to 3 years of life. It is believed to protect neurons in the substantia nigra from iron-induced oxidative stress. It is considered a true melanin due to its stable free radical structure and it avidly chelates metals.

Thus, in one example, the isolated midbrain-like organoid is as disclosed herein, and comprise neuromelanin. In another example, the neuromelanin is produced by midbrain dopaminergic neurons. In yet another example, the neuromelanin is accumulated in the substantia nigra.

As uses herein, the term "TGF-β inhibitor" refers to a molecule or compound that is capable of blocking or down regulating the effect of TGF-3. TGF-β is a polypeptide member of the transforming growth factor beta superfamily of cytokines. It is a secreted protein that performs many cellular functions, including, but not limited to, the control of cell growth, cell proliferation, cell differentiation and apoptosis. In humans, TGF-β1 is encoded by the TGFB1 gene. Other members of this superfamily include, but are not limited to, bone morphogenetic proteins (BMPs), growth and differentiation factors (GDFs), anti-müllerian hormone (AMH), Activin (for example, Activin A, B and AB), Nodal and different TGF-β's (for example, TGFβ-1, TGFβ-2, TGFβ-3).

TGF-β and the related proteins of said transforming growth factor beta superfamily of cytokines are involved in the so-called TGF-β signalling pathway. This pathway is involved in many cellular processes in both the adult organism and the developing embryo, including, but not limited to, cell growth, cell differentiation, apoptosis, cellular homeostasis and other cellular functions. In spite of the wide range of cellular processes that the TGF-β signalling pathway regulates, the process is relatively straightforward. TGF-β superfamily ligands bind to a type II receptor (usually a serine/threonine receptor kinase), which recruits and phosphorylates a type I receptor. The type I receptor then phosphorylates receptor-regulated SMADs (R-SMADs) which can now bind the co-SMAD SMAD4 (also known as SMAD family member no 4, Mothers against decapentaplegic homolog 4, JIP, MADH4, MYHRS, or DPC4 (Deleted in Pancreatic Cancer-4)). R-SMAD/co-SMAD complexes accumulate in the nucleus where they act as transcription factors and participate in the regulation of target gene expression.

Thus, in one example, the TGF-β inhibitor is characterized by at least one or more of the following characteristics, which are, but are not limited to, inhibition of TGF-β type I receptor ALK5 kinase; inhibition of type I Activin/Nodal receptor ALK4; inhibition of type I Nodal receptor ALK7; inhibition of SMAD2/3 phosphorylation; and/or inhibition of the Activin/TGF β/SMAD signalling pathway.

In one example, the TGF-β inhibitor is, but is not limited to, A83-01 3-(6-Methyl-2-pyridinyl)-N-phenyl-4-(4-quinolinyl)-1H-pyrazole-1-carbothioamide, A 77-01 4-(3-(6-methylpyridin-2-yl)-1H-pyrazol-4-yl)quinoline, SD-208 2-(5-chloro-2-fluorophenyl)-N-pyridin-4-ylpteridin-4-amine, LY2157299 4-[2-(6-methylpyridin-2-yl)-5,6-dihydro-4H-pyrrolo[1,2-b]pyrazol-3-yl]quinoline-6-carboxamide, SB 431542 4-[4-(1,3-benzodioxol-5-yl)-5-pyridin-2-yl-1H-imidazol-2-yl]benzamide, GW788388 N-(oxan-4-yl)-4-[4-(5-pyridin-2-yl-1H-pyrazol-4-yl)pyridin-2-yl]benzamide, SB505124 2-[4-(1,3-benzodioxol-5-yl)-2-tert-butyl-1H-imidazol-5-yl]-6-methylpyridine, SB525334 6-[2-tert-butyl-5-(6-methylpyridin-2-yl)-1H-imidazol-4-yl]quinoxaline, IN 1130 2-[3-[(4-amino-2-methylpyrimidin-5-yl)methyl]-4-methyl-1,3-thiazol-3-ium-5-yl]ethanol, ITD 1 (6,6-dimethyl-5,7-dihydroimidazo[2,1-b][1,3]thiazol-4-ium-3-yl)methyl N,N'-dicyclohexylcarbamimidothioate, LY2109761 4-[2-[4-(2-pyridin-2-yl-5,6-dihydro-4H-pyrrolo[1,2-b]pyrazol-3-yl)quinolin-7-yl]oxyethyl]morpholine, K02288 3-[6-amino-5-(3,4,5-trimethoxyphenyl)pyridin-3-yl]phenol, TGF-1 RI kinase inhibitor [3-(Pyridin-2-yl)-4-(4-quinonyl)]-1H-pyrazole] or derivatives thereof.

In one example, the TGF-β inhibitor is provided at a concentration of between about 0.5 nM to about 100 μM, or between about 1 nM to about 90 μM, or between about 2 nM to about 80 μM, or between about 3 nM to about 70 μM, or between about 4 nM to about 60 μM, or between about 5 nM to about 50 μM, or between about 10 nM to about 40 μM, or between about 20 nM to about 30 μM, or between about 30 nM to about 20 μM, or between about 40 nM to about 10 μM, or between about 50 nM to about 5 μM, or between about 100 nM to about 2 μM, or between about 200 nM to about 1 μM, or between about 300 nM to about 800 nM, or between about 500 nM to about 700 nM, or about 1 nM, 5 nM, 10 nM, 15 nM, 20 nM, 25 nM, 30 nM, 35 nM, 40 nM, 45 nM, 50 nM, 75 nM, 100 nM, 150 nM, 200 nM, 250 nM, 300 nM, 400 nM, 500 nM, 600 nM, 700 nM, 800 nM, 900 nM, or about 1 μM, 2 μM, 3 μM, 4 μM, 5 μM, 7.5 μM, 10 μM, 12.5 μM, 15 μM, 17.5 μM or 20 μM.

As used herein, the term "SMAD" refers to intracellular proteins that transduce extracellular signals from transforming growth factor beta (TGF-β) ligands to the nucleus where they activate downstream gene transcription. The SMADs, which form a trimer of two receptor-regulated SMADs and one co-SMAD, act as transcription factors that regulate the expression of certain genes. Other SMAD proteins are, but are not limited to, SMAD1, SMAD2 (also known as Mothers against decapentaplegic homolog 2, JV18, JV18-1, MADH2, MADR2, hMAD-2, or SMAD family member 2), SMAD3 (also known as Mothers against decapentaplegic homolog 3, HSPC193, HsT17436, JV15-2, LDS1C, LDS3, MADH3, or SMAD family member 3), SMAD4 (a common-mediator SMAD (co-SMAD), also known as SMAD family member no 4, Mothers against decapentaplegic homolog 4, JIP, MADH4, MYHRS, or DPC4 (Deleted in Pancreatic Cancer-4)), SMAD5 (also known as Mothers against decapentaplegic homolog 5, DWFC, JV5-1, MADH5, or SMAD family member 5), SMAD6 (an antagonistic or inhibitory SMAD, which blocks activation of R-SMADs and co-SMADs; also known as AOVD2, HsT17432, MADH6, MADH7, SMAD family member 6), SMAD7 (an antagonistic or inhibitory SMAD, which blocks activation of R-SMADs and co-SMADs; also known as CRCS3, Mothers against decapentaplegic homolog 7 (MADH7), MADH8, SMAD family member 7), and SMAD8/9 (also known as Mothers against decapentaplegic homolog 9, SMAD9, SMAD8, MADH9, PPH2, SMAD8, SMAD8A, SMAD8B, SMAD family member 9 or MADH6). Thus, as used herein, the term "SMAD inhibitor" refers to a compound of molecule capable of inhibiting (that is preventing or downregulating) the activity of a SMAD protein.

Thus, in one example, the SMAD2/3 inhibitor is, but is not limited to, a SMAD2/3 phosphorylation inhibitor and a siRNA targeting the mRNA of SMAD2 and SMAD3 transcript.

In one example, the SMAD2/3 inhibitor is provided at a concentration of between about 0.5 nM to about 100 µM, or between about 1 nM to about 90 µM, or between about 2 nM to about 80 µM, or between about 3 nM to about 70 µM, or between about 4 nM to about 60 µM, or between about 5 nM to about 50 µM, or between about 10 nM to about 40 µM, or between about 20 nM to about 30 µM, or between about 30 nM to about 20 µM, or between about 40 nM to about 10 µM, or between about 50 nM to about 5 µM, or between about 100 nM to about 2 µM, or between about 200 nM to about 1 µM, or between about 300 nM to about 800 nM, or between about 500 nM to about 700 nM, or about 1, 5, 10, 15, 20, 25, 30, 35, 40, 45, 50, 75, 100, 150, 200, 250, 300, 400, 500, 600, 700, 800, 900 nM, or about 1, 2, 3, 4, 5, 7.5, 10, 12.5, 15, 17.5, 20 µM As used herein, the term "Wnt" refers to the so-called Wnt-signalling pathways, a group of signal transduction pathways made of proteins that pass signals into a cell through cell surface receptors. Three Wnt signalling pathways have been characterized: the canonical Wnt pathway, the non-canonical planar cell polarity pathway, and the non-canonical Wnt/calcium pathway. All three pathways are activated by binding a Wnt-protein ligand to a Frizzled family receptor, which passes the biological signal to the Dishevelled protein inside the cell. The canonical Wnt pathway leads to regulation of gene transcription. The non-canonical planar cell polarity pathway regulates the cytoskeleton that is responsible for the shape of the cell. The non-canonical Wnt/calcium pathway regulates calcium inside the cell. Wnt signalling pathways use either nearby cell-cell communication (paracrine) or same-cell communication (autocrine). Wnt signalling pathways are highly evolutionarily conserved in animals, meaning they are similar across animal species from fruit flies to humans.

Wnt signalling was first identified for its role in carcinogenesis, then for its function in embryonic development. The embryonic processes it controls include, but are not limited to, body axis patterning, cell fate specification, cell proliferation and cell migration. These processes are necessary for proper formation of important tissues including bone, heart and muscle. Its role in embryonic development was discovered when genetic mutations in Wnt pathway proteins produced abnormal fruit fly embryos. Wnt signalling also controls tissue regeneration, for example, in adult bone marrow, skin and intestine.

As used herein, the term "GSK-3" refers to glycogen synthase kinase 3, a serine/threonine protein kinase that mediates the addition of phosphate molecules onto serine and threonine amino acid residues. In mammals, the GSK-3 protein is encoded by two known genes, GSK-3 alpha (GSK3A) and GSK-3 beta (GSK3B).

As used herein, the term "Wnt-signalling activator" refers to a molecule or compound which activates or upregulates genes involved in the Wnt signalling pathway.

Therefore, in one example, the WNT-signalling activator is, but is not limited to, 2-Amino-4-[3,4-(methylenedioxy) benzylamino]-6-(3-methoxyphenyl)pyrimidine (CAS no. 853220-52-7), (1-(4-(Naphthalen-2-yl)pyrimidin-2-yl)piperidin-4-yl)methanamine (WAY 262611 or DKK1 inhibitor), WAY-316606 (5-(Phenylsulfonyl)-N-4-piperidinyl-2-(trifluoromethyl)benzene sulfonamide hydrochloride), heteroarylpyrimidines, arylpyrimidines, IQ1 (2-[2-(4-Acetylphenyl)diazenyl]-2-(3,4-dihydro-3,3-dimethyl-1 (2H)-isoquinolinylidene)acetamide; CAS no. 331001-62-8), QS11 ((2S)-2-[2-(Indan-5-yloxy)-9-(1,1'-biphenyl-4-yl) methyl)-9H-purin-6-ylamino]-3-phenyl-propan-1-ol; CAS no. 944328-88-5), SB-216763 (3-(2,4-dichlorophenyl)-4-(1-methylindol-3-yl)pyrrole-2,5-dione), BIO(6-bromoindirubin-3'-oxime), deoxycholic acid (DCA), 2-amino-4-[3,4-(methylenedioxy)benzyl-amino]-6-(3-methoxyphenyl) pyrimidine, or derivatives thereof.

In another example, the WNT-signalling activator is a GSK3 inhibitor. In yet another example, the GSK3 inhibitor is, but is not limited to, CHIR-99021 (6-[2-[[4-(2,4-dichlorophenyl)-5-(5-methyl-1H-imidazol-2-yl)pyrimidin-2-yl] amino]ethylamino]pyridine-3-carbonitrile), BIO(6-bromoindirubin-3'-oxime), SB 216763 (3-(2,4-dichlorophenyl)-4-(1-methylindol-3-yl)pyrrole-2,5-dione), CHIR-98014 (6-N-[2-[[4-(2,4-dichlorophenyl)-5-imidazol-1-ylpyrimidin-2-yl]amino]ethyl]-3-nitropyridine-2,6-diamine), TWS119 (3-[[6-(3-aminophenyl)-7H-pyrrolo[2,3-d]pyrimidin-4-yl]oxy]phenol), IM-12 (3-[2-(4-fluorophenyl)ethylamino]-1-methyl-4-(2-methyl-1H-indol-3-yl)pyrrole-2,5-dione), 1-azakenpaullone 9-bromo-7,12-dihydropyrido[3', 2':2,3]azepino[4,5-b]indol-6(5H)-one, AR-A014418 1-[(4-methoxyphenyl)methyl]-3-(5-nitro-1,3-thiazol-2-yl)urea, SB415286 3-(3-chloro-4-hydroxyanilino)-4-(2-nitrophenyl) pyrrole-2,5-dione, AZD1080 (3E)-3-[5-(morpholin-4-ylmethyl)-1H-pyridin-2-ylidene]-2-oxo-1H-indole-5-carbonitrile, AZD2858 3-amino-6-[4-(4-methylpiperazin-1-yl) sulfonylphenyl]-N-pyridin-3-ylpyrazine-2-carboxamide, indirubin (3E)-3-(3-oxo-1H-indol-2-ylidene)-1H-indol-2-one or derivatives thereof.

In one example, the WNT-signalling activator is at a concentration of between about 0.5 nM to about 100 µM, or between about 1 nM to about 90 µM, or between about 2 nM to about 80 µM, or between about 3 nM to about 70 µM, or between about 4 nM to about 60 µM, or between about 5 nM to about 50 µM, or between about 10 nM to about 40 µM, or between about 20 nM to about 30 µM, or between about 30 nM to about 20 µM, or between about 40 nM to about 10 µM, or between about 50 nM to about 5 µM, or between about 100 nM to about 2 µM, or between about 200 nM to about 1 µM, or between about 300 nM to about 800 nM, or between about 500 nM to about 700 nM, or about 1, 5, 10, 15, 20, 25, 30, 35, 40, 45, 50, 75, 100, 150, 200, 250, 300, 400, 500, 600, 700, 800, 900 nM, or about 1, 2, 3, 4, 5, 7.5, 10, 12.5, 15, 17.5 or 20 µM.

As used herein, the term "hedgehog signalling protein" refers to a protein that plays a role in the so-called hedgehog signalling pathway. The Hedgehog signalling pathway is a signalling pathway via which cell differentiation information is transmitted to embryonic cells. Different parts of the embryo have different concentrations of hedgehog signalling proteins. The pathway also has roles in the adult. Diseases associated with a malfunction of this pathway are also know, and include, but are not limited to, basal cell carcinoma.

The Hedgehog signalling pathway is one of the key regulators of animal development and is present in all bilaterians (that is, animals with a bilateral symmetry). The pathway takes its name from its polypeptide ligand, an intercellular signalling molecule called Hedgehog (Hh), found in fruit flies of the genus Drosophila. Hh is one of Drosophila's segment polarity gene products, involved in establishing the basis of the fly body plan. The molecule remains important during later stages of embryogenesis and metamorphosis.

There are currently three Hedgehog homologues known in mammals, Desert (DHH), Indian (IHH), and Sonic (SHH), of which Sonic is the best studied. The pathway is equally important during vertebrate embryonic development and is therefore of interest in evolutionary developmental biology. It has been shown in knockout mice lacking components of the pathway that the brain, skeleton, musculature, gastrointestinal tract and lungs fail to develop correctly. Recent studies point to the role of Hedgehog signalling in regulating adult stem cells involved in maintenance and regeneration of adult tissues. The pathway has also been implicated in the development of some cancers.

Thus, in one example, the hedgehog signalling protein is, but is not limited to, Desert hedgehog homolog (DHH), Indian hedgehog homolog (IHH) or Sonic hedgehog (SHH).

In one example, the hedgehog signalling protein is at a concentration of between about 0.5 nM to about 100 μM, or between about 1 nM to about 90 μM, or between about 2 nM to about 80 μM, or between about 3 nM to about 70 μM, or between about 4 nM to about 60 μM, or between about 5 nM to about 50 μM, or between about 10 nM to about 40 μM, or between about 20 nM to about 30 μM, or between about 30 nM to about 20 μM, or between about 40 nM to about 10 μM, or between about 50 nM to about 5 μM, or between about 100 nM to about 2 μM, or between about 200 nM to about 1 μM, or between about 300 nM to about 800 nM, or between about 500 nM to about 700 nM, or about 1, 5, 10, 15, 20, 25, 30, 35, 40, 45, 50, 75, 100, 150, 200, 250, 300, 400, 500, 600, 700, 800, 900 nM, or about 1, 2, 3, 4, 5, 7.5, 10, 12.5 μM, 15 μM, 17.5 μM or 20 μM.

As used herein, the term "fibroblast growth factor" refers to a family of growth factors, with members involved in angiogenesis, wound healing, embryonic development and various endocrine signalling pathways. The fibroblast growth factors are heparin-binding proteins and interactions with cell-surface-associated heparan sulfate proteoglycans have been shown to be essential for fibroblast growth factor signal transduction. Fibroblast growth factors are key players in the processes of proliferation and differentiation of wide variety of cells and tissues. Fibroblast growth factors are multifunctional proteins with a wide variety of effects; they are most commonly mitogens but also have regulatory, morphological, and endocrine effects. They have been alternately referred to as "pluripotent" growth factors and as "promiscuous" growth factors due to their multiple actions on multiple cell types. Promiscuous refers to the biochemistry and pharmacology concept of how a variety of molecules can bind to and elicit a response from single receptor. In the case of fibroblast growth factor, four receptor subtypes can be activated by more than twenty different fibroblast growth factor ligands. Thus the functions of FGFs in developmental processes include mesoderm induction, antero-posterior patterning, limb development, neural induction and neural development, and in mature tissues/systems angiogenesis, keratinocyte organization, and wound healing processes.

Fibroblast growth factors are critical during normal development of both vertebrates and invertebrates and any irregularities in their function leads to a range of developmental defects. Fibroblast growth factors secreted by hypoblasts during avian gastrulation play a role in stimulating a Wnt signalling pathway that is involved in the differential movement of Koller's sickle cells during formation of the primitive streak. One important function of FGF1 and FGF2 is the promotion of endothelial cell proliferation and the physical organization of endothelial cells into tube-like structures. They thus promote angiogenesis, the growth of new blood vessels from the pre-existing vasculature. FGF1 and FGF2 are more potent angiogenic factors than vascular endothelial growth factor (VEGF) or platelet-derived growth factor (PDGF). FGF1 has been shown in clinical experimental studies to induce angiogenesis in the heart. As well as stimulating blood vessel growth, fibroblast growth factors are important players in wound healing. FGF1 and FGF2 stimulate angiogenesis and the proliferation of fibroblasts that give rise to granulation tissue, which fills up a wound space/cavity early in the wound-healing process. FGF7 and FGF10 (also known as keratinocyte growth factors KGF and KGF2, respectively) stimulate the repair of injured skin and mucosal tissues by stimulating the proliferation, migration and differentiation of epithelial cells, and they have direct chemotactic effects on tissue remodelling. During the development of the central nervous system, fibroblast growth factors play important roles in neural stem cell proliferation, neurogenesis, axon growth, and differentiation. Fibroblast growth factor signalling is important in promoting surface area growth of the developing cerebral cortex by reducing neuronal differentiation and hence permitting the self-renewal of cortical progenitor cells, known as radial glial cells, and FGF2 has been used to induce artificial gyrification of the mouse brain. Another fibroblast growth factor family member, FGF8, regulates the size and positioning of the functional areas of the cerebral cortex (Brodmann's Areas). FGFs are also important for maintenance of the adult brain. Thus, fibroblast growth factors are major determinants of neuronal survival both during development and during adulthood. Adult neurogenesis within the hippocampus e.g. depends greatly on FGF2. In addition, FGF1 and FGF2 seem to be involved in the regulation of synaptic plasticity and processes attributed to learning and memory, at least in the hippocampus. The fifteen paracrine fibroblast growth factors are secreted proteins that bind heparan sulfate and can, therefore, be bound to the extracellular matrix of tissues that contain heparan sulfate proteoglycans. This local action of FGF proteins is classified as paracrine signalling, most commonly through the JAK-STAT signalling pathway or the Receptor tyrosine kinase (RTK) pathway.

Members of the FGF19 subfamily (FGF15, FGF19, FGF21, and FGF23) bind less tightly to heparan sulphates, and so can act in an endocrine fashion on far-away tissues, such as intestine, liver, kidney, adipose, and bone.[9] For example, FGF15 and FGF19 (FGF15/19) are produced by intestinal cells but act on FGFR4-expressing liver cells to downregulate the key gene (CYP7A1) in the bile acid synthesis pathway. FGF23 is produced by bone but acts on FGFR1-expressing kidney cells to regulate the synthesis of vitamin D and phosphate homeostasis. In humans, 22 members of the FGF family have been identified, all of which are structurally related signalling molecules. FGF1 through to FGF10 are known to all bind fibroblast growth factor receptors (FGFRs). FGF1 is also known as acidic, and FGF2 is also known as basic fibroblast growth factor. FGF11, FGF12, FGF13, and FGF14, also known as FGF homologous factors 1 to 4 (FHF1-FHF4), have been shown to have distinct functions compared to the FGFs. Although these factors possess remarkably similar sequence homology, they do not bind FGFRs and are involved in intracellular processes unrelated to the FGFs This group is also known as "iFGF". Human FGF18 is involved in cell development and morphogenesis in various tissues including cartilage. Human FGF20 was identified based on its homology to Xenopus FGF-20 (XFGF-20). FGF15 through FGF23 were described later and functions are still being characterized. FGF15 is the mouse ortholog of human FGF19 (there is no human FGF15) and, where their functions are shared, they are often described as FGF15/19.[9] In contrast to the local activity of the other FGFs, FGF15/19, FGF21 and FGF23 have systemic effects. The crystal structures of FGF1 have been solved and found to be related to interleukin 1-beta. Both families have the same beta trefoil fold consisting of 12-stranded beta-sheet structure, with the beta-sheets are arranged in 3 similar lobes around a central axis, 6 strands forming an anti-parallel beta-barrel. In general, the beta-sheets are well-preserved and the crystal structures superimpose in these areas. The intervening loops are less well-conserved—the loop between beta-strands 6 and 7 is slightly longer in interleukin-1 beta.

Thus, in one example, the fibroblast growth factor is, but is not limited to, FGF1, FGF2, FGF3, FGF4, FGF5, FGF6, FGF7, FGF8, FGF9, FGF10, FGF11, FGF12, FGF13, FGF14, and combinations thereof. In another example, the fibroblast growth factor is FGF8.

In one example, the fibroblast growth factor is at a concentration of between about 0.5 nM to about 100 µM, or between about 1 nM to about 90 µM, or between about 2 nM to about 80 µM, or between about 3 nM to about 70 µM, or between about 4 nM to about 60 µM, or between about 5 nM to about 50 µM, or between about 10 nM to about 40 µM, or between about 20 nM to about 30 µM, or between about 30 nM to about 20 µM, or between about 40 nM to about 10 µM, or between about 50 nM to about 5 µM, or between about 100 nM to about 2 µM, or between about 200 nM to about 1 µM, or between about 300 nM to about 800 nM, or between about 500 nM to about 700 nM, or about 1, 5, 10, 15, 20, 25, 30, 35, 40, 45, 50, 75, 100, 150, 200, 250, 300, 400, 500, 600, 700, 800, 900 nM, or about 1, 2, 3, 4, 5, 7.5, 10, 12.5, 15, 17.5 or 20 µM.

As used herein, the term "ECM" or "extracellular matrix" refers to a collection of extracellular molecules secreted by cells that provides structural and biochemical support to the surrounding cells. Because multicellularity evolved independently in different multicellular lineages, the composition of ECM varies between multicellular structures; however, cell adhesion, cell-to-cell communication and differentiation are common functions of the ECM.

Animal extracellular matrix includes the interstitial matrix and the basement membrane. Interstitial matrix is present between various animal cells (i.e., in the intercellular spaces). Gels of polysaccharides and fibrous proteins fill the interstitial space and act as a compression buffer against the stress placed on the extracellular matrix (ECM). Basement membranes are sheet-like depositions of extracellular matrix, on which various epithelial cells rest. Each type of connective tissue in animals has a type of extracellular matrix: collagen fibres and bone mineral comprise the extracellular matrix of bone tissue; reticular fibres and ground substance comprise the extracellular matrix of loose connective tissue; and blood plasma is the extracellular matrix of blood.

The plant extracellular matrix includes cell wall components, like cellulose, in addition to more complex signalling molecules. Some single-celled organisms adopt multicellular biofilms in which the cells are embedded in an extracellular matrix composed primarily of extracellular polymeric substances (EPS). Due to its diverse nature and composition, the extracellular matrix can serve many functions, such as providing support, segregating tissues from one another, and regulating intercellular communication. The extracellular matrix regulates a cell's dynamic behaviour. In addition, it sequesters a wide range of cellular growth factors and acts as local store for them. Changes in physiological conditions can trigger protease activities that cause local release of such stores. This allows the rapid and local growth factor-mediated activation of cellular functions without the requirement of de novo synthesis.

The stiffness and elasticity of the extracellular matrix has important implications in cell migration, gene expression, and differentiation. Cells actively sense extracellular matrix rigidity and migrate preferentially towards stiffer surfaces in a phenomenon called durotaxis. Cells also detect elasticity and can adjust their gene expression. Components of the extracellular matrix are produced intracellularly by resident cells and secreted into the extracellular matrix via exocytosis. Once secreted, they then aggregate with the existing matrix. The extracellular matrix is composed of an interlocking mesh of fibrous proteins and glycosaminoglycans (GAGs). Thus, an extracellular matrix can comprise, but is not limited to, proteoglycans (for example, heparan sulfate, chrondroitin sulfate, keratin sulfate), non-proteoglycan polysaccharides (for example, hyaluronic acid), proteins (for example, collagen, elastin) and other components, such as, but not limited to fibronectin and laminin.

Therefore, in one example, the extracellular matrix promotes cell differentiation and/or can maintain three-dimensional culture and/or promotes the development of complex tissue. Thus, the material(s) from which comprise the extracellular matrix is/are but is/are not limited to, matrigel, gelatine, methylcellulose, collagen, alginate, alginate beads, agarose, fibrin, fibrin glue, fibrinogen, blood plasma fibrin beads, whole plasma or components thereof, laminins, fibronectins, protecogylcans, HSP, chitosan, heparin, other synthetic polymer or polymer scaffolds and solid support materials. In one example, the extracellular matrix is made of matrigel.

As used herein, the term "neurotrophic factor" refers to a family of biomolecules—nearly all of which are either peptides or small proteins—that support the growth, survival, and differentiation of both developing and mature neurons. Most neurotrophic factors exert their trophic effects on neurons by signalling through tyrosine kinases, usually a receptor tyrosine kinase. In the mature nervous system, they promote neuronal survival, induce synaptic plasticity, and modulate the formation of long-term memories. Neurotrophic factors also promote the initial growth and development of neurons in the central nervous system and peripheral nervous system and that they are capable of re-growing damaged neurons in test tubes and animal models. Some neurotrophic factors are also released by the target tissue in order to guide the growth of developing axons. Most neurotrophic factors belong to one of three families: (1) neurotrophins, (2) glial cell-line derived neurotrophic factor family ligands (GFLs), and (3) neuropoietic cytokines. Each family has its own distinct cell signalling mechanisms, although the cellular responses elicited often do overlap.

Thus, in one example, the neurotrophic factor is, but is not limited to neurotrophin, glial cell-line derived neurotrophic factor family ligand (GFL), and neuropoietic cytokine. In another example, the neurotrophin is, but is not limited to, nerve growth factor (NGF), brain-derived neurotrophic factor (BDNF), neurotrophin-3 (NT-3) and neurotrophin-4 (NT-4). In another example, the glial cell-line derived neurotrophic factor family ligand (GFL) is, but is not limited to, glial cell line-derived neurotrophic factor (GDNF), neurturin (NRTN), artemin (ARTN) and persephin (PSPN).

In one example, the neurotrophic factor is at a concentration of between about 0.1 nM to about 100 μM, or between about 0.2 nM to about 90 μM, or between about 0.3 nM to about 80 μM, or between about 0.4 nM to about 70 μM, or between about 0.5 nM to about 60 μM, or between about 0.6 nM to about 50 μM, or between about 0.7 nM to about 40 μM, or between about 0.8 nM to about 30 μM, or between about 0.9 nM to about 20 μM, or between about 1 nM to about 10 μM, or between about 5 nM to about 5 μM, or between about 10 nM to about 4 μM, or between about 20 nM to about 3 μM, or between about 30 nM to about 2 μM, or between about 40 nM to about 1 μM, or between about 50 nM to about 900 nM, or between about 100 nM to about 800 nM, or between about 200 nM to about 700 nM, or between about 300 nM to about 600 nM, or between about 400 nM to about 500 nM, or about 0.1, 0.2, 0.3, 0.4, 0.5, 0.6, 0.7, 0.8, 0.9, 1, 2, 5, 10, 15, 20, 25, 30, 35, 40, 45, 50, 75, 100, 150, 200, 250, 300, 400, 500, 600, 700, 800, 900 nM, or about 1, 2, 3, 4, 5, 7.5, 10, 12.5, 15, 17.5 or 20 μM.

As used herein, the term "ascorbic acid" refers to a vitamin, that is, vitamin C, an organic compound with the formula of $C_6H_8O_6$. It is used in cell culture for the maintenance of healthy cells. Ascorbic acid plays a role of acts as an anti-oxidant in to lower the level of reactive oxygen species which are generated during the differentiation of stem cells.

In one example, the ascorbic acid is at a concentration of between about 1 μM to about 1 mM, or between about 5 μM to about 950 μM, or between about 10 μM to about 900 μM, or between about 20 μM to about 850 μM, or between about 30 μM to about 800 μM, or between about 40 μM to about 750 μM, or between about 50 μM to about 700 μM, or between about 60 μM to about 650 μM, or between about 70 μM to about 600 μM, or between about 80 μM to about 550 μM, or between about 90 μM to about 500 μM, or between about 100 μM to about 450 μM, or between about 125 μM to about 400 μM, or between about 150 μM to about 350 μM, or between about 175 μM to about 300 μM, or between about 200 μM to about 250 μM, or about 1 μM, 2 μM, 3, 4, 5, 7.5, 10, 12.5, 15, 17.5, 20, 25, 30, 35, 40, 45, 50, 55, 60, 65, 70, 75, 80, 85, 90 μM, 95 μM, 100 μM, 125 μM, 150 μM, 175 μM, 200 μM, 250 μM, 300 μM, 400 μM, 500 μM, 600 μM, 700 μM, 800, 900 μM or about 1 mM.

As used herein, the term "activator of cAMP-dependent pathways", also known as the adenylyl cyclase pathway, refers to a G protein-coupled receptor-triggered signalling cascade used in cell communication. In humans, cAMP, which stands for cyclic adenosine monophosphate (also known as cAMP, cyclic AMP, or 3',5'-cyclic adenosine monophosphate; an important second messenger in signalling pathways) works by activating protein kinase A (also known as PKA, cAMP-dependent protein kinase), one of the first few kinases discovered. Protein kinase A has four sub-units, two catalytic subunits and two regulatory sub-units. cAMP binds to the regulatory sub-units of the protein kinase A and causes them to break away from the catalytic subunits. These catalytic sub-units then make their way in to the nucleus, where they have an influence on transcription processes. Further effects of these catalytic subunits depend mainly on the cAMP-dependent protein kinase itself, which varies depending on the type of cell.

cAMP-dependent pathways are necessary for many living organisms and life processes. Many different cell responses are mediated by cAMP. These include, but are not limited to, increase in heart rate, cortisol secretion, and breakdown of glycogen and fat. cAMP is also known for its role in maintaining memory in the brain, relaxation in the heart, and water absorption in the kidney. cAMP-dependent pathways can activate enzymes and regulate gene expression, and can therefore play an integral role in cell differentiation. In terms of diseases, if a cAMP-dependent pathway is not under the proper control, it can ultimately lead to hyperproliferation, which may contribute to the development and/or progression of cancer and any other hyperproliferative diseases.

In one example, the activator of cAMP-dependent pathways is, but is not limited to, dibutyryl-cAMP(dbCAMP), forskolin ((3R,4aR,5S,6S,6aS,10S,10aR,10bS)-6,10,10b-trihydroxy-3,4a,7,7,10a-pentamethyl-1-oxo-3-vinyldodecahydro-1H-benzo[f]chromen-5-yl acetate), caffeine, theophylline, cholera toxin and pertussis toxin.

In one example, the activator of cAMP-dependent pathways is at a concentration of between about 1 μM to about 1 mM, or between about 5 μM to about 950 μM, or between about 10 μM to about 900 μM, or between about 20 μM to about 850 μM, or between about 30 μM to about 800 μM, or between about 40 μM to about 750 μM, or between about 50 μM to about 700 μM, or between about 60 μM to about 650 μM, or between about 70 μM to about 600 μM, or between about 80 μM to about 550 μM, or between about 90 μM to about 500 μM, or between about 100 μM to about 450 μM, or between about 125 μM to about 400 μM, or between about 150 μM to about 350 μM, or between about 175 μM to about 300 μM, or between about 200 μM to about 250 μM, or about 1, 2, 3, 4, 5, 7.5, 10, 12.5, 15, 17.5, 20, 25, 30, 35, 40, 45, 50, 55, 60, 65, 70, 75, 80, 85, 90, 95, 100, 125, 150, 175, 200, 250, 300, 400, 500, 600, 700, 800, 900 μM or about 1 mM.

Methods for cell culture can require agitation of the cells, for example, when the cells are grown in suspension or when scaffolds are used. Thus, in one example, an orbital shaker is used in the culturing of the neuroepithelial tissues suing the methods disclosed herein.

Figure 1:
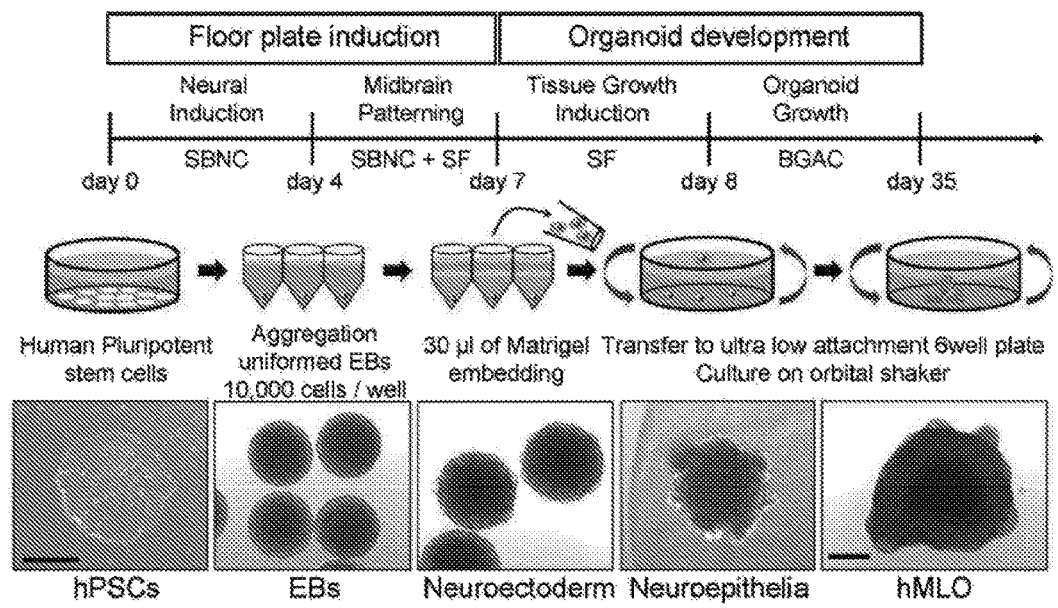
FIG. 1 provides data showing the generation and characterization of human midbrain-like organoids (hMLOs) from human pluripotent stem cells (hPSCs). (A) shows schematic diagrams illustrating the overall strategy to generate human midbrain-like organoids. Differential interference contrast microscopy (DIC) images illustrate the typical morphology of cells at each stage. SBNC: SB431542, Noggin, and CHIR99021; SF: SHH-C25II and FGF8; BGAC: BDNF, GDNF, ascorbic acid, and db-cAMP. Scale bars=500 µm. (B) Left: shows micrograph images of a cryosection of a human midbrain-like organoid at day 35, stained for Ki67 and MAP2. Right: shows micrograph images of a zoom-in view of the white box shown in the left part of the image. Left scale bar=200 µm. Right scale bar=10 µm. (C) shows column graphs showing the quantification of the percentage of Ki67$^+$ and MAP2$^+$ cells present in day 25 and 35 human midbrain-like organoids by fluorescent-activated cell sorting (FACS) analysis. n=3, *p<0.05, as determined using Student's t-test. (D) shows micrographs of immunostaining for EdU, OTX2, and aPKC at the apical region of a neuroepithelium (NE). Scale bar=20 µm. (E) shows column graphs depicting the percentages of OTX2$^+$ and OTX$^+$/EdU$^+$ cells at the apical region of the neuroepithelium (NE); mean±s.e.m. (standard error of the mean), n=7. (F) shows a schematic of the laminar structure in the human midbrain-like organoids (bas.: basal; ap.: apical; MZ: mantle zone; IZ: intermediate zone; VZ: ventral zone). (G) shows a micrograph of a cryosection of a day 35 human midbrain-like organoid stained for MAP2 and MASH1. Scale bar=50 µm. (H) shows a micrograph depicting the EdU labelling and OTX2 immunostaining of a day 35 human midbrain-like organoid. Scale bar=20 µm. (I) shows a micrograph of a cryosection of a day 35 human midbrain-like organoid stained for NURR1 and MASH1. Scale bar=20 µm. (J) shows micrographs of cryosections of a human midbrain-like organoid at days 4, 14, and 24 stained for FOXA2 (floor plate progenitors) and OTX2 (midbrain intermediate progenitors). Scale bars=50 µm. (K) shows a micrograph image depicting the immunostaining of FOXA2 and tyrosine hydroxylase (TH) of a human midbrain-like organoid at day 45. Scale bars=50 µm. The quantification of the staining shown in (K) are shown in the column graphs presented in (L); mean±s.e.m. (standard error of the mean), n=3. (M) shows micrographs of cryosections of a day 45 human midbrain-like organoid labelled for LMX1A and TH. Scale bars=50 µm. The quantification of the labelling of (M) is shown in the column graph presented in (N); mean±s.e.m. (standard error of the mean), n=3. (O) shows micrographs depicting the results of immunostaining of mantle zone (MZ) cells at day 60 with DAT and TH antibodies. The zoom-in view (white boxed area is magnified in the images to the right) to illustrate that some cells were double positive for DAT and TH. The quantification of the immunostaining presented in (O) are shown in the column graph presented in (P); mean±s.e.m. (standard error of the mean), n=3. Scale bar=20 µm.
Figure 1:
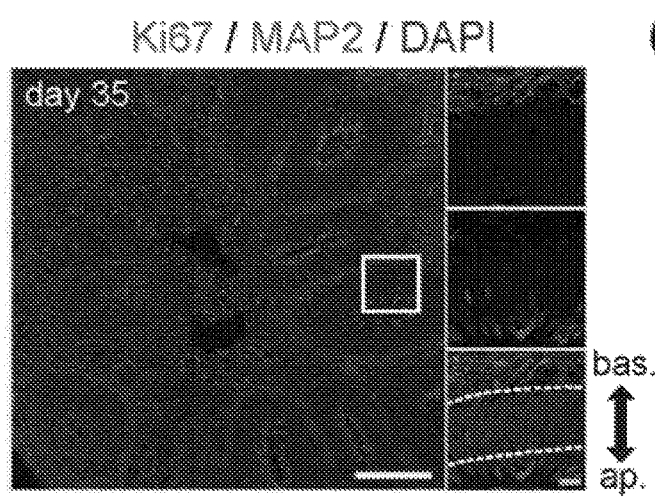
Figure 1:
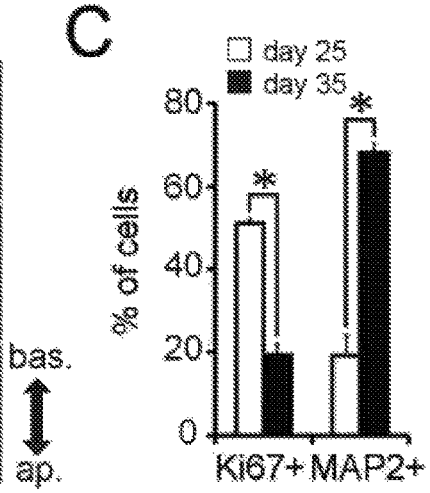
Figure 1:
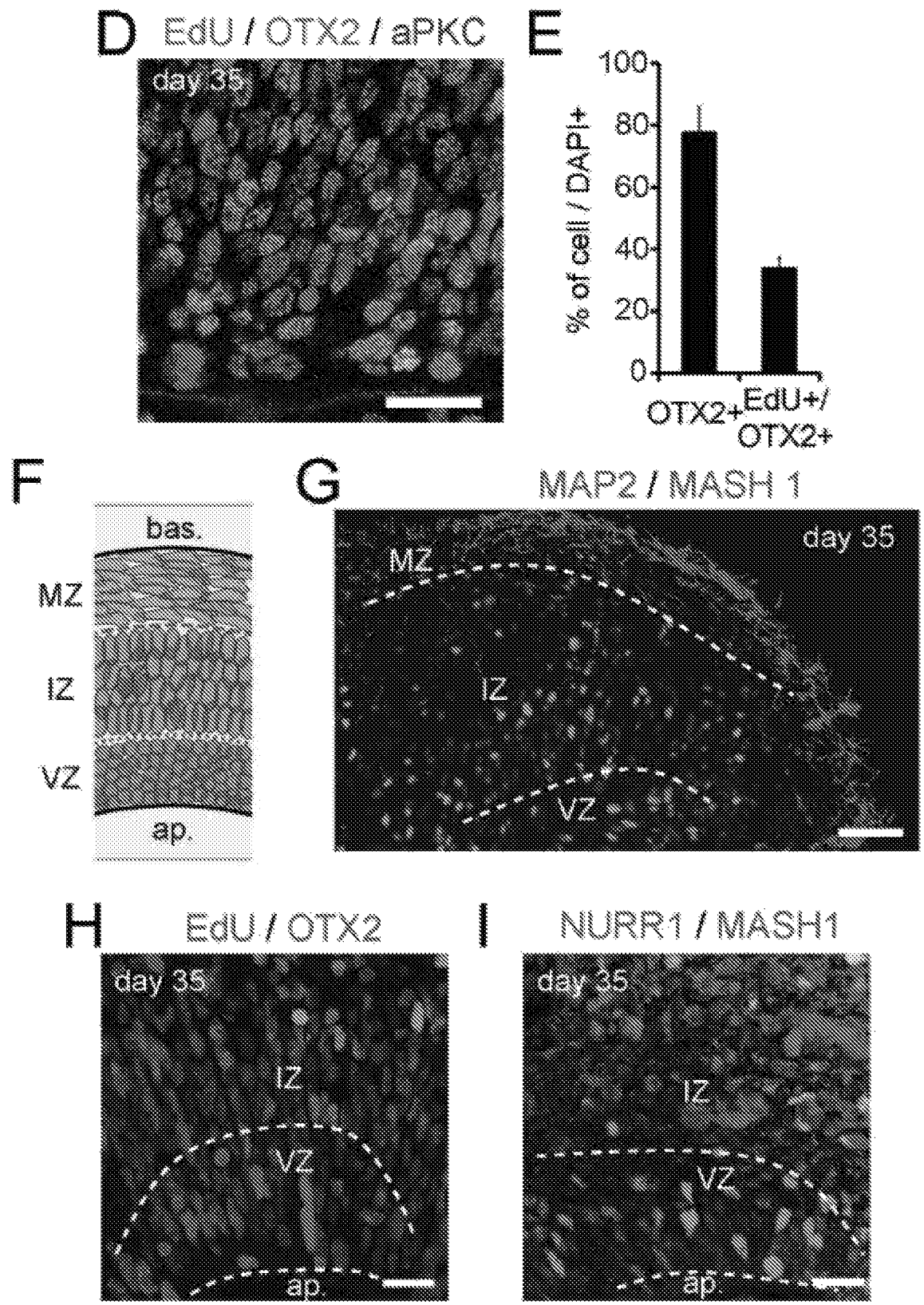
Figure 1:
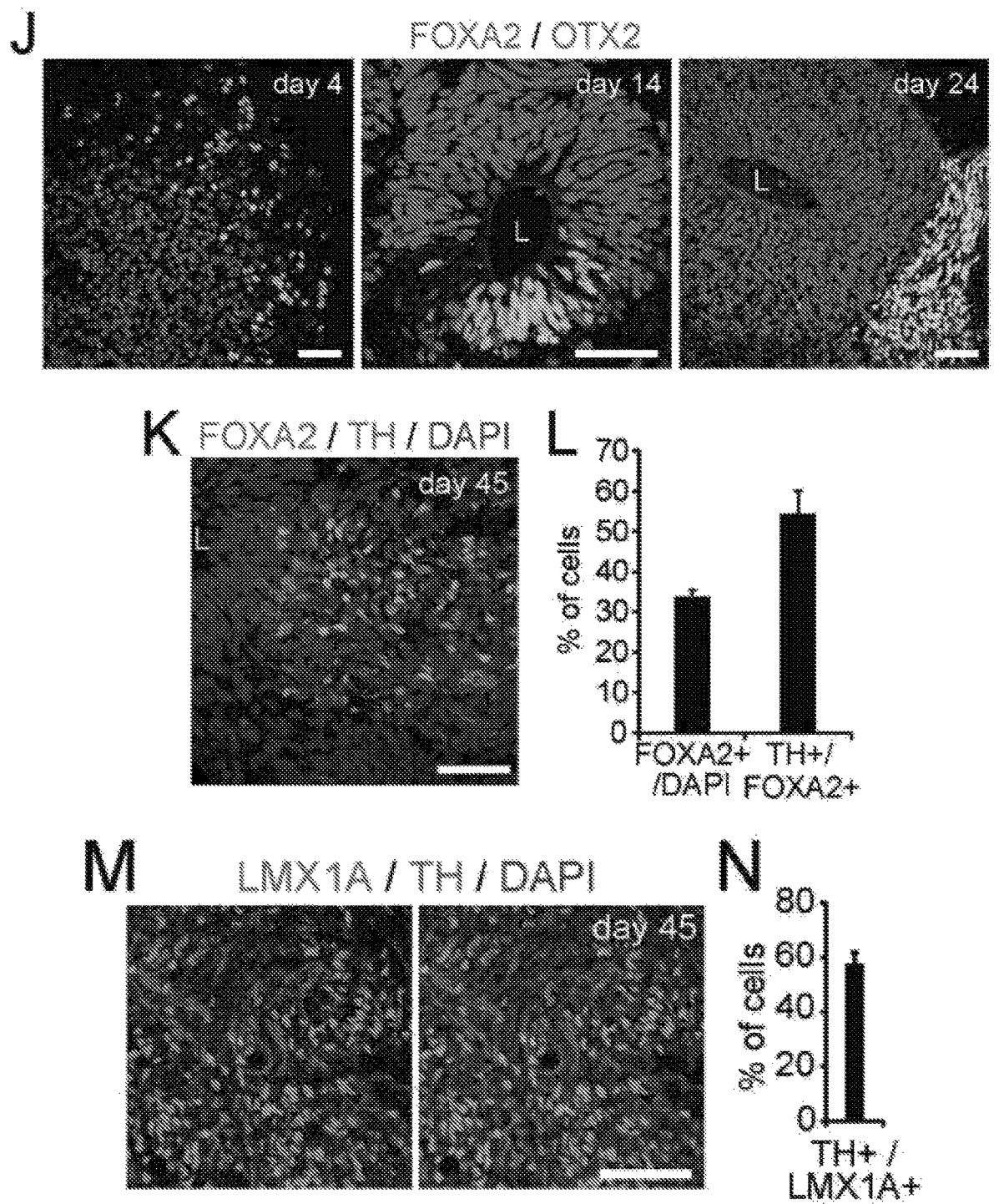
Figure 1:
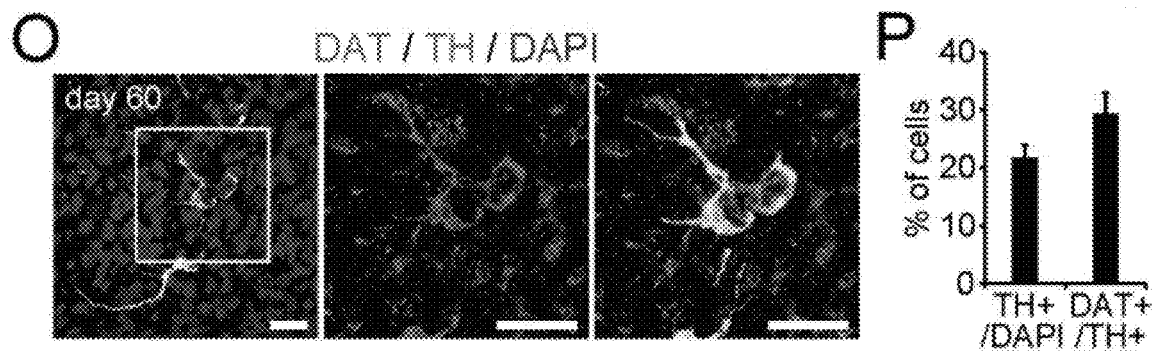

Generation and Characterization of Human Mid-Brain Like Organoids from Human Pluripotent Stem Cells In the present disclosure, a self-organizing principle was applied to human embryonic stem cell (hESC) culture and generated midbrain dopaminergic neuron-containing human midbrain-like organoids (hMLOs) in the absence of extracellular scaffolding. First, human embryonic stem cells were dissociated to single cells and allowed to form uniform-sized (approximately 400 μm), embryoid bodies (EBs) in low-attachment V-shaped 96-well dishes (FIG. 1A). To inhibit mesenchymal differentiation and promote neuroectodermal differentiation, these embryoid bodies were simultaneously subjected to DUAL-SMAD inhibition factors (Noggin and SB431542) and Wnt pathway activator (CHIR99021). The resulting embryoid bodies underwent a mesencephalic fate for 4 days. Sonic hedgehog and FGF8 were added to the embryoid body cultures for an additional 3 days. After neural induction and midbrain patterning, neural organoids gave rise midbrain dopaminergic progenitors as indicated by immunostaining of mDA progenitor markers including PAX6, CORIN, and FOXA1 (FIGS. 5A, B, and C) as well as by gene expression profiles (FIGS. 5D and E). Subsequently, each neuroectodermal spheroid was embedded with matrigel with reduced amounts of growth factors to provide 3D environment overnight, and was subsequently transferred to a tissue culture dish placed on an orbital shaker in neuronal media that was supplemented with neurotrophic factors such as BDNF and GDNF until the day of analysis. The use of an orbital shaker greatly improved viability, survival, and differentiation of neural organoids (data not shown). These neural organoids grew in size of more than 2000 μm in diameter by 30 days and showed multiple neuroepithila (FIGS. 1A, and 5F and G). Next, cryosectioning was performed to characterize human midbrain-like organoids and observed that neuroepithelia of human midbrain-like organoids exhibited an apical-basal polarity based on the localization of atypical protein kinase C (aPKC), an apical marker protein (FIG. 5H). Ki67-positive proliferating cells were also detected at the apical surface of neuroepithelia, but MAP2-positive neurons were observed at the basal surface of neuroepithelia (FIG. 1B). Flow cytometry analysis further revealed that, at day 25, 51% of cells were positive for Ki67, a cellar marker for proliferation, but only 19% of cells were positive for Ki67 at day 35, indicating that the proportion of progenitors decreases upon human midbrain-like organoid maturation (FIG. 1C). Accordingly, the proportion of MAP2-positive cells within human midbrain-like organoids increased to 3.6 folds, which correlated with increased size of the MAP2-positive cell-containing layer (FIG. 1C). These data indicated that cells in human midbrain-like organoids were gradually changed from neuroprogenitors to more mature neurons. To further characterize developing midbrain neuroepithelia, proliferating progenitor cells were labelled with EdU and staining against OTX2, a transcription factor that guides and separates midbrain from the hindbrain, was performed. The expression of OTX2 emerged from cells within apical surface and extended to the intermediate region of neuroepithlia within a human midbrain-like organoids (FIGS. 1D and 5II), and approximately 35% of cells within this area were double positive for both EdU and OTX2 (FIG. 1E). This result demonstrated that proliferating cells near the apical region of human midbrain-like organoids are midbrain progenitors. Next, the cytoarchitecture of neural organoids was further analysed at 35 days by immunostaining using antibodies against markers of distinct cell types. Similar to the layering of the murine embryonic midbrain floor plate that eventually gives rise to mDA neurons, human midbrain-like organoids at 35 days show three layers: proliferative ventral zone (VZ) where neural progenitors reside, the intermediate zone (IZ), a layer that immature mDA neurons pass through as they migrate ventrally, and the mantle zone (MZ), where maturing mDA neurons begin to express the genes associated with the synthesis of dopamine (FIG. 1F). In the VZ and IZ, midbrain progenitors expressed MASH1 and OTX2 (FIGS. 1G and H). The orphan nuclear receptor NURR1, which were expressed in post-mitotic mDA progenitors, was detected in the IZ (FIG. 1I). This data indicates that the presented in vitro human midbrain-like organoid culture system results in organoids that are reminiscent of early in vivo midbrains that enlarge through the differentiation of neuroprogenitors in multiple laminated layers with distinct apical-basal polarization.

Figure 2:
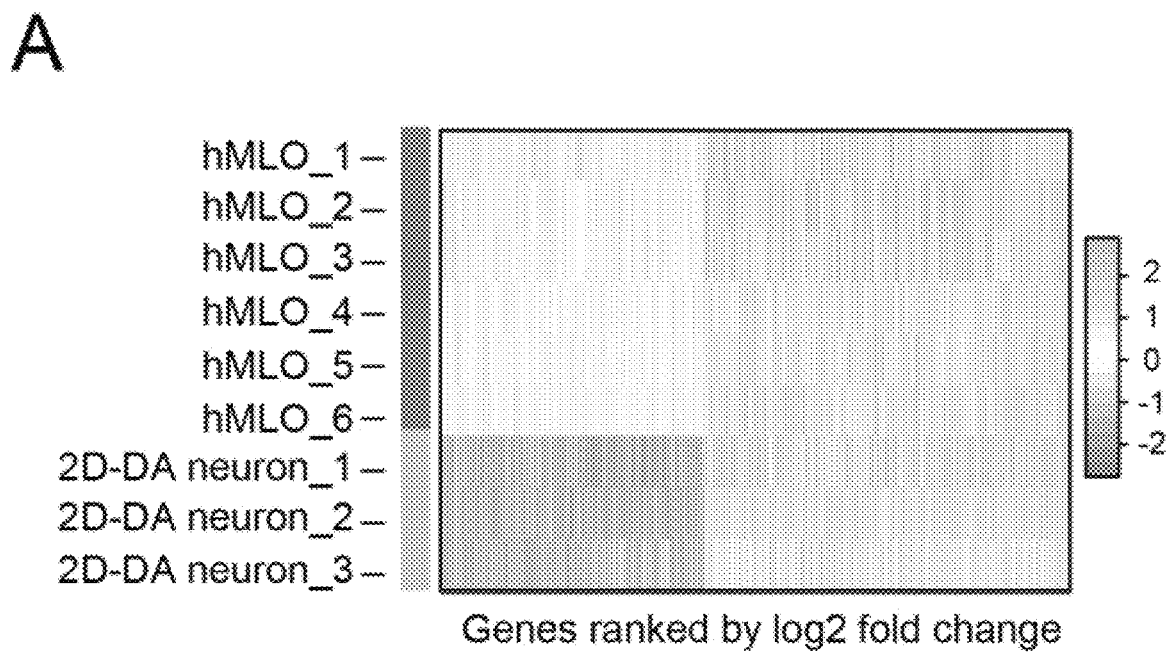
FIG. 2 shows the results of the transcriptional characterization of human midbrain-like organoids (hMLOs). (A) shows a heat map showing differentially expressed genes between two-dimensional dopaminergic neurons (2D-DA) neurons and human midbrain-like organoids, sorted by fold change. (B) shows a heat map and the clustering of expression data from two-dimensional dopaminergic neurons (2D-DA) neurons, human midbrain-like organoids (hMLOs), and prenatal midbrain. The correlation of normalised gene expression using differentially expressed genes between 2D-DA neurons and human midbrain-like organoids was used to estimate the distance between samples. (C) shows a Venn Diagram indicating the overlap of genes that show up- or downregulation in human midbrain-like organoids and prenatal midbrain compared to 2D-DA neurons. (Statistical significance was estimated using Fisher's exact test). (D) shows a heat map showing genes that are differentially expressed between 2D-DA neurons and human midbrain-like organoids and human prenatal midbrain, sorted by fold change (E) shows spectra of example genes expressed in prenatal midbrain and hMLOs, but not in 2D-DA neurons, and the spectra shown in (F) are example genes commonly expressed in prenatal midbrain, human midbrain-like organoids, and 2D-DA neurons. The expression levels of the example genes are measured by RNA sequencing. The Y-axis represents the normalized number of reads. The black area indicates normalized read count and the grey area indicates split reads that map onto two exons.
Figure 2:
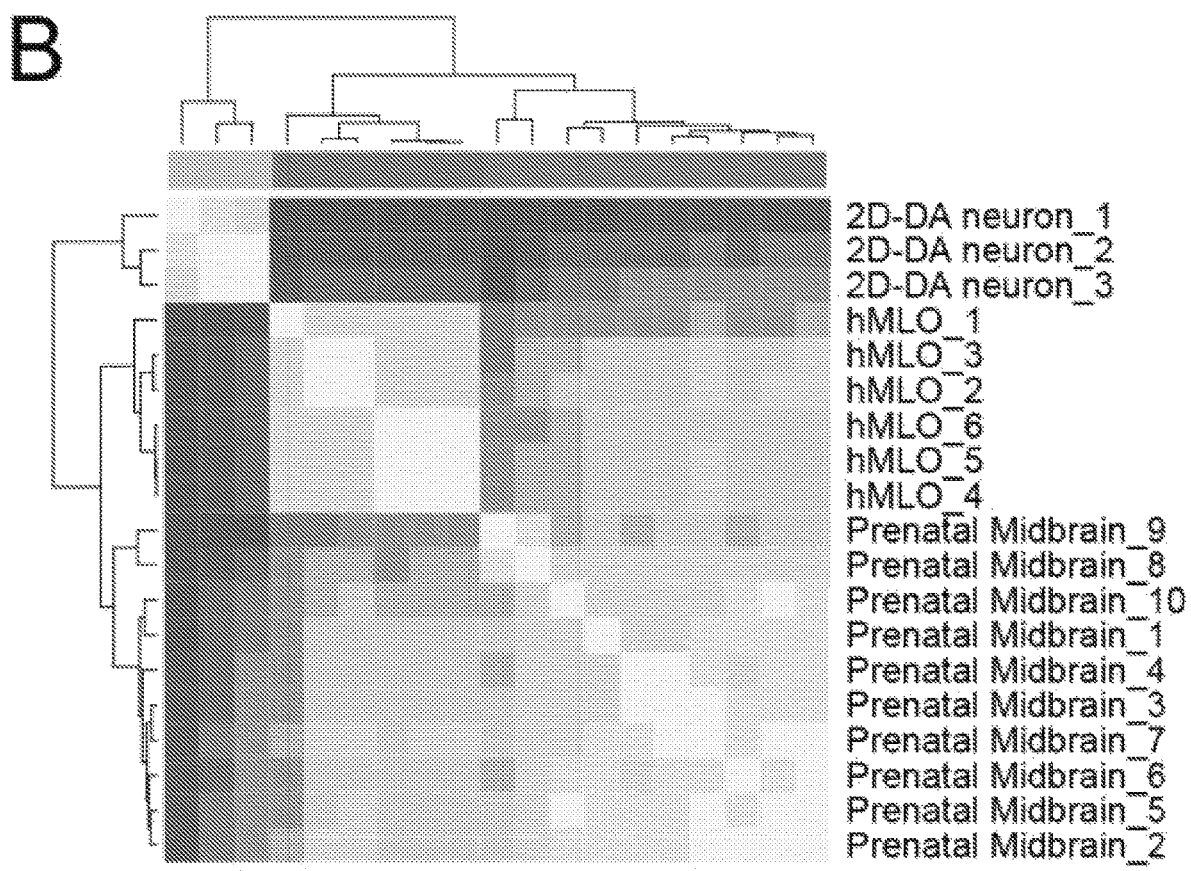
Figure 2:
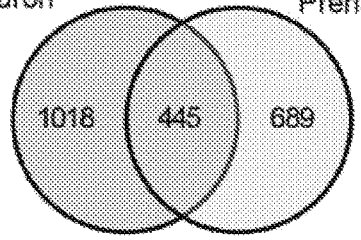
Figure 2:
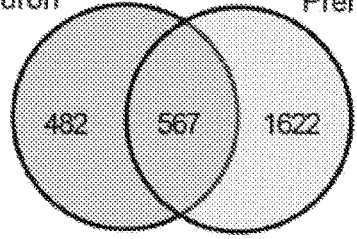
Figure 2:
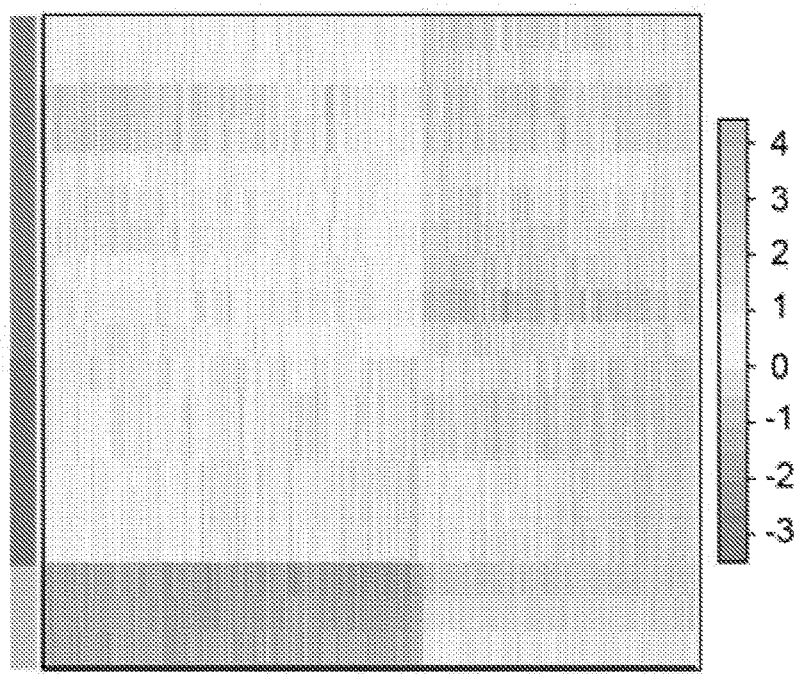
Figure 2:
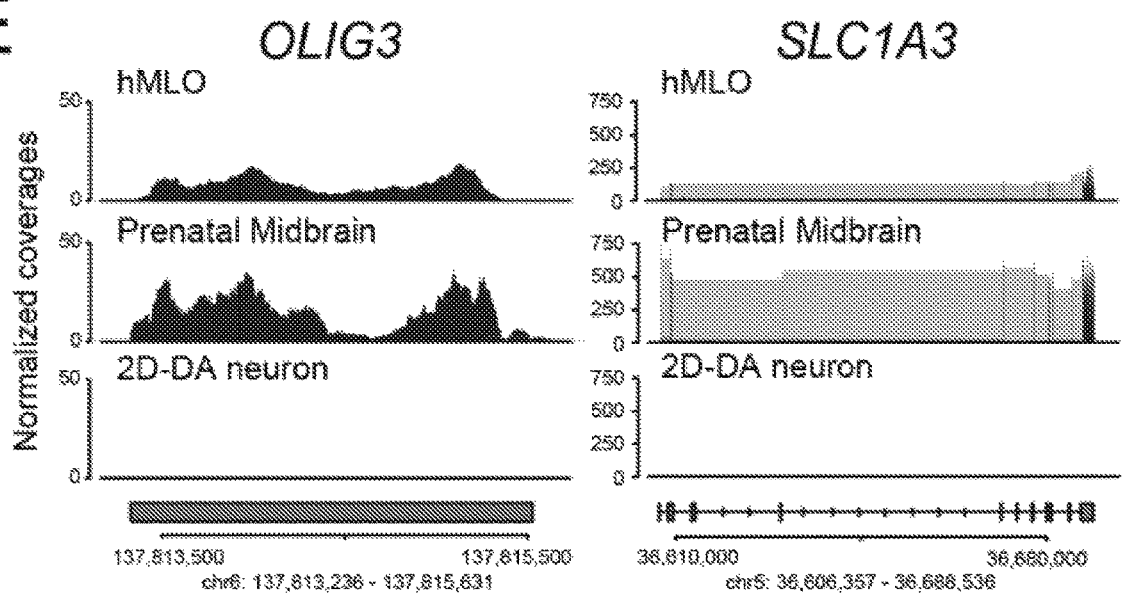
Figure 2:
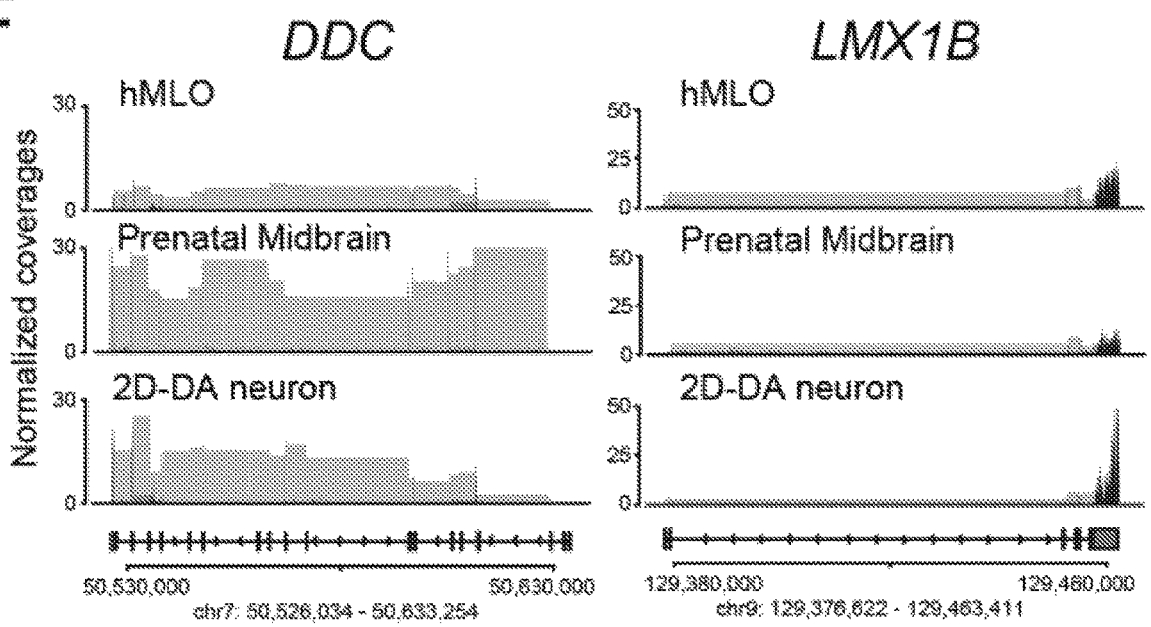

Identification and Verification of A9 mDA Neurons in Human Midbrain-Like Organoids Human midbrain-like organoids grows exponentially in size, presumably via increasing neuroprogenitors and neuroprogenitor-derived mature neurons at MZ (FIG. 5G). At the MZ, labelled by mature neuron marker MAP2, neurons started to express tyrosine hydroxylase (TH), a major marker for midbrain dopaminergic (mDA) neurons (FIG. 2A).

To further quantify neuronal populations within the generated human midbrain-like organoids, human midbrain-like organoids were dissociated into single-cell suspension and were subjected to flow cytometry analysis. Interestingly, 15% of MAP2-positive mature neurons co-expressed TH, indicating that mature neurons at the MZ were indeed mDA neurons (FIG. 2B). This data indicates that the neural organoids at 35 days were organized similarly to early midbrain floor plate that contains three layers of distinct neuronal populations including DA progenitors, intermediate progenitors, and mDA neurons. Indeed, at day 60, TH-positive neurons within the MZ of human midbrain-like organoids express mDA neuronal marker DAT (FIGS. 2C and D).

There are two major subtypes of mDA neurons: mDA neurons of the substantia nigra pars compacta (SNpc) (also known as the A9 neurons), which give rise to the nigrostriatal pathway; and mDA neurons of the ventral tegmental area (VTA), which give rise to the mesolimbic and mesocortical pathways which innervate parts of the limbic system and the neocortex (also known as the A10 neurons). At day 60, TH-positive neurons could be observed, which were also positive for GIRK2, the G-protein-gated inwardly rectifying $K^+$ channel 2, an important functional protein with enriched expression in a A9 subtype mDA neuron (FIGS. 1E and F). However, almost all TH-positive neurons were negative for Calbindin, a calcium binding protein typically expressed in A10 subtype mDA neuron (FIGS. 2G and H). This data indicates that long-term cultured human midbrain-like organoids produced mDA neurons, which differentiated into A9 subtypes of neurons.

Figure 3:
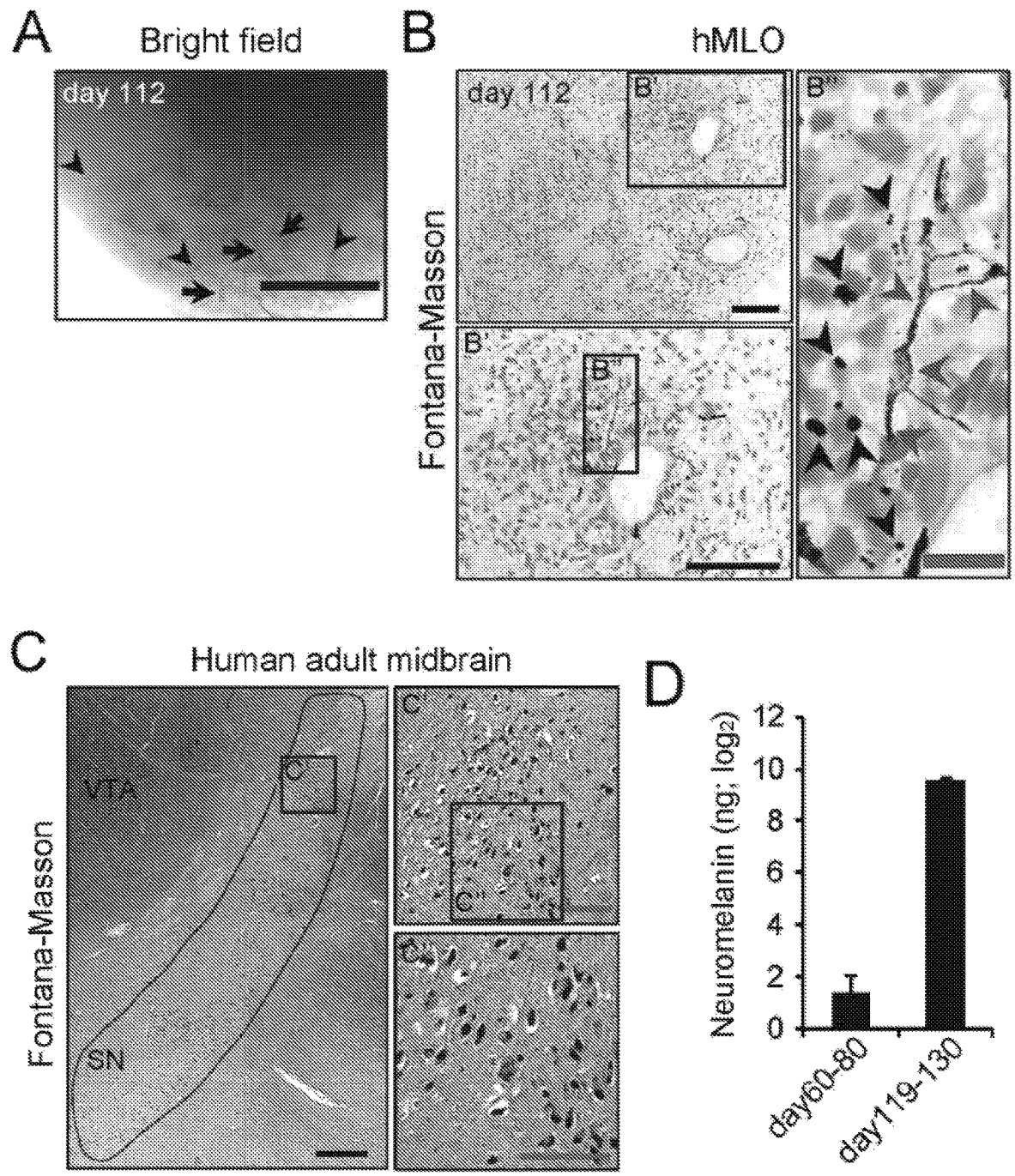
FIG. 3 shows the results of the identification of neuromelanin (NM) in human midbrain-like organoids (hMLOs). (A) provides a micrograph image showing the appearance of dark granules in human midbrain-like organoids at day 112. It is noted that dark pigments were localized within the neuronal compartment (arrows), as well as the extracellular compartment (arrowheads). Scale bar=200 µm. (B) shows micrograph images of a Fontana-Masson staining used to reveal neuromelanin-like granules within a human midbrain-like organoid. The presence of neuromelanin-like granules is shown in both intra- and extracellular compartments (blue and black arrowheads, respectively). Black scale bars=100 µm. Gray scale bar=20 µm. B' (bottom left) is an enlarged view of a region in B. B" (right) is an enlarged view of a region in B'. (C) shows micrographs of a Fontana-Masson staining of human post-mortem midbrain tissue, showing the presence of neuromelanin-like granules in human midbrain tissue. The area labelled as SN is the Substantia nigra. Black scale bars=1 mm. Gray scale bar=200 µm. C' (top right) is an enlarged view of a region in C, which was generated by tiling multiple images of a larger area. C" (bottom right) is an enlarged view of a region in C'. (D) shows a column graph quantifying the measurement of neuromelanin content in human midbrain-like organoids (n=3, for each time frame respectively). (E) shows scanning electron microscope (SEM) images of isolated neuromelanin (NM) granules in a day 122 human midbrain-like organoid. (F) shows scanning electron microscope (SEM) images of isolated neuromelanin (NM) granules in human post-mortem midbrain tissue. Scale bar=200 nm. (G) shows micrographs of bright field microscope images and Fontana-Masson stained sections showing that the formation of neuromelanin-like granules was accelerated by L-DOPA (50 µM) and dopamine (50 µM) treatments. Gray scale bar=2 mm. Black scale bar=100 µm. G', G", and G''' are high-magnification images of the black rectangle. (H) shows micrographs of bright field microscope images and Fontana-Masson stained sections showing that neuromelanin-like granules were not observed in murine midbrain-like organoids (MLOs; right column) compared to human midbrain-like organoids (left column). It is noted that both the human midbrain-like organoids (hMLOs) and murine midbrain-like organoids (mMLOs) contain TH-positive midbrain dopaminergic (mDA) neurons (bottom panels). Gray scale bar=2 mm. Black scale bar=500 µm. White scale bar=20 µm.
Figure 3:
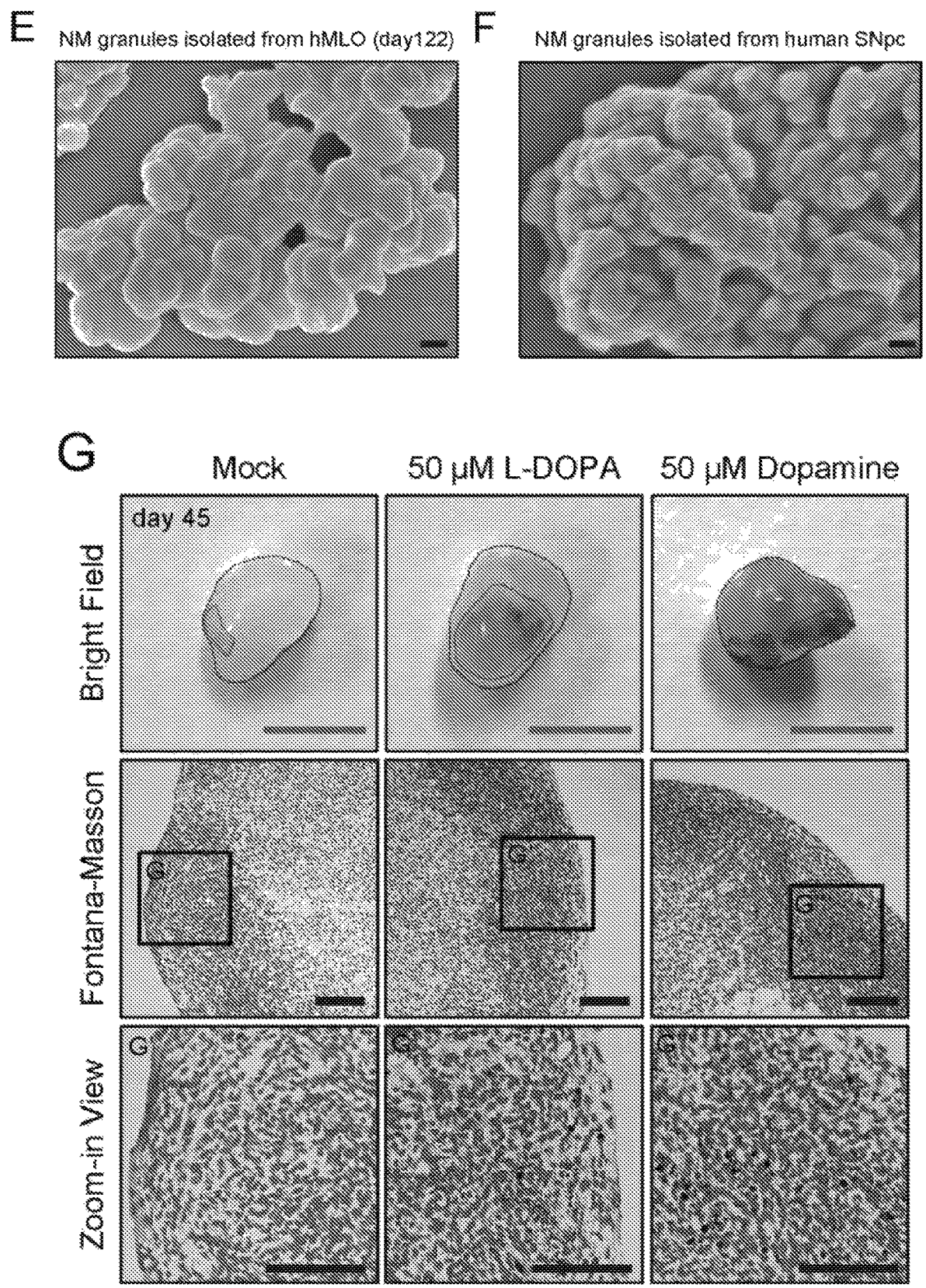
Figure 3:
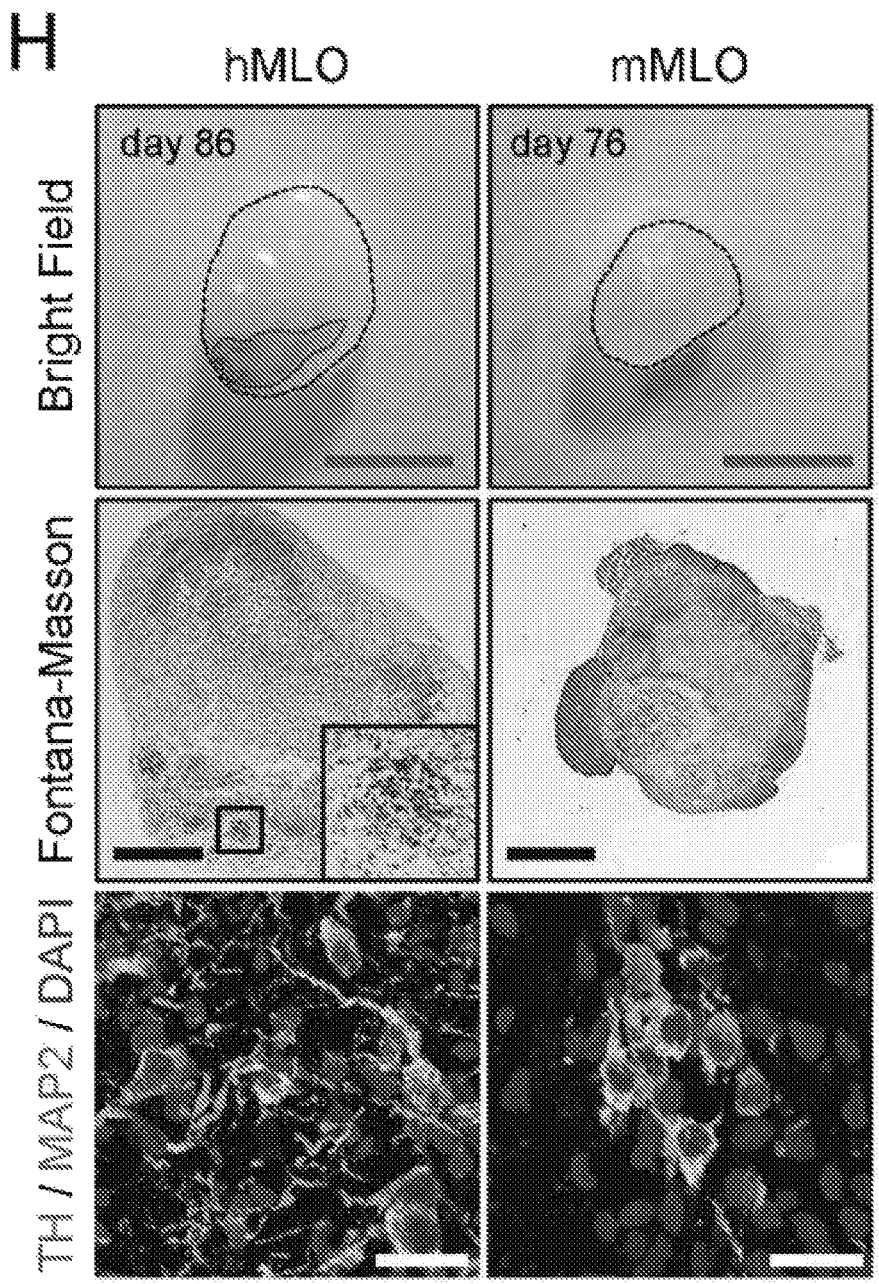

Functional Maturation of A9 Dopaminergic Neurons in Human Midbrain-Like Organoids Next, it was tested whether neurons in human midbrain-like organoids were electrically active and functionally mature. Instead of dissociating and culturing cells in monolayer from human midbrain-like organoids, human midbrain-like organoids were sliced into 350 μm sections and acute, targeted whole-cell patch recordings were performed (FIG. 3A). In voltage-clamp mode, neurons within human midbrain-like organoids showed both fast, inactivating inward and outward currents, which likely correspond to opening of voltage-dependent sodium ($Na^+$)- and potassium ($K^+$)-channels, respectively (FIG. 3B). The peak currents from voltage-gated $Na^+$- and $K^+$-channel were significantly increased from day 33 to 65 (FIG. 3C). Consistent with this, a considerable decrease in membrane resistance (Rm) and increase in membrane capacitance (Cm) was observed, which were correlated with functional maturation of neurons. Action potentials (APs) could be elicited by depolarizing the membrane in current clamp mode (FIG. 3D) and most of neurons within human midbrain-like organoid could elicit action potentials (69.23%, n=26) (FIG. 3E). Some of the neurons within human midbrain-like organoids showed rhythmic discharges, which was similar to rodent DA neurons (FIG. 6A) (Ferrari et al., 2012). Next, it was investigated whether neurons within human midbrain-like organoid exhibited spontaneous synaptic transmission in situ (FIG. 3F) and found that most of recorded neurons showed spontaneous excitatory postsynaptic currents (sEPSCs), as well as spontaneous inhibitory postsynaptic currents (FIG. 6B). In addition, in response to extracellular electrical stimulation, large-amplitude excitatory postsynaptic potentials (EPSPs>20 pA) were observed, demonstrating that neurons inside human midbrain-like organoids participate in network activity (FIG. 3G). Retrospective immunohistochemistry of recorded neurons (labelled with biocytin) in human midbrain-like organoids revealed that most of neurons (n=8 out of 10) were TH positive, indicating that recorded neurons were indeed mDA neurons (FIG. 3H). To further determine whether mDA neurons within human midbrain-like organoid produce extracellular dopamine, high-performance liquid chromatography (HPLC) measurements were performed and found gradual increase of dopamine content within human midbrain-like organoids as their maturation progressed (FIG. 3I). Taken together, this data indicates that mDA neurons within human midbrain-like organoid produce DA, exhibit mature neuronal properties, and are able to form synapses with neurons within human midbrain-like organoid.

Identification of Neuromelanin in Human Midbrain-Like Organoids, but not in Murine Midbrain-Like Organoids.

Figure 4:
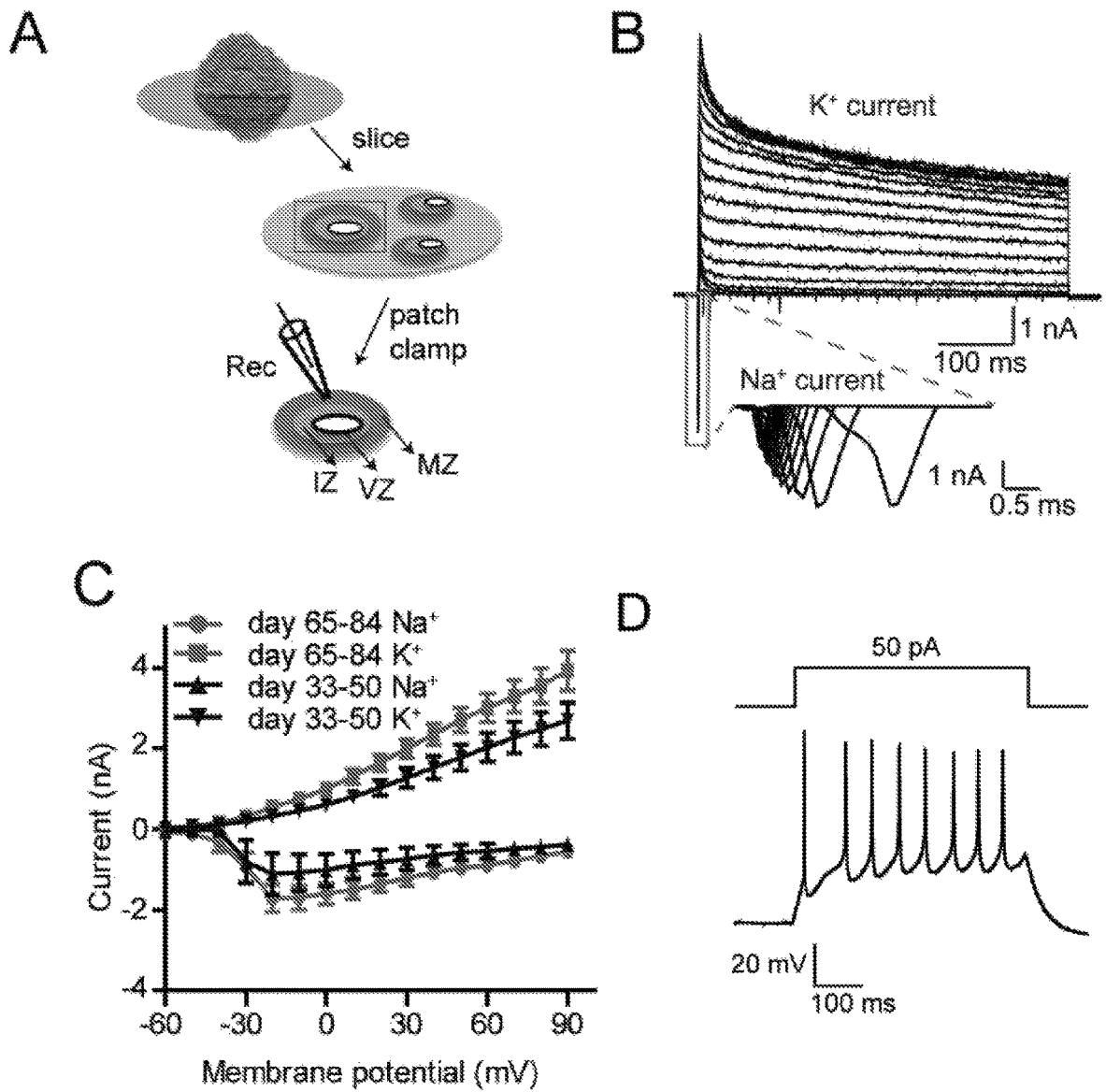
FIG. 4 shows the results of functional characterization of dopaminergic neurons from human midbrain-like organoids (hMLOs). (A) shows a schematic diagram illustrating the experimental set up used to investigate the electrophysiological activity of human midbrain-like organoids in situ [recordings (Rec.) and electric stimulation (Stim.)]. (B) shows representative trace recordings showing the presence of voltage-dependent $Na^+$ and $K^+$ currents in neurons inside human midbrain-like organoids. The gray box at the beginning of the electrophysiological recording highlights the presence of $Na^+$ channel-dependent inward currents. (C) shows a line graph showing the averaged current-voltage relationship (I/V) curves for the $Na^+$ and $K^+$ currents recorded (n=12 and 14 for days 33-50 and 65-84, respectively). (D) shows representative traces of multiple action potentials (APs; the lower panel) recorded from neurons inside day 35 human midbrain-like organoids, evoked by current injection (the upper panel). (E) shows a line graph depicting the number of action potentials (Aps) generated in response to a particular current pulse amplitude, of neurons inside human midbrain-like organoids (n=12 and 14 for days 33-50 and 65-84, respectively). (F) shows electrophysiological recordings showing spontaneous excitatory postsynaptic currents (sEPSCs) and spontaneous inhibitory postsynaptic currents (sIPSCs) (shown in the first recording (1)) recorded from a neuron inside a human midbrain-like organoidat day 80. These sEPSCs and sIPSCs were blocked by CNQX (an AMPA-type glutamate receptor antagonist) and AP5 (an NMDA-type glutamate receptor antagonist; results shown in the second recording (2)) and by picrotoxin (PTX, a GABAA blocker; results shown in the third recording (3)), respectively. (G) shows a schematic depicting electrical stimulation-evoked synaptic response recorded in the day 50 human midbrain-like organoid. The grey dot indicates onset of electrical stimulation. (H and I) show representative traces and frequency of spontaneous action potentials (Aps). (J) shows example traces of rebound depolarization.
Figure 4:
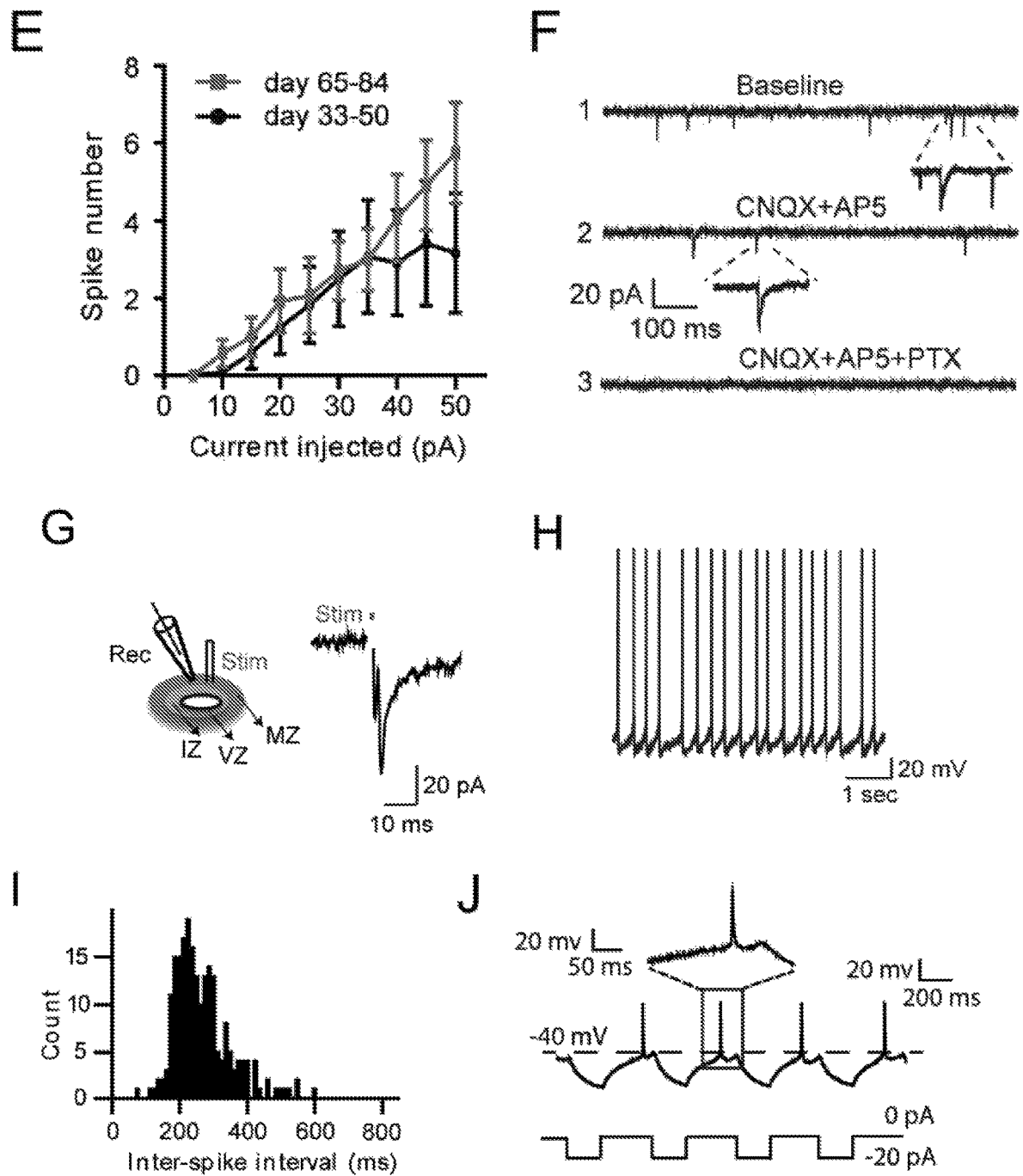
Figure 4:
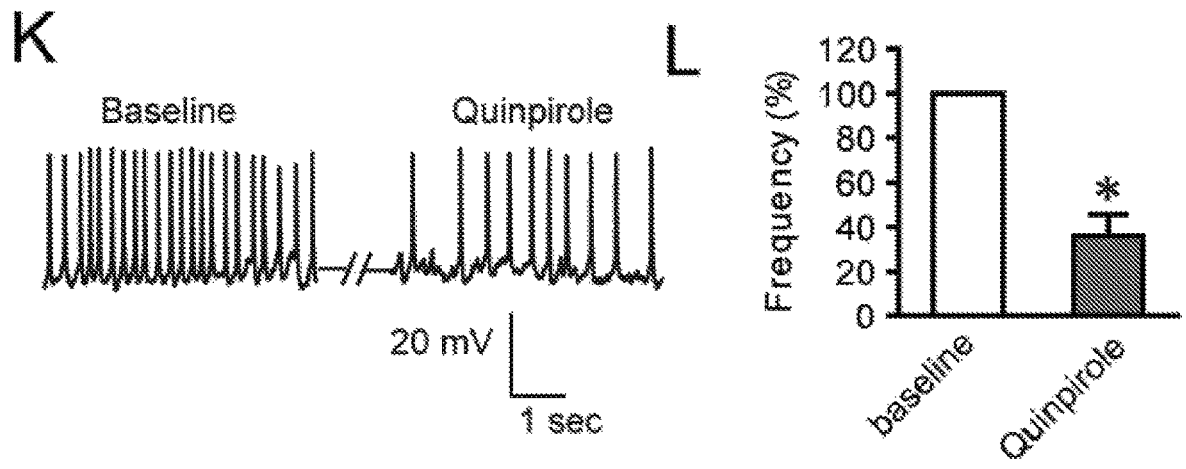
Figure 4:
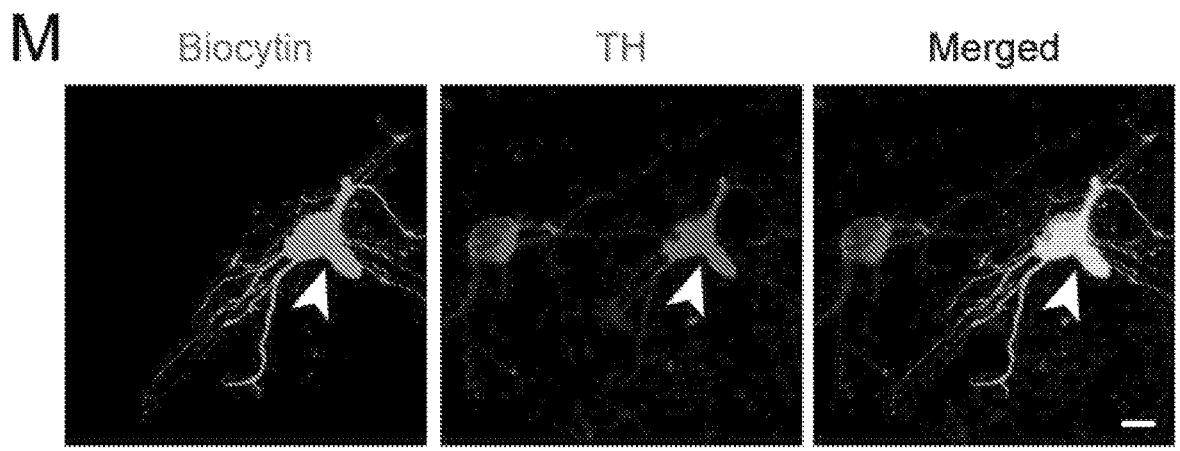
Figure 4:
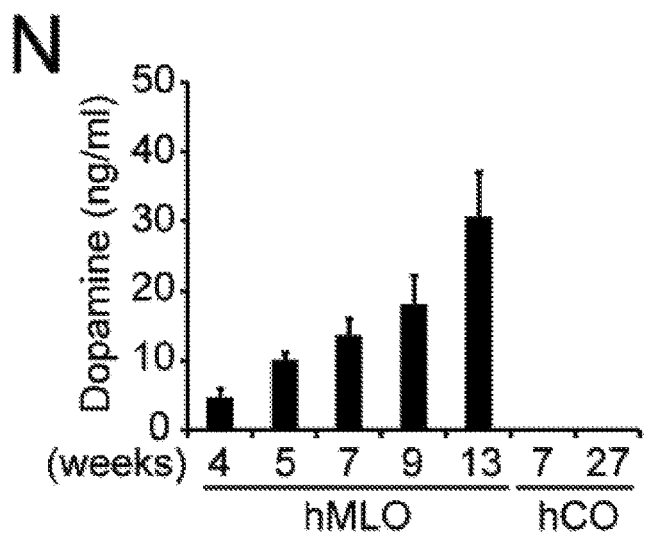

During long-term culture of human midbrain-like organoids, sparse, black-brown coloured deposits could be observed on the surface of human midbrain-like organoid from day 45 by light microscopy. The number of these deposits gradually increased with time (FIG. 4A). Without being bound by theory, it was hypothesized that these dark deposits were neuromelanins (NMs), which are insoluble, black-brown granular pigments that accumulate in the SN in humans and primates. To confirm this, human midbrain-like organoids were subject to paraffin-embedding and sectioned human midbrain-like organoid slices to Fontana-Masson staining for neuromelanin detection. It was found that these deposits were indeed positive for Fontana-Masson staining (FIG. 4B, FIGS. 7A and B). In FIG. 4B, large, rough, and darkly stained granules (presumably neuromelanins) were observed within neuronal cytosol and some of these granules (size of 2 to 3 μm) could be observed outside of neuronal cells, indicating that these neuromelanins could be secreted from hDA neurons within human midbrain-like organoids (FIG. 4B). In contrast, Fontana-Masson staining failed to detect positive granules from 2D-cultured human induced DA neurons at comparable days in vitro (data not shown). Given that neuromelanin is synthesized as a by-product of DA synthesis in mDA neurons, the addition of exogenous dopamine precursor (L-DOPA) is understood to accelerate the accumulation of neuromelanins in younger human midbrain-like organoid. Indeed, the robust distribution of neuromelanin-like granules was observed in human midbrain-like organoid treated with L-DOPA (50 μM) from human midbrain-like organoid at day 35, while no neuromelanin-like granules were observed in untreated human midbrain-like organoid at the same day (FIG. 4C). To check whether neuromelanins contained cells that were TH-positive cells, immunostaining was performed using adjacent sections from the same human midbrain-like organoid. Consequently, TH-positive cells from the area shown to also be positive for Fontana-Masson staining were observed in the same human midbrain-like organoid (FIG. 4D). Neuromelanin-like granules have been observed mostly in primates, but not in mice No neuromelanin-like granules were observed in mouse embryonic stem cell-derived midbrain-like organoids that contained high percentages of TH-positive neurons with comparable days in vitro (FIG. 4D). Furthermore, no Fontana-Masson staining positive granules could be detected from human cerebral organoids from the same human embryonic stem cell line (line H1) (FIG. 7B), indicating that only mDA neurons grown in three-dimensional culture could produce neuromelanin-like granules in situ. In summary, it was demonstrated that human embryonic stem cell aggregates can be steered to differentiate into midbrain progenitors that eventually self-organized into a 3D human midbrain-like organoid that contains three distinct layers with functional mDA neurons. It was found that only human mDA neurons within a 3D midbrain-like organoid could produce neuromelanin-like granules, but human mDA neurons in 2D culture or mouse mDA neurons within 3D midbrain-like organoid could not (FIG. 4D).

Recently, the association of NM with the vulnerability of DA neurons in PD by microglia-induced neuroinflammation has been studied by using a synthetic dopamine melanin in place of the native ones.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Culture of hESCs

The human embryonic stem cell lines (hESC) lines H1 (WA01, passage 30) and H9 (WA09, passage 25) were used. The human embryonic stem cells were maintained under feeder-free conditions over matrigel-coated 6-well plates (BD Biosciences) in mTeSR media (Stemcell Technologies) at 37° C. in a 5% humidified $CO_2$ incubator. The media was changed daily and the human embryonic stem cell cultures were split every 5 days using 1 mg/ml Dispase (Stemcell Technologies). All human embryonic stem cell lines were confirmed negative for mycoplasma contamination and exhibited normal karyotypes. Commercially available human embryonic stem cell (ESC) lines (H1 and H9; WiCell Research Institute) were used in referenced experiments.

These cell lines were established from inner cell mass of human embryos. It is understood that all information pertaining to these cell lines is publicly available (see for example, James et al., 1998, and the information available online at https://www.wicell.org/home/stem-cell-lines/catalog-of-stem-cell-lines/wa01.cmsx and https://www.wicell.org/home/stem-cell-lines/catalog-of-stem-cell-lines/wa09.cmsx).

Generation of Human Midbrain-Like Organoids

For generation of human midbrain-like organoids, human embryonic stem cell lines were used at less than 40 passages. The human embryonic stem cells were dissociated from intact colonies to single cells with TrypLE Express (Life Technologies), and 10,000 cells were plated in each well of low-cell-adhesion 96-well culture plate with V-bottomed conical wells (Sumitomo Bakelite) to form uniform EBs in neuronal induction medium containing DMEM/F12:Neurobasal (1:1), 1:100 N2 supplement (Invitrogen), 1:50 B27 without vitamin A (Invitrogen), 1% GlutaMAX (Invitrogen), 1% minimum essential media-nonessential amino acid (Invitrogen), and 0.1% β-mercaptoethanol (Invitrogen) supplemented with 1 µg/ml Heparin (Sigma-Aldrich), 10 µM SB431542 (Stemgent), 200 ng/ml Noggin (Prospec), 0.8 µM CHIR99021 (Reagents Direct), and 10 µM ROCK inhibitor Y27632 (Calbiochem). ROCK inhibitor was added for the first 48 hours and neuronal induction medium was changed on day 2. On day 4, human midbrain-like organoids were cultured with addition of 100 ng/ml SHH-C25II (R&D Systems) and 100 ng/ml FGF8 (R&D Systems) for midbrain patterning. After 3 days, the human midbrain-like organoids started to extrude neuroectodermal buds, media were completely removed and immediately 30 µl of growth factor reduced matrigel was added in each well by pipetting using pre-chilled 200 µl pipette tip. The matrigel embedded midbrain-like organoid was placed into 37° C. incubator for 30 minutes to allow the matrigel to solidify, and was grown in tissue growth induction medium containing Neurobasal, 1:100 N2 supplement (Invitrogen), 1:50 B27 without vitamin A (Invitrogen), 1% GlutaMAX (Invitrogen), 1% minimum essential media-nonessential amino acid (Invitrogen), and 0.1% β-mercaptoethanol (Invitrogen) supplemented with 2.5 µg/ml Insulin (Sigma-Aldrich), 200 ng/ml Laminin (Sigma-Aldrich), 100 ng/ml SHH-C25II (R&D Systems), and 100 ng/ml FGF8 (R&D Systems) for 24 h. Once hMLOs were embedded in matrigel, organoids begin forming more expanded neuroepithelium. To promote growth and differentiation, the hMLOs were transferred onto ultra-low attachment 6 well-plate (Costar) by pipetting using a cut 1000 µl pipette tip in final differentiation media containing Neurobasal, 1:100 N2 supplement (Invitrogen), 1:50 B27 without vitamin A (Invitrogen), 1% GlutaMAX (Invitrogen), 1% minimum essential media-nonessential amino acid (Invitrogen), 0.1% β-mercaptoethanol (Invitrogen), 10 ng/ml BDNF (Peprotech), 10 ng/ml GDNF (Peprotech), 100 µM Ascorbic acid (Sigma-Aldrich), and 125 µM db-cAMP (Sigma-Aldrich). Human midbrain-like organoids were cultured using an orbital shaker to enhance exchanges of nutrients and oxygen. Antibiotics (100 U/ml penicillin G, 100 µg/ml streptomycin) were included in culture media to prevent potential bacterial contamination for long-term culture. The medium was replaced every 3 days.

Immunohistochemistry

Human midbrain-like organoids were fixed in 4% paraformaldehyde (PFA) overnight, washed in phosphate-buffered saline (PBS), incubated in 30% sucrose solution in PBS at 4° C. overnight, and subsequently embedded in O.C.T compound (Sakura Finetek) for cryosection. Frozen human midbrain-like organoids were cryo-sectioned at 16 µm thickness. For immunohistochemistry, cryo-sectioned human midbrain-like organoids were blocked with blocking buffer (PBS with 3% bovine serum albumin (BSA) and 0.5% Triton X-100) for 1 hour at room temperature. Sections were then stained with primary antibodies diluted in a buffer (PBS with 1% BSA and 0.1% Triton X-100) and stained with secondary antibodies in PBS for 1 hour at room temperature. All sections were counterstained with DAPI (1/5000, Sigma-Aldrich) and mounted with Aqua-mount (Thermo) or kept in PBS, protected from light. Images were taken on an LSM710 confocal microscope or an Observer Z.1 inverted microscope (Zeiss). The primary and secondary antibodies were described in Table 4.

RNA Extraction, Reverse Transcription, Real-Time RT-PCR, and RNA-Seq Preparation Total RNAs were isolated from either hMLOs, 2D-DA neurons, or undifferentiated hESCs using TRIzol Reagent (Invitrogen). DNA contaminants were digested with DNASE I (Ambion) and 500 ng of RNA was reverse-transcribed using the SuperScript II kit (Invitrogen) to produce the cDNA. Quantitative RT-PCR was performed using ViiA 7 Real-Time PCR system (Applied Biosystem). ΔΔCt method was applied to normalize expression levels of each gene to that of GAPDH. Primers used were priorly tested to ensure specific melting curves and additionally validated by using human cDNA library, prepared from human neuronal samples (ScienCell). For RNA-seq library preparation of hMLOs and 2D-DA neurons, the total RNA was further purified by column (Puelink RNA Mini kit, Ambion), and was prepared using 4 g of total RNA according to manufacturer's protocol (TruSeq RNA Sample Preparation Kit v2, Illumina). Samples were multiplexed and sequenced single read 150 bp paired end (HiSeq 2000, Illumina).

Human Brain Dissection

The ventral half of the midbrain was dissected from second trimester prenatal brainstem under visual inspection, using a scalpel and hand-held dental drill (Table 3). Cases were donated with informed consent of the mother, and were selected on the basis of the absence of any congenital anatomical abnormality on macroscopic brain inspection, and the absence of any major genetic defect noted on prenatal testing. The IRB approval is from the Western IRB, a private and fully accredited IRB that is used by many independent institutions in the USA: address 1019 39$^{th}$ Avenue SE Suite 120, Puyallup, WA 98374-2115. Study number: 1126332. WIRB protocol number: 20111080. Approval expires: Jul. 18, 2016.

Post-Mortem Brain: RNA Extraction and Sequencing

Details of post-mortem RNA Extraction and Sequencing, and RNA-seq data processing were previously described (Jaffe et al., 2015). Post-mortem tissue homogenates of Ventral Midbrain were obtained from prenatal brains. Following RNA extraction, RNA quality was measured using high-resolution capillary electrophoresis on an Agilent Technologies Bioanalyzer 2100, and RNA integrity numbers (RINs) were acquired for all the 10 samples.

Ribosomal RNA Depletion (RiboZero) with Strand-Specific Library Preparation and Q/C RNA-seq libraries were constructed using Illumina TruSeq Stranded Total RNA Ribo-Zero sample Prep Kit following the manufacturer's protocol. The ribosome RNAs were removed using Ribo-zero beads from ~800 ng DNAse treated total RNA. Following purification, the total RNA without Ribosome RNA was fragmented into small pieces using divalent cations under elevated temperature (94 degree) for 2 minutes. Under this condition, the range of the fragments length is from 130-290 bp with a median length of 185 bp. Reverse transcriptase and random primers were used to copy the cleaved RNA fragments into first strand cDNA. The second strand cDNA was synthesized using DNA Polymerase I and RNaseH, dUTP in place of dTTP. These cDNA fragments then went through an end repair process using T4 DNA polymerase, T4 PNK and Klenow DNA polymerase, and the addition of a single 'A' base using Klenow exo (3' to 5' exo minus), then ligation of the Illumina PE adapters using T4 DNA Ligase. An index (96 unique dual-index pairs) was inserted into Illumina adapters so that multiple samples can be sequenced in one lane of 8-lane flow cell if necessary. These products were then purified and enriched with 15 cycles of PCR to create the final cDNA library for high through put DNA sequencing using the H 100 base-pair paired-end reads and the Illumina HiSeq 3000, targeting approximately 100M reads per sample. The concentration of RNA libraries was measured by Qubit (Invitrogen, CA). The quality of RNA-seq library was measured by LabChipGX (Caliper, MA) using HT DNA 1K/12K/HiSens Labchip.

Bioinformatics Analysis

RNA-Seq data were mapped against the human genome version hg19 with TopHat2-2.0.12 (Kim et al., 2013) using the GENCODE Release 19 version of gene annotations. R-3.1.2 (Team, 2014) and Bioconductor 3.0 (Gentleman et al., 2004) were used for the RNA-Seq analysis. Reads were counted using the R package GenomicAlignments (Lawrence et al., 2013) (mode='Union', inter.feature=FALSE), only primary read alignments were retained. R log transformed values of the counts and differential expression was calculated using DESeq2 (Love et al., 2014). We used an adjusted p-value threshold of 0.0005, and a log fold change threshold of 2 (−2) for up- and downregulated genes respectively. Coverage plots (FIGS. 2E and F) and PCA (FIG. 6F) were created using ggplot2_1.0.0 (Wickham, 2009). Adult brain RNA-Seq data from the GTEx project (Consortium, 2015) were used as a comparison. In order to plot gene expression in heatmaps, genes were sorted by fold change, and the distribution of expression estimates for each gene were standardized for visualization by subtracting the mean and dividing by standard deviation.

Flow Cytometry

For intracellular staining, cells were fixed and permeabilized with transcription factor staining buffer set (eBioscience). Briefly, cells were firstly dissociated with TrypLE™ Express (Gibco), spun down and cell pellets were resuspended in 1 ml 1× fixation/permeabilization buffer in the dark at 4° C. for 30 min. Without washing to minimize loss of cell, 2 ml of 1× permeabilization buffer was added to cell suspension and samples were spun down. The supernatant was decanted and samples were stained with antibodies in 10011 permeabilization buffer at room temperature for 1 h. Finally, 300 µl of staining buffer was added to cell suspension until analysis. Cells were filtered through BD Falcon 12×75 mm tube with cell strainer (BD Biosciences). Flow cytometry analysis was performed using a BD LSRFortressa™ X-20 (BD Biosciences), and all data were represented by FlowJo software. Negative threshold gates were defined with two negative control samples (dissociated hMLO cells stained with secondary antibody alone and hESC stained with both primary and secondary antibodies).

Dopaminergic Neuron Induction (2D Method)

DA neuron differentiation was performed follow floor-plate based neural induction protocol (Kriks et al., 2011). The hESCs were plated at $35 \times 10^3$ cells per $cm^2$ and grown on matrigel in Basal medium 1 containing DMEM, 15% KSR, 2 mM L-Glutamine and 10 µM 3-mercaptoethanol, with addition of 100 nM LDN193189 (Stemgent) and 10 µM SB431542 for 24 h. On day 1, medium was changed to Basal Medium 1 with addition of 100 nM LDN193189, 10 µM SB431542, 100 ng/ml SHH-C25II, 2 µM Purmorphamine (Stemgent) and 100 ng/ml FGF8 for 2 days. On day 3, medium was changed with addition of 3 µM CHIR99021. By day 5, medium was gradually shifted to N2 medium containing DMEM, N2 supplement, 2 mM L-Glutamine and 10 µM 3-mercaptoethanol (Basal Medium 2) for 2 days interval as described previously (Chambers et al., 2009). On day 11 onwards, Basal medium 3 containing Neurobasal/B27/L-Glutamine (Invitrogen) was changed supplemented with 3 µM CHIR99021 for 2 days. After which, Basal medium 3 supplemented with 10 µM DAPT (Sigma-Aldrich), 0.2 mM Ascorbic acid, 20 ng/ml BDNF, 20 ng/ml GDNF, 0.2 mM db-cAMP and 1 ng/ml TGF-33 (Invitrogen) was used until day 20, media were changed every other day. On day 20, cells were dissociated using 0.05% Trypsin-EDTA and replated under high cell density ($300$-$400 \times 10^3$ cells per $cm^2$) on dishes pre-coated with 0.1 mg/ml poly-lysine and 1 µg/ml Laminin. Cells were grown in Neurobasal/B27 medium containing 10 µM DAPT, 0.2 mM Ascorbic acid, 20 ng/ml BDNF, 20 ng/ml GDNF, 0.2 mM db-cAMP and 1 ng/ml TGF-β3, and changed fresh medium every other day until experimental analysis as indicated.

Generation of Cerebral Organoid

Cerebral organoids were generated using the same protocol as Lancaster et al (Lancaster and Knoblich, 2014; Lancaster et al., 2013). Briefly, hESCs were dissociated with TrypLE™ Express, and 10,000 cells were plated in each well of low-cells-adhesion 96-well culture plate with V-bottomed conical wells to form EBs in DMEM/F12, and 20% Knockout serum replacement (Gibco), 1% GlutaMax (Invitrogen), 1% NEAA (Invitrogen), 0.1% β-mercaptoethanol (Invitrogen), 4 ng/ml of bFGF (Invitrogen), and 20 µM ROCK inhibitor Y27632 (Calbiochem). At day 6, EBs were transferred to low adhesion 24-well plate in neural induction media containing DMEM/F12, 1:100 N2 supplement (Invitrogen), 1% GlutaMax (Invitrogen), 1% NEAA (Invitrogen), and 1 µg/ml Heparin (Sigma-Aldrich). The EBs began to form neuroepithelium, and transfer to embed in Matrigel (BD Bioscience) at day 11 on a sheet of Parafilm with small dimples. The Matrigel droplets were solidified at 37° C. and grown in differentiation media containing DMEM/F12:Neurobasal (1:1), 1:100 N2 supplement (Invitrogen), 1:50 B27 without vitamin A (Invitrogen), 1% GlutaMAX (Invitrogen), 1% NEAA (Invitrogen), 0.1% β-mercaptoethanol (Invitrogen), 2.5 µg/ml Insulin (Sigma-Aldrich), and 100 U/ml penicillin G, 100 µg/ml streptomycin (Gibco-BRL) to allow stationary growth. At day 15, the droplets were transferred onto ultra-low attachment 6-well plate (Costar) in final media containing B27 supplement with vitamin A (Invitrogen) in differentiation media. The cerebral organoids were cultured on orbital shaker. The media was replaced every 3 days.

Neuromelanin Staining (Fontana-Masson Staining)

Human midbrain-like organoids were fixed in 4% paraformaldehyde (PFA) overnight, washed in PBS, embedded in paraffin block, and subsequently sectioned at 4 µm thickness. Next, hMLOsections were deparaffinized, hydrated with distilled water, and stained by Fontana-Masson staining kit (Abcam) according to manufacturer's protocol (Carriel et al., 2011). Briefly, the sections were placed in ammoniacal silver solution and incubated in a 58 to 60° C. water bath for 30 to 60 minutes until the tissue sections had become yellowish/brown in colour. The tissue sections were washed with distilled water and incubated in gold chloride solution (0.2%) for 30 seconds. Next, the sections were incubated in gold chloride solution (0.2%) for 30 seconds and subsequently incubated with sodium thiosulfate solution (5%) for 2 minutes. Finally, the sections were incubated in nuclear fast red solution for 5 minutes for staining and mounting. Images were taken on an LSM710 confocal microscope or an Observer Z. 1 inverted microscope (Zeiss).

Neuromelanin Isolation and Quantification

The hMLOs that were positive for NM granules were homogenized in a glass tube with 1.5 ml of pH 7.4 phosphate buffer (50 mM), followed by the centrifugation at 12,000 g for 30 min. The resulting pellet was washed with pH 7.4 phosphate buffer twice, and then was resuspended with 1.5 ml of Tris buffer (50 mM, pH 7.4), containing sodium dodecyl sulfate (5 mg/ml) and 0.2 mg/ml proteinase K (Fermentas) using a shaker, for 3 h at 37° C. Resuspended NM granules were subsequently centrifuged at 12,000 g for 30 min, and then washed twice with NaCl (9 mg/ml), and twice with distilled water. For the quantification of NM granules, NM granules were solubilized in 1 ml of 1 M NaOH at 80° C. for 1 h to measure NM by spectrophotometer (350 nm). The solution is centrifuged and the supernatant was collected. For the imaging of NM structure by AFM and SEM, the pellet was washed with 1.5 ml of methanol and 1 ml of hexane. Lastly, it was dried by lyophilization (Bush et al., 2006; Zecca et al., 2002).

Atomic Force Microscopy (AFM)

In this measurement, commercial AFM system (NX-Bio, Park Systems Corp., Korea) was used. The Z scanner mounted on the AFM head makes it possible for the probe to maintain constant feedback conditions (force or distance) as it is moved over a sample surface. It is also combined with commercial inverted optical microscopy (Ti eclipse, Nikon, Japan) which enables easily detect the sample and AFM probe position. All images were performed using AFM contact mode in air condition at room temperature. The scanning area was 2×2 μm$^2$, the resolution was 256×256 pixels. The height and deflection images were collected simultaneously with 0.8-1.2 Hz of scan rate. To obtain a reliable image, we used very soft commercial Si cantilevers (CSG-01, NT-MDT, Russia) which was cleaned with an UV/ozone cleaner for 15 min. Spring constants (0.06 N/m) and resonant frequency (12 kHz) of the probes were evaluated by measurement of thermal fluctuations of the probes. For AFM imaging, NM samples were prepared by pipette dropping of NM solution (5 μl) onto cleaned and cleaved mica surface. The NM samples on mica surface were stored and dried in the dark condition until NM is fully dry.

Scanning Electron Microscopy (SEM)

The procedures used for AFM sample preparation as discussed above were implemented for the NM samples prior to SEM analysis. The pre-dried samples were then sputter-coated with a 10 nm thick layer of gold for 50 seconds at 20 mA using Auto Fine Coater (JEOL JFC-1600, Japan), and SEM images were processed with Field Emission Scanning Electron Microscopy (JEOL 6340F, Japan) equipped with a cold cathode emitter set at an acceleration voltage of 5.0 kV.

Single-Cell Gene Expression Analysis

The 120 to 150 days hMLOs were dissociated to single cells by TrypLE™ Express and the cells were filtered through BD Falcon 12×75 mm tube with cell strainer. To collect NM contained cells, cells were sorted directly with the BD FACSAria II (BD Bioscience) into 96-well PCR plates loaded with 5 μl of the reverse transcription-specific target amplification solution (Life Technologies) based on detection using excitation laser 355 nm and filter 530/30 (Nighswander-Rempel et al., 2005). For positive control, 2D differentiated DA neurons were suspended and put directly with same FACS instrument in 96-well PCR plates. The reverse transcription (RT)-specific target amplification was carried out in thermal cycler with 20-cycle preamplification and unused primers were digested away by exonuclease 1 (New England BioLabs) treatment, and then samples were diluted 3-fold prior to the analysis. The preamplified products in 96-well PCR plates were validated expression of GAPDH, MAP2, and TH by qRT-PCR, and we removed cells to be shown weak or no expression of those genes. For characterization of mDA neuron in hMLO, we analyzed cells except those cells. These samples were analyzed with 2× SsoFast EvaGreen Supermix with Low ROX (Bio-Rad) and individual qPCR primers in 96×96 Dynamic Arrays on a Biomark System (Fluidigm), following manufacture's instruction. Ct values were calculated using the BioMark Real-Time PCR Analysis software (Fluidigm). Results were represented as a heatmap by color-coded Ct values in FIGS. 7N and O. Each primer pair was designed and validated to ensure specific melting curves and additionally evaluated by using commercial reference sample [human cDNA library prepared from human neurons (ScienCell)]

Electrophysiology

Whole cell patch clamp recording techniques were used to measure the intrinsic properties of neurons within human midbrain-like organoids. Each human midbrain-like organoid was placed in a chamber and submerged beneath continuously perfused artificial CSF (aCSF) saturated with 95% $O_2$ and 5% $CO_2$ at 30 to 32° C. Patch pipettes (2 to 4 MΩ) were filled with an intracellular solution containing (in mM): Potassium methanesulfonate 135, KCl 10, HEPES 10, EGTA 1 Na$_2$ATP 2; 290 mOsm; pH was adjusted to between 7.2 to 7.4 with KOH. Whole cell recordings were performed using IR-DIC visualization techniques with an Olympus BX51WI upright microscope, using a ×60 water immersion lens. Signals were recorded using an MultiClamp 700B amplifier, filtered at 3 kHz using a Bessel filter, and digitized at 10 kHz with a Digidata 1322A analog-to-digital (A/D) board (Molecular Devices, Sunnyvale, CA). To measure Na$^+$ currents and K$^+$ currents, voltage steps (500 msec duration) were applied from a holding potential of −70 mV to a range of test potentials between −50 and +90 mV (10 mV increments). For excitability test, a series of current pulses (500 msec) of increasing amplitude (5 pA steps) were injected to make the current-firing frequency relationship. Spontaneous excitatory postsynaptic currents (sEPSCs) were collected at a holding potential of −70 mV. Evoked excitatory postsynaptic currents (eEPSCs) was induced by tungsten wire electrodes placed about 300 μm away from the recording neuron within the hMLO.

High-Performance Liquid Chromatography (HPLC)

Single human midbrain-like organoids or human cortical spheroids (hCOs) were homogenized in 100 μl of 0.5 N perchloric acid, centrifuged, and filtrated through 0.1 mm filters (Millipore). Only resulting supernatants were loaded into a HPLC system (Thermo Scientific). The mobile phase for dopamine is run with 12.5% acetonitrile buffer (pH 3.0, 90 mM sodium phosphate monobasic dehydrate, 50 mM citric acid, 2.1 mM 1-octanesulfonate monohydrate, and 0.1 mM EDTA). Dionex Coulochem III Electrochemical detector was used to determine dopamine levels via a customized program with a sensitivity range of 2-10 nA. The results were then analysed through the normalization of cell counts and conversion of peak reads to numerical expression.

Statistical Analysis

All experiments were conducted at least in triplicate, and the results are expressed as the mean±standard error. Statistical analyses were performed using the one-way ANOVA test and followed by Student's t-test if necessary. A $p<0.05$ was considered statistically significant.

Tables

TABLE 1

Quantitative analysis of NM granules. The data were collected by using custom-made atomic force microscopy and the analyses were performed using a custom-made imaging process program.

| | Height (nm) | Diameter (nm) | Volume (μm³) | Height (nm) | Diameter (nm) | Volume (μm³) |
|---|---|---|---|---|---|---|
| | hMLO day122 NM (FIG. 7D, E, and F, Left) | | | hMLO day122 NM (FIG. 7D, E, and F, Right) | | |
| Average | 16.96 | 125.06 | 6.86E−05 | 22.47 | 156.79 | 2.73E−04 |
| STDV | 4.57 | 62.99 | 7.54E−05 | 5.79 | 111.61 | 4.49E−04 |
| | Human postmortem substantia nigra pars compacta NM | | | Human postmortem substantia nigra pars compacta NM | | |
| Average | 15.56 | 119.5 | 7.65E−05 | 14.41 | 151.81 | 9.78E−05 |
| STDV | 4.1 | 74.5 | 5.04E−05 | 3.52 | 110.16 | 3.67E−05 |

TABLE 3

Information for each human prenatal midbrain samples that was used to perform RNA-seq analysis.

| Name of sample | Gestational Age (WW/D) | Sex | Race |
|---|---|---|---|
| Prenatal Midbrain_1 | 17/4 | Male | Caucasian |
| Prenatal Midbrain_2 | 17/5 | Male | Caucasian |
| Prenatal Midbrain_3 | 17/3 | Male | Caucasian |
| Prenatal Midbrain_4 | 17/0 | Male | Caucasian |
| Prenatal Midbrain_5 | 17/0 | Male | Caucasian |
| Prenatal Midbrain_6 | 16/0 | Female | Caucasian |
| Prenatal Midbrain_7 | 15/0 | Female | Caucasian |
| Prenatal Midbrain_8 | 13/2 | — | Caucasian |
| Prenatal Midbrain_9 | 13/2 | Female | Caucasian |
| Prenatal Midbrain_10 | 13/0 | — | Caucasian |

TABLE 4

List of antibodies and their dilutions for immunostaining and flow cytometry

| Antibody | Host species | Company | Cat. No | Dilution |
|---|---|---|---|---|
| Ki67 | Mouse | BD Biosciences | 550609 | 1:200 |
| MAP2 | Chicken | ABcam | ab5392 | 1:5000 |
| OTX2 | Goat | Neuromics | GT15095 | 1:1000 |
| OTX2 | Rabbit | ABcam | Ab1990 | 1:1000 |
| MASH1 | Mouse | BD Biosciences | 556604 | 1:200 |
| aPKC | Mouse | Santa Cruz | Sc-17781 | 1:100 |
| FOXA2 | Rabbit | ABcam | ab108422 | 1:250 |
| LMX1A | Goat | Santa Cruz | Sc-54273 | 1:100 |
| NURR1 | Rabbit | Santa Cruz | sc-991 | 1:200 |
| TH | Rabbit | PelFreez | P40101-0 | 1:1000 |

TABLE 2

Summary of major electrophysiological parameters of each induced neuron analysed in this study.

| Neurons number | Cm (pF) | RM (MOhm) | Ra (MOhm) | RMP (mV) | AP-threshold (mV) | Spike AHP (mV) | Half AP width (ms) |
|---|---|---|---|---|---|---|---|
| #1 | 16 | 1000 | 6 | −48 | −35 | 12.37 | 1.14 |
| #2 | 18 | 1000 | 8 | −58 | −30 | 9.33 | 2.32 |
| #3 | 9 | 2500 | 12 | −45 | — | — | — |
| #4 | 12 | 2000 | 11 | −50 | — | — | — |
| #5 | 24 | 1400 | 16 | −38 | −27 | 18.31 | 1.68 |
| #6 | 13 | 2000 | 12 | −42 | — | — | — |
| #7 | 34 | 1400 | 13 | −46 | — | — | — |
| #8 | 37 | 1000 | 9 | −42 | — | — | — |
| #9 | 10 | 1600 | 10 | −48 | −48 | 4.54 | 2.1 |
| #10 | 25 | 1200 | 12 | −52 | −37 | 5.91 | 1.84 |
| #11 | 29 | 1200 | 9 | −55 | — | — | — |
| #12 | 19 | 2100 | 13 | −48 | −35 | 17.4 | 1.62 |
| #13 | 13 | 2000 | 11 | −39 | −28 | 7.46 | 2.52 |
| #14 | 13 | 1200 | 12 | −43 | −24 | 5.17 | 2.75 |
| #15 | 29 | 1000 | 12 | −60 | −34 | 10.18 | 1.34 |
| #16 | 19 | 1800 | 10 | −55 | −35 | 6.05 | 3.15 |
| #17 | 13 | 1000 | 10 | −45 | −29 | 8.75 | 1.82 |
| #18 | 13 | 1200 | 13 | −48 | −28 | 11.6 | 2.33 |
| #19 | 18 | 1000 | 8 | −58 | −33 | 9.98 | 1.42 |
| #20 | 30 | 1200 | 12 | −53 | −40 | 5.95 | 1.14 |
| #21 | 22 | 1600 | 6 | −67 | −40 | 12.43 | 1.01 |
| #22 | 44 | 800 | 13 | −60 | −44 | 12.86 | 1 |
| #23 | 35 | 900 | 11 | −53 | −36 | 9.03 | 1.84 |
| #24 | 28 | 1000 | 14 | −48 | — | — | — |
| #25 | 17 | 700 | 7 | −57 | — | — | — |
| #26 | 36 | 1100 | 10 | −40 | −28 | 11.33 | 2.53 |
| Average (at day 33-50) | 20.50 ± 2.70 | 1533 ± 145.8 | 10.92 ± 0.77 | −47.67 ± 1.64 | −35.33 ± 2.95 | 11.31 ± 2.353 | 1.78 ± 0.17 |
| Average (at day 65-84) | 23.57 ± 2.71 | 1179 ± 100.1 | 10.64 ± 0.63 | −51.86 ± 2.22 | −33.25 ± 1.75 | 9.23 ± 0.76 | 1.90 ± 0.21 |

TABLE 4-continued

List of antibodies and their dilutions for immunostaining and flow cytometry

| Antibody | Host species | Company | Cat. No | Dilution |
|---|---|---|---|---|
| TH | Mouse | ImmunoStar | 22941 | 1:1000 |
| DAT | Rat | Millipore | MAB369 | 1:2000 |
| GIRK2 | Rabbit | Alomone | APC-006 | 1:500 |
| CALBINDIN | Rabbit | Swant | D-28k | 1:20000 |
| FOXG1 | Rabbit | ABcam | ab18259 | 1:2000 |
| GBX2 | Goat | Santa Cruz | Sc-22230 | 1:100 |
| GABA | Rabbit | Sigma | A2052 | 1:1000 |
| ChAT | Goat | Millipore | AB144P | 1:100 |
| 5-HT | Rabbit | Immunostar | 20080 | 1:1000 |

TABLE 5

Detailed information of primers used for quantitative RT-PCR in this work.

| Gene | Entrez ID | SEQ ID NO: | Forward | SEQ ID NO: | Reverse |
|---|---|---|---|---|---|
| GAPDH | 2597 | 1 | CAAGATCATCAGCAATGCCTCCTG | 2 | GCCTGCTTCACCACCTTCTTGA |
| OCT4 | 5460 | 3 | GTGGAGGAAGCTGACAACAA | 4 | ATTCTCCAGGTTGCCTCTCA |
| NANOG | 79923 | 5 | TTTGTGGGCCTGAAGAAAACT | 6 | AGGGCTGTCCTGAATAAGCAG |
| PAX6 | 5080 | 7 | TCCACCCGGCAGAAGATTGTA | 8 | TGTCTCGGATTTCCCAAGCAA |
| SOX1 | 6656 | 9 | GAACGCCTTCATGGTGTGGTC | 10 | TGTAATCCGGGTGCTCCTTCA |
| OTX2 | 5015 | 11 | CCAGACATCTTCATGCGAGAG | 12 | GGCAGGTCTCACTTTGTTTTG |
| CORIN | 10699 | 13 | AATCCCACAACAGAGCATCG | 14 | GGAGCAGTTGACCTCGTCAG |
| FOXA2 | 3170 | 15 | GGGGTAGTGCATCACCTGTT | 16 | CCGTTCTCCATCAACAACCT |
| MAP2 | 4133 | 17 | CGAAGCGCCAATGGATTCC | 18 | TGAACTATCCTTGCAGACACCT |
| TH | 7054 | 19 | TGTCTGAGGAGCCTGAGATTCG | 20 | GCTTGTCCTTGGCGTCACTG |
| PITX3 | 5309 | 21 | CCAACCTTAGTCCGTGCCAG | 22 | TGTGTAGGGCCTAGTCCACC |
| EN1 | 2019 | 23 | TCTCGCTGTCTCTCCCTCTC | 24 | CGTGGCTTACTCCCCATTTA |
| EN2 | 2020 | 25 | CCGGCGTGGGTCTACTGTA | 26 | CCTCTTTGTTCGGGTTCTTCTT |
| NURR1 | 4929 | 27 | GCTGGACTCCCCATTGCTTT | 28 | CGGAGCTGTATTCTCCCGAA |
| LMX1A | 4009 | 29 | ACGTCCGAGAACCATCTTGAC | 30 | CACCACCGTTTGTCTGAGC |
| LMX1B | 4010 | 31 | CGGACTGCGCCAAGATGTT | 32 | TTGACTCGCATCAGGAAGCG |
| DDC | 1644 | 33 | ATTCATCTGCCCTGAGTTCCG | 34 | CCAATAGCCATTTGTGGGGAT |
| ALDH1A1 | 216 | 35 | CCGTGGCGTACTATGGATGC | 36 | GCAGCAGACGATCTCTTTCGAT |
| ALDH1A2 | 8854 | 37 | GGGTGTGTTCTTCAATCAAGGT | 38 | TGGTGGGGTCAAAGGGACT |
| GIRK2 | 3763 | 39 | CACATCAGCCGAGATCGGAC | 40 | GGTAGCGATAGGTCTCCCTCA |

TABLE 5-continued

Detailed information of primers used for quantitative RT-PCR in this work.

| Gene | Entrez ID | SEQ ID NO: | Forward | SEQ ID NO: | Reverse |
|---|---|---|---|---|---|
| KCNS3 | 3790 | 41 | AGGAGCTGTGCGTATTCTCAT | 42 | CTTGCGTTCCTGGTAGCGATT |
| SOX6 | 55553 | 43 | AGGGAGTCTTGCCGATGTG | 44 | CAGGCTCTCAGGTGTACCTTTA |
| OXR1 | 55074 | 45 | TTCGACCAAACCTAAGTGATCCC | 46 | GGGGTGTCTAAACCTGTCATTG |
| SNCG | 6623 | 47 | TGAGCAGCGTCAACACTGTG | 48 | GAGGTGACCGCGATGTTCTC |
| SATB1 | 6304 | 49 | AGAGCTGTCAGTGGAAGGAAACA | 50 | GTGGCACTGTTGAACGAAACAAAT |
| ZDHHC2 | 51201 | 51 | TCCCGGTGGTGTTCATCAC | 52 | CAACTTGTTCGCCAGTGTTTTC |
| RAB3C | 115827 | 53 | GGAAGACGAGCGGGTCATC | 54 | CTCTCTGACATTTTGTCGCAGAT |
| FGF1 | 2246 | 55 | ACACCGACGGGCTTTTATACG | 56 | CCCATTCTTCTTGAGGCCAAC |
| GAD1 | 2571 | 57 | GCGGACCCCAATACCACTAAC | 58 | CACAAGGCGACTCTTCTCTTC |
| CALB1 | 793 | 59 | TGTGGATCAGTATGGGCAAAGA | 60 | CTCAGTTTCTATGAAGCCACTGT |
| CALB2 | 794 | 61 | AGCGCCGAGTTTATGGAGG | 62 | TGGTTTGGGTGTATTCCTGGA |
| TACR3 | 6870 | 63 | CTCTGGTCCCTGGCGTATG | 64 | TGAAGCGCGTAGATGAAATTGA |
| CARTPT | 9607 | 65 | CCGAGCCCTGGACATCTACT | 66 | ATGGGAACACGTTTACTCTTGAG |
| VGF | 7425 | 67 | CGCTGACCCGAGTGAATCTG | 68 | CATACGCGCCTGGAATTGA |
| VIP | 7432 | 69 | CCAAAACAAACCAGAACAGTCAGC | 70 | TGAGAAGAGTCAGGAGCACAAGG |
| LPL | 4023 | 71 | TCATTCCCGGAGTAGCAGAGT | 72 | GGCCACAAGTTTTGGCACC |
| EFNB3 | 1949 | 73 | CTCGGCGAATAAGAGGTTCCA | 74 | GTGAAGCGGAGATCCAGGTC |
| EGR1 | 1958 | 75 | GGTCAGTGGCCTAGTGAGC | 76 | GTGCCGCTGAGTAAATGGGA |
| FZD1 | 8321 | 77 | ATCGAAGCCAACTCACAGTATTT | 78 | CACGTTGTTAAGCCCCACG |
| ADCYAP1 | 116 | 79 | CCACTCGGACGGGATCTTC | 80 | GCCGCCAAGTATTTCTTGACAG |
| SDC2 | 6383 | 81 | TGGAAACCACGACGCTGAATA | 82 | ATAACTCCACCAGCAATGACAG |
| NEFM | 4741 | 83 | GAAATCGCTGCGTACAGAAAAC | 84 | TAATGGCTGTCAGGGCCTCTT |
| LRRK2 | 120892 | 85 | TTTTGATGCCATGCACTCATTTC | 86 | GGAATCGCTAGGGAATGTAAACA |
| PARK2 | 5071 | 87 | CCCACCTCTGACAAGGAAACA | 88 | TCGTGAACAAACTGCCGATCA |
| PARK7 | 11315 | 89 | AACCGGAAGGGCCTGATAG | 90 | GCAAGAGGGTGTGTTGTAACT |

TABLE 5-continued

Detailed information of primers used for quantitative RT-PCR in this work.

| Gene | Entrez ID | SEQ ID NO: | Forward | SEQ ID NO: | Reverse |
|---|---|---|---|---|---|
| SNCA | 6622 | 91 | AAGAGGGTGTTCTCTATGTAGGC | 92 | GCTCCTCCAACATTTGTCACTT |
| NCAM | 4137 | 93 | GGCTCCTTGGACTCATCTTTC | 94 | GACATCACCTGCTACTTCCTG |
| MAPT | 4137 | 95 | GAAGATTGGGTCCCTGGACAATA | 96 | AGGTCAGCTTGTGGGTTTCA |
| GAD2 | 2572 | 97 | CAAACATTTATCAACATGCGCTTC | 98 | CTATGACACTGGAGACAAGGC |
| VGAT | 140679 | 99 | AGATGATGAGAAACAACCCCAG | 100 | CACGACAAGCCCAAAATCAC |
| DLX5 | 1749 | 101 | ACAGAGACTTCACGACTCCCAG | 102 | TGTGGGGCTGCTCTGGTCTA |
| DLX6 | 1750 | 103 | TGGTGAAAGAGAAGCATTTGGACT | 104 | AGAGAAGGGCTGTTATGTGAGGAA |
| SERT | 6532 | 105 | TGCTGGCTTTTGCTAGCTAC | 106 | GAAGCTCGTCATGCAGTTCA |
| TPH2 | 121278 | 107 | ATGGCTCAGATCCCCTCTACA | 108 | GGATCCGCAAGTAGTGGAACA |
| VGLUT1 | 57030 | 109 | TCAAGTCCCCGATTCCGTGC | 110 | TGCGATTTTGGTTGTTTCCCCA |
| VGLUT2 | 57084 | 111 | TGGGGCTACATCATCACTCA | 112 | GAAGTATGGCAGCTCCGAAA |

REFERENCES

Bush, W. D., Garguilo, J., Zucca, F. A., Albertini, A., Zecca, L., Edwards, G. S., Nemanich, R. J., and Simon, J. D. (2006). The surface oxidation potential of human neuromelanin reveals a spherical architecture with a pheomelanin core and a eumelanin surface. Proceedings of the National Academy of Sciences of the United States of America 103, 14785-14789.

Carriel, V. S., Aneiros-Fernandez, J., Arias-Santiago, S., Garzon, I. J., Alaminos, M., and Campos, A. (2011). A novel histochemical method for a simultaneous staining of melanin and collagen fibers. The journal of histochemistry and cytochemistry: official journal of the Histochemistry Society 59, 270-277.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nature biotechnology 27, 275-280.

Consortium, G. T. (2015). Human genomics. The Genotype-Tissue Expression (GTEx) pilot analysis: multitissue gene regulation in humans. Science 348, 648-660.

Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome Biol 5, R80.

Jaffe, A. E., Shin, J., Collado-Torres, L., Leek, J. T., Tao, R., Li, C., Gao, Y., Jia, Y., Maher, B. J., Hyde, T. M., et al. (2015). Developmental regulation of human cortex transcription and its clinical relevance at single base resolution. Nature neuroscience 18, 154-161.

James A. Thomson, Joseph Itskovitz-Eldor, Sander S. Shapiro, Michelle A. Waknitz, Jennifer J. Swiergiel, Vivienne S. Marshall, Jeffrey M. Jones (1998). Embryonic Stem Cell Lines Derived from Human Blastocysts. Science 282, 1145-1147

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol 14, R36.

Kriks, S., Shim, J. W., Piao, J., Ganat, Y. M., Wakeman, D. R., Xie, Z., Carrillo-Reid, L., Auyeung, G., Antonacci, C., Buch, A., et al. (2011). Dopamine neurons derived from human ES cells efficiently engraft in animal models of Parkinson's disease. Nature 480, 547-551.

Lancaster, M. A., and Knoblich, J. A. (2014). Generation of cerebral organoids from human pluripotent stem cells. Nature protocols 9, 2329-2340.

Lancaster, M. A., Renner, M., Martin, C. A., Wenzel, D., Bicknell, L. S., Hurles, M. E., Homfray, T., Penninger, J. M., Jackson, A. P., and Knoblich, J. A. (2013). Cerebral organoids model human brain development and microcephaly. Nature 501, 373-379.

Lawrence, M., Huber, W., Pages, H., Aboyoun, P., Carlson, M., Gentleman, R., Morgan, M. T., and Carey, V. J. (2013). Software for computing and annotating genomic ranges. PLoS Comput Biol 9, e1003118.

Lin, L., Goke, J., Cukuroglu, E., Dranias, M. R., VanDongen, A. M., and Stanton, L. W. (2016). Molecular Features Underlying Neurodegeneration Identified through In Vitro Modeling of Genetically Diverse Parkinson's Disease Patients. Cell reports 15, 2411-2426.

Love, M. I., Huber, W., and Anders, S. (2014). Moderated estimation of fold change and dispersion for RNA-seq data with DESeq2. Genome biology 15, 550.

Nighswander-Rempel, S. P., Riesz, J., Gilmore, J., Bothma, J. P., and Meredith, P. (2005). Quantitative fluorescence excitation spectra of synthetic eumelanin. The journal of physical chemistry B 109, 20629-20635.

Team, R. D. C. (2014). R: A Language and Environment for Statistical Computing. R Foundation for Statistical Computing.

Wickham, H. (2009). ggplot2: elegant graphics for data analysis. In (Springer New York).

Zecca, L., Fariello, R., Riederer, P., Sulzer, D., Gatti, A., and Tampellini, D. (2002). The absolute concentration of nigral neuromelanin, assayed by a new sensitive method, increases throughout the life and is dramatically decreased in Parkinson's disease. FEBS letters 510, 216-220.

What is claimed is:

1. A method of deriving and maintaining a midbrain-like organoid comprising:
   (a) culturing pluripotent stem cells in a first cell culture medium to obtain neuronal lineage embryoid bodies, wherein culturing under (a) is for 3 to 5 days;
   (b) culturing the neuronal lineage embryoid bodies from (a) in a second cell culture medium to obtain midbrain regionalized tissues, wherein culturing under (b) is for 3 to 5 days, wherein the midbrain regionalized tissues are OTX2 positive and negative for FOXG1 and GBX2;
   (c) embedding and culturing the midbrain regionalized tissues from (b) in an extracellular matrix in a third cell culture medium to obtain developing neuroepithelial tissues, wherein culturing under (c) is for 1 to 2 days;
   (d) culturing the neuroepithelial tissues from (c) to obtain a midbrain-like organoid, wherein the neuroepithelial tissues of operation (d) are cultured in a fourth cell culture medium, and,
   (e) maintaining the midbrain-like organoid from (d) wherein the midbrain-like organoid is cultured in a neuronal culture media comprising neurotrophic factor, wherein the first cell culture medium comprises:
      (i) TGF-β inhibitor and/or SMAD2/3 inhibitor; and
      (ii) WNT-signaling activator;
   wherein the second cell culture medium comprises:
      (iii) TGF-β inhibitor and/or SMAD2/3 inhibitor;
      (iv) WNT-signaling activator;
      (v) hedgehog signaling protein;
      (vi) fibroblast growth factor;
   wherein the third cell culture medium comprises:
      (vii) hedgehog signaling protein; and
      (viii) fibroblast growth factor,
   wherein the fourth cell culture medium comprises:
      (ix) neurotrophic factor;
      (x) ascorbic acid; and
      (xi) activator of cAMP-dependent pathways,
   and wherein the resulting midbrain-like organoid is OTX2 positive and negative for FOXG1 and GBX2.

2. The method of claim 1, wherein the extracellular matrix promotes cell differentiation and/or can maintain three-dimensional culture and/or promotes the development of complex tissue and is made of a material selected from the group consisting of synthetic polymer, or polymer scaffolds and solid support materials.

3. The method of claim 1, wherein the TGF-β inhibitor and/or SMAD2/3 inhibitor is selected from the group consisting of 4-[4-(1,3-benzodioxol-5-yl)-5-pyridin-2-yl-1H-imidazol-2-yl]benzamide (SB 431542), and (1R,4r)-4-((R)-1-aminoethyl)-N-(pyridin-4-yl)cyclohexanecarboxamide (ROCK inhibitor Y27632), and derivatives thereof.

4. The method of claim 1, wherein the hedgehog signaling protein is selected from the group consisting of: Desert hedgehog homolog (DHH), Indian hedgehog homolog (IHH) and Sonic hedgehog (SHH).

5. The method of claim 1, wherein the neurotrophic factor of the neuronal culture medium of step (e) and the fourth cell culture medium is selected from the group consisting of neurotrophin, glial cell-line derived neurotrophic factor family ligand (GFL), and neuropoietic cytokine.

6. The method of claim 1, wherein the activator of cAMP-dependent pathways is dibutyryl-cAMP (dbCAMP).

7. The method of claim 1, wherein the first cell culture medium further comprises a basal cell growth medium at a percentage of 40% to 50%, a basal embryonic neuronal cell growth medium at a percentage of 40% to 50%, a glutamine supplement at a percentage of 0.5% to 3%, a non-essential amino acid (NEAA) supplement at a percentage of 0.5% to 3%, antibiotics at a percentage of 0.5% to 3%, a reducing agent at a percentage of 0.05% to 0.5%, a supplement for expansion of undifferentiated cells, at a percentage of 0.5% to 3%, a supplement for the maintenance of neurons, at a percentage of 0.5% to 5% and a supplement for cell proliferation, at a concentration of 0.1 to 5 μg/ml.

8. The method of claim 1, wherein the fourth cell culture medium further comprises a basal embryonic neuronal cell growth medium at a percentage of 90% to 95%, a glutamine supplement at a percentage of 0.5% to 3%, a non-essential amino acid (NEAA) supplement at a percentage of 0.5% to 3%, antibiotics at a percentage of 0.5% to 3%, a reducing agent at a percentage of 0.05% to 0.5%, a supplement for expansion of undifferentiated cells, at a percentage of 0.5% to 3%, a supplement for the maintenance of neurons, at a percentage of 0.5% to 5%, a growth supplement at a concentration of 0.5 to 10 μg/ml, and a growth enhancer of stem cells at the concentration of 50 to 500 ng/ml.

9. The method of claim 7, wherein the basal cell growth medium is Dulbecco's Modified Eagle's Medium (DMEM)/Nutrient F-12.

10. The method of claim 7, wherein the basal embryonic neuronal cell growth medium is Neurobasal medium.

11. The method of claim 7, wherein the supplement for cell proliferation is heparin.

12. The method of claim 1 wherein the midbrain regionalized tissues are OTX2 positive and negative for FOXG1 and GBX2 as determined by immunohistochemical staining.

13. The method of claim 1, wherein the extracellular matrix is selected from the group consisting of gelatin, methylcellulose, collagen, alginate beads, agarose, fibrin, fibrin glue, fibrinogen, blood plasma fibrin beads, whole plasma or components thereof, laminins, fibronectins, proteoglycans, HSP, chitosan and heparin, or a combination thereof.

14. The method of claim 1, wherein the WNT-signaling activator is a GSK3 inhibitor.

15. The method of claim 14, wherein the GSK3 inhibitor is CHIR-99021 6-[2-[[4-(2,4-dichlorophenyl)-5-(5-methyl-1H-imidazol-2-yl)pyrimidin-2-yl]amino]ethylamino]pyridine-3-carbonitrile.

16. The method of claim 1, wherein the fibroblast growth factor is FGF8.

17. The method of claim 5, wherein the neurotrophin is selected from the group consisting of nerve growth factor (NGF), brain-derived neurotrophic factor (BDNF), neurotrophin-3 (NT-3) and neurotrophin-4 (NT-4).

18. The method of claim 5, wherein the GFL is selected from the group consisting of glial cell line-derived neurotrophic factor (GDNF), neurturin (NRTN), artemin (ARTN) and persephin (PSPN).

19. The method of claim 1, wherein the second cell culture medium further comprises a basal cell growth medium at a percentage of 40% to 50%, a basal embryonic neuronal cell growth medium at a percentage of 40% to 50%, a glutamine supplement at a percentage of 0.5% to 3%, a non-essential amino acid (NEAA) supplement at a percentage of 0.5% to 3%, antibiotics at a percentage of 0.5% to 3%, a reducing agent at a percentage of 0.05% to 0.5%, a supplement for expansion of undifferentiated cells, at a percentage of 0.5% to 3%, a supplement for the maintenance of neurons, at a percentage of 0.5% to 5% and a supplement for cell proliferation, at a concentration of 0.1 to 5 µg/ml.

20. The method of claim 1, wherein the third cell culture medium further comprises a basal embryonic neuronal cell growth medium at a percentage of 90% to 95%, a glutamine supplement at a percentage of 0.5% to 3%, a non-essential amino acid (NEAA) supplement at a percentage of 0.5% to 3%, antibiotics at a percentage of 0.5% to 3%, a reducing agent at a percentage of 0.05% to 0.5%, a supplement for expansion of undifferentiated cells, at a percentage of 0.5% to 3%, a supplement for the maintenance of neurons, at a percentage of 0.5% to 5%, a growth supplement at a concentration of 0.5 to 10 µg/ml, and a growth enhancer of stem cells at the concentration of 50 to 500 ng/ml.

21. The method of claim 7, wherein the glutamine supplement is L-alanyl-L-glutamine dipeptide.

22. The method of claim 7, wherein the antibiotics are penicillin/streptomycin.

23. The method of claim 7, wherein the reducing agent is β-mercaptoethanol.

24. The method of claim 7, wherein the supplement for expansion of undifferentiated cells is N-2 Supplement.

25. The method of claim 7, wherein the supplement for the maintenance of neurons is B27 without vitamin-A.

26. The method of claim 7, wherein the growth supplement is insulin.

27. The method of claim 7, wherein the growth enhancer of stem cells is laminin.

* * * * *

SEQUENCE LISTING

```
<160> NUMBER OF SEQ ID NOS: 112

<210> SEQ ID NO 1
<211> LENGTH: 24
<212> TYPE: DNA
<213> ORGANISM: Artificial sequence
<220> FEATURE:
<223> OTHER INFORMATION: GAPDH forward primer

<400> SEQUENCE: 1
caagatcatc agcaatgcct cctg                                          24

<210> SEQ ID NO 2
<211> LENGTH: 22
<212> TYPE: DNA
<213> ORGANISM: Artificial sequence
<220> FEATURE:
<223> OTHER INFORMATION: GAPDH reverse primer

<400> SEQUENCE: 2
gcctgcttca ccaccttctt ga                                            22

<210> SEQ ID NO 3
<211> LENGTH: 20
<212> TYPE: DNA
<213> ORGANISM: Artificial sequence
<220> FEATURE:
<223> OTHER INFORMATION: OCT4 forward primer

<400> SEQUENCE: 3
gtggaggaag ctgacaacaa                                               20

<210> SEQ ID NO 4
<211> LENGTH: 20
<212> TYPE: DNA
<213> ORGANISM: Artificial sequence
<220> FEATURE:
<223> OTHER INFORMATION: OCT4 reverse primer

<400> SEQUENCE: 4
attctccagg ttgcctctca                                               20

<210> SEQ ID NO 5
<211> LENGTH: 21
<212> TYPE: DNA
<213> ORGANISM: Artificial sequence
<220> FEATURE:
<223> OTHER INFORMATION: NANOG forward primer

<400> SEQUENCE: 5
tttgtgggcc tgaagaaaac t                                             21

<210> SEQ ID NO 6
<211> LENGTH: 21
<212> TYPE: DNA
```

```
<213> ORGANISM: Artificial sequence
<220> FEATURE:
<223> OTHER INFORMATION: NANOG reverse primer

<400> SEQUENCE: 6
agggctgtcc tgaataagca g                                              21

<210> SEQ ID NO 7
<211> LENGTH: 21
<212> TYPE: DNA
<213> ORGANISM: Artificial sequence
<220> FEATURE:
<223> OTHER INFORMATION: PAX6 forward primer

<400> SEQUENCE: 7
tccacccggc agaagattgt a                                              21

<210> SEQ ID NO 8
<211> LENGTH: 21
<212> TYPE: DNA
<213> ORGANISM: Artificial sequence
<220> FEATURE:
<223> OTHER INFORMATION: PAX6 reverse primer

<400> SEQUENCE: 8
tgtctcggat ttcccaagca a                                              21

<210> SEQ ID NO 9
<211> LENGTH: 21
<212> TYPE: DNA
<213> ORGANISM: Artificial sequence
<220> FEATURE:
<223> OTHER INFORMATION: SOX1 forward primer

<400> SEQUENCE: 9
gaacgccttc atggtgtggt c                                              21

<210> SEQ ID NO 10
<211> LENGTH: 21
<212> TYPE: DNA
<213> ORGANISM: Artificial sequence
<220> FEATURE:
<223> OTHER INFORMATION: SOX1 reverse primer

<400> SEQUENCE: 10
tgtaatccgg gtgctccttc a                                              21

<210> SEQ ID NO 11
<211> LENGTH: 21
<212> TYPE: DNA
<213> ORGANISM: Artificial sequence
<220> FEATURE:
<223> OTHER INFORMATION: OTX2 forward primer

<400> SEQUENCE: 11
ccagacatct tcatgcgaga g                                              21

<210> SEQ ID NO 12
<211> LENGTH: 21
<212> TYPE: DNA
<213> ORGANISM: Artificial sequence
<220> FEATURE:
<223> OTHER INFORMATION: OTX2 reverse primer

<400> SEQUENCE: 12
ggcaggtctc actttgttttg                                               21
```

<210> SEQ ID NO 13
<211> LENGTH: 20
<212> TYPE: DNA
<213> ORGANISM: Artificial sequence
<220> FEATURE:
<223> OTHER INFORMATION: CORIN forward primer

<400> SEQUENCE: 13
aatcccacaa cagagcatcg                                                    20

<210> SEQ ID NO 14
<211> LENGTH: 20
<212> TYPE: DNA
<213> ORGANISM: Artificial sequence
<220> FEATURE:
<223> OTHER INFORMATION: CORIN reverse primer

<400> SEQUENCE: 14
ggagcagttg acctcgtcag                                                    20

<210> SEQ ID NO 15
<211> LENGTH: 20
<212> TYPE: DNA
<213> ORGANISM: Artificial sequence
<220> FEATURE:
<223> OTHER INFORMATION: FOXA2 forward primer

<400> SEQUENCE: 15
ggggtagtgc atcacctgtt                                                    20

<210> SEQ ID NO 16
<211> LENGTH: 20
<212> TYPE: DNA
<213> ORGANISM: Artificial sequence
<220> FEATURE:
<223> OTHER INFORMATION: FOXA2 reverse primer

<400> SEQUENCE: 16
ccgttctcca tcaacaacct                                                    20

<210> SEQ ID NO 17
<211> LENGTH: 19
<212> TYPE: DNA
<213> ORGANISM: Artificial sequence
<220> FEATURE:
<223> OTHER INFORMATION: MAP2 forward primer

<400> SEQUENCE: 17
cgaagcgcca atggattcc                                                     19

<210> SEQ ID NO 18
<211> LENGTH: 22
<212> TYPE: DNA
<213> ORGANISM: Artificial sequence
<220> FEATURE:
<223> OTHER INFORMATION: MAP2 reverse primer

<400> SEQUENCE: 18
tgaactatcc ttgcagacac ct                                                 22

<210> SEQ ID NO 19
<211> LENGTH: 22
<212> TYPE: DNA
<213> ORGANISM: Artificial sequence
<220> FEATURE:

```
<223> OTHER INFORMATION: TH forward primer

<400> SEQUENCE: 19
tgtctgagga gcctgagatt cg                                              22

<210> SEQ ID NO 20
<211> LENGTH: 20
<212> TYPE: DNA
<213> ORGANISM: Artificial sequence
<220> FEATURE:
<223> OTHER INFORMATION: TH reverse primer

<400> SEQUENCE: 20
gcttgtcctt ggcgtcactg                                                 20

<210> SEQ ID NO 21
<211> LENGTH: 20
<212> TYPE: DNA
<213> ORGANISM: Artificial sequence
<220> FEATURE:
<223> OTHER INFORMATION: PITX3 forward primer

<400> SEQUENCE: 21
ccaaccttag tccgtgccag                                                 20

<210> SEQ ID NO 22
<211> LENGTH: 20
<212> TYPE: DNA
<213> ORGANISM: Artificial sequence
<220> FEATURE:
<223> OTHER INFORMATION: PITX3 reverse primer

<400> SEQUENCE: 22
tgtgtagggc ctagtccacc                                                 20

<210> SEQ ID NO 23
<211> LENGTH: 20
<212> TYPE: DNA
<213> ORGANISM: Artificial sequence
<220> FEATURE:
<223> OTHER INFORMATION: EN1 forward primer

<400> SEQUENCE: 23
tctcgctgtc tctccctctc                                                 20

<210> SEQ ID NO 24
<211> LENGTH: 20
<212> TYPE: DNA
<213> ORGANISM: Artificial sequence
<220> FEATURE:
<223> OTHER INFORMATION: EN1 reverse primer

<400> SEQUENCE: 24
cgtggcttac tccccattta                                                 20

<210> SEQ ID NO 25
<211> LENGTH: 19
<212> TYPE: DNA
<213> ORGANISM: Artificial sequence
<220> FEATURE:
<223> OTHER INFORMATION: EN2 forward primer

<400> SEQUENCE: 25
ccggcgtggg tctactgta                                                  19
```

<210> SEQ ID NO 26
<211> LENGTH: 22
<212> TYPE: DNA
<213> ORGANISM: Artificial sequence
<220> FEATURE:
<223> OTHER INFORMATION: EN2 reverse primer

<400> SEQUENCE: 26
cctctttgtt cgggttcttc tt                                    22

<210> SEQ ID NO 27
<211> LENGTH: 20
<212> TYPE: DNA
<213> ORGANISM: Artificial sequence
<220> FEATURE:
<223> OTHER INFORMATION: NURR1 forward primer

<400> SEQUENCE: 27
gctggactcc ccattgcttt                                       20

<210> SEQ ID NO 28
<211> LENGTH: 20
<212> TYPE: DNA
<213> ORGANISM: Artificial sequence
<220> FEATURE:
<223> OTHER INFORMATION: NURR1 reverse primer

<400> SEQUENCE: 28
cggagctgta ttctcccgaa                                       20

<210> SEQ ID NO 29
<211> LENGTH: 21
<212> TYPE: DNA
<213> ORGANISM: Artificial sequence
<220> FEATURE:
<223> OTHER INFORMATION: LMX1A forward primer

<400> SEQUENCE: 29
acgtccgaga accatcttga c                                     21

<210> SEQ ID NO 30
<211> LENGTH: 19
<212> TYPE: DNA
<213> ORGANISM: Artificial sequence
<220> FEATURE:
<223> OTHER INFORMATION: LMX1A reverse primer

<400> SEQUENCE: 30
caccaccgtt tgtctgagc                                        19

<210> SEQ ID NO 31
<211> LENGTH: 19
<212> TYPE: DNA
<213> ORGANISM: Artificial sequence
<220> FEATURE:
<223> OTHER INFORMATION: LMX1B forward primer

<400> SEQUENCE: 31
cggactgcgc caagatgtt                                        19

<210> SEQ ID NO 32
<211> LENGTH: 20
<212> TYPE: DNA
<213> ORGANISM: Artificial sequence
<220> FEATURE:
<223> OTHER INFORMATION: LMX1B reverse primer

```
<400> SEQUENCE: 32
ttgactcgca tcaggaagcg                                                    20

<210> SEQ ID NO 33
<211> LENGTH: 21
<212> TYPE: DNA
<213> ORGANISM: Artificial sequence
<220> FEATURE:
<223> OTHER INFORMATION: DDC forward primer

<400> SEQUENCE: 33
attcatctgc cctgagttcc g                                                  21

<210> SEQ ID NO 34
<211> LENGTH: 21
<212> TYPE: DNA
<213> ORGANISM: Artificial sequence
<220> FEATURE:
<223> OTHER INFORMATION: DDC reverse primer

<400> SEQUENCE: 34
ccaatagcca tttgtgggga t                                                  21

<210> SEQ ID NO 35
<211> LENGTH: 20
<212> TYPE: DNA
<213> ORGANISM: Artificial sequence
<220> FEATURE:
<223> OTHER INFORMATION: ALDH1A1 forward primer

<400> SEQUENCE: 35
ccgtggcgta ctatggatgc                                                    20

<210> SEQ ID NO 36
<211> LENGTH: 22
<212> TYPE: DNA
<213> ORGANISM: Artificial sequence
<220> FEATURE:
<223> OTHER INFORMATION: ALDH1A1 reverse primer

<400> SEQUENCE: 36
gcagcagacg atctctttcg at                                                 22

<210> SEQ ID NO 37
<211> LENGTH: 22
<212> TYPE: DNA
<213> ORGANISM: Artificial sequence
<220> FEATURE:
<223> OTHER INFORMATION: ALDH1A2 forward primer

<400> SEQUENCE: 37
gggtgtgttc ttcaatcaag gt                                                 22

<210> SEQ ID NO 38
<211> LENGTH: 19
<212> TYPE: DNA
<213> ORGANISM: Artificial sequence
<220> FEATURE:
<223> OTHER INFORMATION: ALDH1A2 reverse primer

<400> SEQUENCE: 38 tggtgggtc aaagggact                                                      19

<210> SEQ ID NO 39
<211> LENGTH: 20
```

```
<212> TYPE: DNA
<213> ORGANISM: Artificial sequence
<220> FEATURE:
<223> OTHER INFORMATION: GIRK2 forward primer

<400> SEQUENCE: 39
cacatcagcc gagatcggac                                              20

<210> SEQ ID NO 40
<211> LENGTH: 21
<212> TYPE: DNA
<213> ORGANISM: Artificial sequence
<220> FEATURE:
<223> OTHER INFORMATION: GIRK2 reverse primer

<400> SEQUENCE: 40
ggtagcgata ggtctccctc a                                            21

<210> SEQ ID NO 41
<211> LENGTH: 21
<212> TYPE: DNA
<213> ORGANISM: Artificial sequence
<220> FEATURE:
<223> OTHER INFORMATION: KCNS3 forward primer

<400> SEQUENCE: 41
aggagctgtg cgtattctca t                                            21

<210> SEQ ID NO 42
<211> LENGTH: 21
<212> TYPE: DNA
<213> ORGANISM: Artificial sequence
<220> FEATURE:
<223> OTHER INFORMATION: KCNS3 reverse primer

<400> SEQUENCE: 42
cttgcgttcc tggtagcgat t                                            21

<210> SEQ ID NO 43
<211> LENGTH: 19
<212> TYPE: DNA
<213> ORGANISM: Artificial sequence
<220> FEATURE:
<223> OTHER INFORMATION: SOX6 forward primer

<400> SEQUENCE: 43
agggagtctt gccgatgtg                                               19

<210> SEQ ID NO 44
<211> LENGTH: 22
<212> TYPE: DNA
<213> ORGANISM: Artificial sequence
<220> FEATURE:
<223> OTHER INFORMATION: SOX6 reverse primer

<400> SEQUENCE: 44
caggctctca ggtgtacctt ta                                           22

<210> SEQ ID NO 45
<211> LENGTH: 23
<212> TYPE: DNA
<213> ORGANISM: Artificial sequence
<220> FEATURE:
<223> OTHER INFORMATION: OXR1 forward primer

<400> SEQUENCE: 45
```
ttcgaccaaa cctaagtgat ccc                                            23

<210> SEQ ID NO 46
<211> LENGTH: 22
<212> TYPE: DNA
<213> ORGANISM: Artificial sequence
<220> FEATURE:
<223> OTHER INFORMATION: OXR1 reverse primer

<400> SEQUENCE: 46
ggggtgtcta aacctgtcat tg                                             22

<210> SEQ ID NO 47
<211> LENGTH: 20
<212> TYPE: DNA
<213> ORGANISM: Artificial sequence
<220> FEATURE:
<223> OTHER INFORMATION: SNCG forward primer

<400> SEQUENCE: 47
tgagcagcgt caacactgtg                                                20

<210> SEQ ID NO 48
<211> LENGTH: 20
<212> TYPE: DNA
<213> ORGANISM: Artificial sequence
<220> FEATURE:
<223> OTHER INFORMATION: SNCG reverse primer

<400> SEQUENCE: 48
gaggtgaccg cgatgttctc                                                20

<210> SEQ ID NO 49
<211> LENGTH: 23
<212> TYPE: DNA
<213> ORGANISM: Artificial sequence
<220> FEATURE:
<223> OTHER INFORMATION: SATB1 forward primer

<400> SEQUENCE: 49
agagctgtca gtggaaggaa aca                                            23

<210> SEQ ID NO 50
<211> LENGTH: 24
<212> TYPE: DNA
<213> ORGANISM: Artificial sequence
<220> FEATURE:
<223> OTHER INFORMATION: SATB1 reverse primer

<400> SEQUENCE: 50
gtggcactgt tgaacgaaac aaat                                           24

<210> SEQ ID NO 51
<211> LENGTH: 19
<212> TYPE: DNA
<213> ORGANISM: Artificial sequence
<220> FEATURE:
<223> OTHER INFORMATION: ZDHHC2 forward primer

<400> SEQUENCE: 51
tcccggtggt gttcatcac                                                 19

<210> SEQ ID NO 52
<211> LENGTH: 22
<212> TYPE: DNA
<213> ORGANISM: Artificial sequence

```
<220> FEATURE:
<223> OTHER INFORMATION: ZDHHC2 reverse primer

<400> SEQUENCE: 52
caacttgttc gccagtgttt tc                                              22

<210> SEQ ID NO 53
<211> LENGTH: 19
<212> TYPE: DNA
<213> ORGANISM: Artificial sequence
<220> FEATURE:
<223> OTHER INFORMATION: RAB3C forward primer

<400> SEQUENCE: 53
ggaagacgag cgggtcatc                                                  19

<210> SEQ ID NO 54
<211> LENGTH: 23
<212> TYPE: DNA
<213> ORGANISM: Artificial sequence
<220> FEATURE:
<223> OTHER INFORMATION: RAB3C reverse primer

<400> SEQUENCE: 54
ctctctgaca ttttgtcgca gat                                             23

<210> SEQ ID NO 55
<211> LENGTH: 21
<212> TYPE: DNA
<213> ORGANISM: Artificial sequence
<220> FEATURE:
<223> OTHER INFORMATION: FGF1 forward primer

<400> SEQUENCE: 55
acaccgacgg gcttttatac g                                               21

<210> SEQ ID NO 56
<211> LENGTH: 21
<212> TYPE: DNA
<213> ORGANISM: Artificial sequence
<220> FEATURE:
<223> OTHER INFORMATION: FGF1 reverse primer

<400> SEQUENCE: 56
cccattcttc ttgaggccaa c                                               21

<210> SEQ ID NO 57
<211> LENGTH: 21
<212> TYPE: DNA
<213> ORGANISM: Artificial sequence
<220> FEATURE:
<223> OTHER INFORMATION: GAD1 forward primer

<400> SEQUENCE: 57
gcggacccca ataccactaa c                                               21

<210> SEQ ID NO 58
<211> LENGTH: 21
<212> TYPE: DNA
<213> ORGANISM: Artificial sequence
<220> FEATURE:
<223> OTHER INFORMATION: GAD1 reverse primer

<400> SEQUENCE: 58
cacaaggcga ctcttctctt c                                               21
```

```
<210> SEQ ID NO 59
<211> LENGTH: 22
<212> TYPE: DNA
<213> ORGANISM: Artificial sequence
<220> FEATURE:
<223> OTHER INFORMATION: CALB1 foward primer

<400> SEQUENCE: 59
tgtggatcag tatgggcaaa ga                                             22

<210> SEQ ID NO 60
<211> LENGTH: 23
<212> TYPE: DNA
<213> ORGANISM: Artificial sequence
<220> FEATURE:
<223> OTHER INFORMATION: CALB1 reverse primer

<400> SEQUENCE: 60
ctcagtttct atgaagccac tgt                                            23

<210> SEQ ID NO 61
<211> LENGTH: 19
<212> TYPE: DNA
<213> ORGANISM: Artificial sequence
<220> FEATURE:
<223> OTHER INFORMATION: CALB2 forward primer

<400> SEQUENCE: 61
agcgccgagt ttatggagg                                                 19

<210> SEQ ID NO 62
<211> LENGTH: 21
<212> TYPE: DNA
<213> ORGANISM: Artificial sequence
<220> FEATURE:
<223> OTHER INFORMATION: CALB2 reverse primer

<400> SEQUENCE: 62
tggtttgggt gtattcctgg a                                              21

<210> SEQ ID NO 63
<211> LENGTH: 19
<212> TYPE: DNA
<213> ORGANISM: Artificial sequence
<220> FEATURE:
<223> OTHER INFORMATION: TACR3 forward primer

<400> SEQUENCE: 63
ctctggtccc tggcgtatg                                                 19

<210> SEQ ID NO 64
<211> LENGTH: 22
<212> TYPE: DNA
<213> ORGANISM: Artificial sequence
<220> FEATURE:
<223> OTHER INFORMATION: TACR3 reverse primer

<400> SEQUENCE: 64
tgaagcgcgt agatgaaatt ga                                             22

<210> SEQ ID NO 65
<211> LENGTH: 20
<212> TYPE: DNA
<213> ORGANISM: Artificial sequence
<220> FEATURE:
<223> OTHER INFORMATION: CARTPT forward primer
```

<400> SEQUENCE: 65
ccgagccctg gacatctact                                              20

<210> SEQ ID NO 66
<211> LENGTH: 23
<212> TYPE: DNA
<213> ORGANISM: Artificial sequence
<220> FEATURE:
<223> OTHER INFORMATION: CARTPT reverse primer

<400> SEQUENCE: 66
atgggaacac gtttactctt gag                                          23

<210> SEQ ID NO 67
<211> LENGTH: 20
<212> TYPE: DNA
<213> ORGANISM: Artificial sequence
<220> FEATURE:
<223> OTHER INFORMATION: VGF forward primer

<400> SEQUENCE: 67
cgctgacccg agtgaatctg                                              20

<210> SEQ ID NO 68
<211> LENGTH: 19
<212> TYPE: DNA
<213> ORGANISM: Artificial sequence
<220> FEATURE:
<223> OTHER INFORMATION: VGF reverse primer

<400> SEQUENCE: 68
catacgcgcc tggaattga                                               19

<210> SEQ ID NO 69
<211> LENGTH: 24
<212> TYPE: DNA
<213> ORGANISM: Artificial sequence
<220> FEATURE:
<223> OTHER INFORMATION: VIP forward primer

<400> SEQUENCE: 69
ccaaaacaaa ccagaacagt cagc                                         24

<210> SEQ ID NO 70
<211> LENGTH: 23
<212> TYPE: DNA
<213> ORGANISM: Artificial sequence
<220> FEATURE:
<223> OTHER INFORMATION: VIP reverse primer

<400> SEQUENCE: 70
tgagaagagt caggagcaca agg                                          23

<210> SEQ ID NO 71
<211> LENGTH: 21
<212> TYPE: DNA
<213> ORGANISM: Artificial sequence
<220> FEATURE:
<223> OTHER INFORMATION: LPL forward primer

<400> SEQUENCE: 71
tcattcccgg agtagcagag t                                            21

<210> SEQ ID NO 72

```
<211> LENGTH: 19
<212> TYPE: DNA
<213> ORGANISM: Artificial sequence
<220> FEATURE:
<223> OTHER INFORMATION: LPL reverse primer

<400> SEQUENCE: 72
ggccacaagt tttggcacc                                                   19

<210> SEQ ID NO 73
<211> LENGTH: 21
<212> TYPE: DNA
<213> ORGANISM: Artificial sequence
<220> FEATURE:
<223> OTHER INFORMATION: EFNB3 forward primer

<400> SEQUENCE: 73
ctcggcgaat aagaggttcc a                                                21

<210> SEQ ID NO 74
<211> LENGTH: 20
<212> TYPE: DNA
<213> ORGANISM: Artificial sequence
<220> FEATURE:
<223> OTHER INFORMATION: EFNB3 reverse primer

<400> SEQUENCE: 74
gtgaagcgga gatccaggtc                                                  20

<210> SEQ ID NO 75
<211> LENGTH: 19
<212> TYPE: DNA
<213> ORGANISM: Artificial sequence
<220> FEATURE:
<223> OTHER INFORMATION: EGR1 forward primer

<400> SEQUENCE: 75
ggtcagtggc ctagtgagc                                                   19

<210> SEQ ID NO 76
<211> LENGTH: 20
<212> TYPE: DNA
<213> ORGANISM: Artificial sequence
<220> FEATURE:
<223> OTHER INFORMATION: EGR1 reverse primer

<400> SEQUENCE: 76
gtgccgctga gtaaatggga                                                  20

<210> SEQ ID NO 77
<211> LENGTH: 23
<212> TYPE: DNA
<213> ORGANISM: Artificial sequence
<220> FEATURE:
<223> OTHER INFORMATION: FZD1 forward primer

<400> SEQUENCE: 77
atcgaagcca actcacagta ttt                                              23

<210> SEQ ID NO 78
<211> LENGTH: 19
<212> TYPE: DNA
<213> ORGANISM: Artificial sequence
<220> FEATURE:
<223> OTHER INFORMATION: FZD1 reverse primer

<400> SEQUENCE: 78
```

```
cacgttgtta agccccacg                                          19
```

<210> SEQ ID NO 79
<211> LENGTH: 19
<212> TYPE: DNA
<213> ORGANISM: Artificial sequence
<220> FEATURE:
<223> OTHER INFORMATION: ADCYAP1 forward primer

<400> SEQUENCE: 79

```
ccactcggac gggatcttc                                          19
```

<210> SEQ ID NO 80
<211> LENGTH: 22
<212> TYPE: DNA
<213> ORGANISM: Artificial sequence
<220> FEATURE:
<223> OTHER INFORMATION: ADCYAP1 reverse primer

<400> SEQUENCE: 80

```
gccgccaagt atttcttgac ag                                      22
```

<210> SEQ ID NO 81
<211> LENGTH: 21
<212> TYPE: DNA
<213> ORGANISM: Artificial sequence
<220> FEATURE:
<223> OTHER INFORMATION: SDC2 forward primer

<400> SEQUENCE: 81

```
tggaaaccac gacgctgaat a                                       21
```

<210> SEQ ID NO 82
<211> LENGTH: 22
<212> TYPE: DNA
<213> ORGANISM: Artificial sequence
<220> FEATURE:
<223> OTHER INFORMATION: SDC2 reverse primer

<400> SEQUENCE: 82

```
ataactccac cagcaatgac ag                                      22
```

<210> SEQ ID NO 83
<211> LENGTH: 22
<212> TYPE: DNA
<213> ORGANISM: Artificial sequence
<220> FEATURE:
<223> OTHER INFORMATION: NEFM forward primer

<400> SEQUENCE: 83

```
gaaatcgctg cgtacagaaa ac                                      22
```

<210> SEQ ID NO 84
<211> LENGTH: 21
<212> TYPE: DNA
<213> ORGANISM: Artificial sequence
<220> FEATURE:
<223> OTHER INFORMATION: NEFM reverse primer

<400> SEQUENCE: 84

```
taatggctgt cagggcctct t                                       21
```

<210> SEQ ID NO 85
<211> LENGTH: 23
<212> TYPE: DNA

```
<213> ORGANISM: Artificial sequence
<220> FEATURE:
<223> OTHER INFORMATION: LRRK2 forward primer

<400> SEQUENCE: 85
ttttgatgcc atgcactcat ttc                                             23

<210> SEQ ID NO 86
<211> LENGTH: 23
<212> TYPE: DNA
<213> ORGANISM: Artificial sequence
<220> FEATURE:
<223> OTHER INFORMATION: LRRK2 reverse primer

<400> SEQUENCE: 86
ggaatcgcta gggaatgtaa aca                                             23

<210> SEQ ID NO 87
<211> LENGTH: 21
<212> TYPE: DNA
<213> ORGANISM: Artificial sequence
<220> FEATURE:
<223> OTHER INFORMATION: PARK2 forward primer

<400> SEQUENCE: 87
cccacctctg acaaggaaac a                                               21

<210> SEQ ID NO 88
<211> LENGTH: 21
<212> TYPE: DNA
<213> ORGANISM: Artificial sequence
<220> FEATURE:
<223> OTHER INFORMATION: PARK2 reverse primer

<400> SEQUENCE: 88
tcgtgaacaa actgccgatc a                                               21

<210> SEQ ID NO 89
<211> LENGTH: 19
<212> TYPE: DNA
<213> ORGANISM: Artificial sequence
<220> FEATURE:
<223> OTHER INFORMATION: PARK7 forward primer

<400> SEQUENCE: 89
aaccggaagg gcctgatag                                                  19

<210> SEQ ID NO 90
<211> LENGTH: 21
<212> TYPE: DNA
<213> ORGANISM: Artificial sequence
<220> FEATURE:
<223> OTHER INFORMATION: PARK7 reverse primer

<400> SEQUENCE: 90
gcaagagggt gtgttgtaac t                                               21

<210> SEQ ID NO 91
<211> LENGTH: 23
<212> TYPE: DNA
<213> ORGANISM: Artificial sequence
<220> FEATURE:
<223> OTHER INFORMATION: SNCA forward primer

<400> SEQUENCE: 91
aagagggtgt tctctatgta ggc                                             23
```

<210> SEQ ID NO 92
<211> LENGTH: 22
<212> TYPE: DNA
<213> ORGANISM: Artificial sequence
<220> FEATURE:
<223> OTHER INFORMATION: SNCA reverse primer

<400> SEQUENCE: 92
gctcctccaa catttgtcac tt                                          22

<210> SEQ ID NO 93
<211> LENGTH: 21
<212> TYPE: DNA
<213> ORGANISM: Artificial sequence
<220> FEATURE:
<223> OTHER INFORMATION: NCAM forward primer

<400> SEQUENCE: 93
ggctccttgg actcatcttt c                                           21

<210> SEQ ID NO 94
<211> LENGTH: 21
<212> TYPE: DNA
<213> ORGANISM: Artificial sequence
<220> FEATURE:
<223> OTHER INFORMATION: NCAM reverse primer

<400> SEQUENCE: 94
gacatcacct gctacttcct g                                           21

<210> SEQ ID NO 95
<211> LENGTH: 23
<212> TYPE: DNA
<213> ORGANISM: Artificial sequence
<220> FEATURE:
<223> OTHER INFORMATION: MAPT forward primer

<400> SEQUENCE: 95
gaagattggg tccctggaca ata                                         23

<210> SEQ ID NO 96
<211> LENGTH: 20
<212> TYPE: DNA
<213> ORGANISM: Artificial sequence
<220> FEATURE:
<223> OTHER INFORMATION: MAPT reverse primer

<400> SEQUENCE: 96
aggtcagctt gtgggtttca                                             20

<210> SEQ ID NO 97
<211> LENGTH: 24
<212> TYPE: DNA
<213> ORGANISM: Artificial sequence
<220> FEATURE:
<223> OTHER INFORMATION: GAD2 forward primer

<400> SEQUENCE: 97
caaacattta tcaacatgcg cttc                                        24

<210> SEQ ID NO 98
<211> LENGTH: 21
<212> TYPE: DNA
<213> ORGANISM: Artificial sequence
<220> FEATURE:

<223> OTHER INFORMATION: GAD2 reverse primer

<400> SEQUENCE: 98
ctatgacact ggagacaagg c                                    21

<210> SEQ ID NO 99
<211> LENGTH: 22
<212> TYPE: DNA
<213> ORGANISM: Artificial sequence
<220> FEATURE:
<223> OTHER INFORMATION: VGAT forward primer

<400> SEQUENCE: 99
agatgatgag aaacaacccc ag                                   22

<210> SEQ ID NO 100
<211> LENGTH: 20
<212> TYPE: DNA
<213> ORGANISM: Artificial sequence
<220> FEATURE:
<223> OTHER INFORMATION: VGAT reverse primer

<400> SEQUENCE: 100
cacgacaagc ccaaaatcac                                      20

<210> SEQ ID NO 101
<211> LENGTH: 22
<212> TYPE: DNA
<213> ORGANISM: Artificial sequence
<220> FEATURE:
<223> OTHER INFORMATION: DLX5 forward primer

<400> SEQUENCE: 101
acagagactt cacgactccc ag                                   22

<210> SEQ ID NO 102
<211> LENGTH: 20
<212> TYPE: DNA
<213> ORGANISM: Artificial sequence
<220> FEATURE:
<223> OTHER INFORMATION: DLX5 reverse primer

<400> SEQUENCE: 102
tgtggggctg ctctggtcta                                      20

<210> SEQ ID NO 103
<211> LENGTH: 25
<212> TYPE: DNA
<213> ORGANISM: Artificial sequence
<220> FEATURE:
<223> OTHER INFORMATION: DLX6 forward primer

<400> SEQUENCE: 103
tggtgaaaga gaagcatttt ggact                                25

<210> SEQ ID NO 104
<211> LENGTH: 24
<212> TYPE: DNA
<213> ORGANISM: Artificial sequence
<220> FEATURE:
<223> OTHER INFORMATION: DLX6 reverse primer

<400> SEQUENCE: 104
agagaagggc tgttatgtga ggaa                                 24

```
<210> SEQ ID NO 105
<211> LENGTH: 20
<212> TYPE: DNA
<213> ORGANISM: Artificial sequence
<220> FEATURE:
<223> OTHER INFORMATION: SERT forward primer

<400> SEQUENCE: 105
tgctggcttt tgctagctac                                               20

<210> SEQ ID NO 106
<211> LENGTH: 20
<212> TYPE: DNA
<213> ORGANISM: Artificial sequence
<220> FEATURE:
<223> OTHER INFORMATION: SERT reverse primer

<400> SEQUENCE: 106
gaagctcgtc atgcagttca                                               20

<210> SEQ ID NO 107
<211> LENGTH: 21
<212> TYPE: DNA
<213> ORGANISM: Artificial sequence
<220> FEATURE:
<223> OTHER INFORMATION: TPH2 forward primer

<400> SEQUENCE: 107
atggctcaga tccctctac a                                              21

<210> SEQ ID NO 108
<211> LENGTH: 21
<212> TYPE: DNA
<213> ORGANISM: Artificial sequence
<220> FEATURE:
<223> OTHER INFORMATION: TPH2 reverse primer

<400> SEQUENCE: 108
ggatccgcaa gtagtggaac a                                             21

<210> SEQ ID NO 109
<211> LENGTH: 20
<212> TYPE: DNA
<213> ORGANISM: Artificial sequence
<220> FEATURE:
<223> OTHER INFORMATION: VGLUT1 forward primer

<400> SEQUENCE: 109
tcaagtcccc gattccgtgc                                               20

<210> SEQ ID NO 110
<211> LENGTH: 22
<212> TYPE: DNA
<213> ORGANISM: Artificial sequence
<220> FEATURE:
<223> OTHER INFORMATION: VGLUT1 reverse primer

<400> SEQUENCE: 110
tgcgattttg gttgtttccc ca                                            22

<210> SEQ ID NO 111
<211> LENGTH: 20
<212> TYPE: DNA
<213> ORGANISM: Artificial sequence
<220> FEATURE:
<223> OTHER INFORMATION: VGLUT2 forward primer
```

```
<400> SEQUENCE: 111
tggggctaca tcatcactca                                                    20

<210> SEQ ID NO 112
<211> LENGTH: 20
<212> TYPE: DNA
<213> ORGANISM: Artificial sequence
<220> FEATURE:
<223> OTHER INFORMATION: VGLUT2 reverse primer

<400> SEQUENCE: 112
gaagtatggc agctccgaaa                                                    20
```